(12) United States Patent
Sasaki et al.

(10) Patent No.: US 11,560,372 B2
(45) Date of Patent: Jan. 24, 2023

(54) HETEROCYCLIC COMPOUNDS USEFUL AS MODULATORS OF ACETYLCHOLINE RECEPTORS

(71) Applicant: TAKEDA PHARMACEUTICAL COMPANY LIMITED, Osaka (JP)

(72) Inventors: Shinobu Sasaki, Kanagawa (JP); Masaki Seto, Kanagawa (JP); Kazuaki Takami, Kanagawa (JP); Haruhi Ando, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 275 days.

(21) Appl. No.: 16/606,043

(22) PCT Filed: Apr. 17, 2018

(86) PCT No.: PCT/JP2018/016382
§ 371 (c)(1),
(2) Date: Oct. 17, 2019

(87) PCT Pub. No.: WO2018/194181
PCT Pub. Date: Oct. 25, 2018

(65) Prior Publication Data
US 2021/0292308 A1 Sep. 23, 2021

(30) Foreign Application Priority Data
Apr. 18, 2017 (JP) .............................. JP2017-081919

(51) Int. Cl.
| | | |
|---|---|---|
| C07D 405/14 | (2006.01) | |
| A61P 1/10 | (2006.01) | |
| C07D 405/04 | (2006.01) | |
| C07D 409/14 | (2006.01) | |

(52) U.S. Cl.
CPC .............. C07D 405/14 (2013.01); A61P 1/10 (2018.01); C07D 405/04 (2013.01); C07D 409/14 (2013.01)

(58) Field of Classification Search
CPC .. C07D 405/14; C07D 405/04; C07D 409/14; A61P 1/10
See application file for complete search history.

(56) References Cited

U.S. PATENT DOCUMENTS

| | | |
|---|---|---|
| 9,403,802 B2 | 8/2016 | Sakamoto et al. |
| 9,777,005 B2 | 10/2017 | Sugimoto et al. |
| 10,208,046 B2 | 2/2019 | Sugimoto et al. |
| 10,214,508 B2 | 2/2019 | Ogino et al. |
| 10,548,899 B2 * | 2/2020 | Sugimoto ............ C07D 239/88 |
| 2015/0126487 A1 | 5/2015 | Sakamoto et al. |
| 2015/0307497 A1 | 10/2015 | Sugimoto et al. |
| 2017/0081332 A1 | 3/2017 | Sugimoto et al. |
| 2017/0121308 A1 | 5/2017 | Ogino et al. |
| 2018/0303841 A1 | 10/2018 | Sugimoto et al. |
| 2019/0083467 A1 | 3/2019 | Ogino et al. |

FOREIGN PATENT DOCUMENTS

| | | |
|---|---|---|
| WO | 99/37304 | 7/1999 |
| WO | 00/32590 | 6/2000 |
| WO | 01/07436 | 2/2001 |
| WO | 2006/090143 | 8/2006 |
| WO | 2007/020411 | 2/2007 |
| WO | 2011/025851 | 3/2011 |
| WO | 2013/129622 | 9/2013 |
| WO | 2014/077401 | 5/2014 |
| WO | 2014/102233 | 7/2014 |
| WO | 2015/163485 | 10/2015 |
| WO | 2015/174534 | 11/2015 |
| WO | 2015/190564 | 12/2015 |
| WO | 2016/208775 | 12/2016 |
| WO | 2017/069173 | 4/2017 |

(Continued)

OTHER PUBLICATIONS

Kurimoto, J Pharmacol Exp Ther, vol. 364, 28-37, 2018. (Year: 2018).*
Kobayashi, Jpn J Pharmacol, vol. 86, 281-288, 2001. (Year: 2001).*
Harrington A.M. et al., "Immunohistochemical localisation of cholinergic muscarinic receptor subtype 1 (M1r) in the guinea pig and human enteric nervous system", Journal of Chemical Neuroanatomy, 33:193-201, 2007.
Adachi Y. et al., "Comparative Studies on in Vitro Methods for Evaluating in Vivo Function of MDR1 P-Glycoprotein", Pharm. Res. 18(12):1660-1668, 2001.

(Continued)

*Primary Examiner* — D Margaret M Seaman
(74) *Attorney, Agent, or Firm* — Foley & Lardner LLP

(57) ABSTRACT

The present invention aims to provide a compound that may be useful for the prophylaxis or treatment of constipation and the like. The present invention provides a compound represented by the following formula (I): wherein each symbol is as described in the specification, salt thereof.

(I)

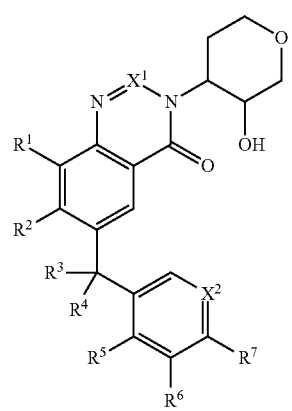

4 Claims, No Drawings

(56) References Cited

FOREIGN PATENT DOCUMENTS

WO   2017/155050   9/2017
WO   2017/155816   9/2017

OTHER PUBLICATIONS

Takeuchi T. et al., "Establishment and Characterization of the Transformants Stably-Expressing MDR1 Derived from Various Animal Species in LLC-PK1", Pharm. Res., 23(7):1460-1472, 2006.
Sugimoto H. et al., "Quantitative Investigation of the Impact of P-Glycoprotein Inhibition on Drug Transport across Blood-Brain Barrier in Rats", Drug Metab. Dispos., 39(1):8-14, 2011.
International Search Report issued in International Application No. PCT/JP2018/016382, dated Jun. 28, 2018, 5 pages.
Written Opinion of the International Search Authority issued in International Application No. PCT/JP2018/016382, dated Jun. 28, 2018, 7 pages.
Mistry, et al., "Novel Fused Arylpyrimidinone Based Allosteric Modulators of the M1 Muscarinic Acetylcholine Receptor", ACS Chemical Neuroscience, vol. 7, No. 5, 2016, pp. 647-661.

\* cited by examiner

HETEROCYCLIC COMPOUNDS USEFUL AS MODULATORS OF ACETYLCHOLINE RECEPTORS

TECHNICAL FIELD

The present invention relates to a heterocyclic compound possibly having a cholinergic muscarinic M1 receptor positive allosteric modulator activity and possibly useful as a medicament such as a prophylactic or therapeutic drug for constipation and the like. As used herein, the positive allosteric modulator activity refers to an action to potentiate receptor function by binding to a moiety different from that of an endogenous activator (acetylcholine for this receptor).

BACKGROUND OF THE INVENTION

Acetylcholine is a neurotransmitter that induces signal transduction in the central nervous system and the neuromuscular connections (the parasympathetic nerve and motor nerve). In the gastrointestinal tract, myenteric plexus, submucosal plexus and the like form a neural network and control gastrointestinal function. Of these, acetylcholine is a major neurotransmitter in the gastrointestinal function and plays a key role in the gastrointestinal motility.

Acetylcholine receptor is classified into a ligand dependent ion channel (cholinergic nicotinic receptor) and a G-protein-conjugated receptor (cholinergic muscarinic receptor). The cholinergic muscarinic receptor is one kind of receptor for excitatory neurotransmitter acetylcholine, and was named based on the selective activation of the receptor by muscarine. The muscarinic receptor is further classified into subtypes of M1 to M5, and the M1 receptor is known to be widely distributed mainly in the brain. On the other hand, expression of M1 receptor in the gastrointestinal nerve plexus is also known and its role of regulating the functions of the gastrointestinal tract has been pointed out (non-patent document 1). From the studies in recent years, promotion of gastrointestinal motility by cholinergic M1 receptor agonist has also been reported.

Generally, peristalsis in the gastrointestinal tract consists of coordinated contraction and relaxation at adjacent sites. It is also known that the cholinergic M1 receptor is expressed in both the excitatory nerve and inhibitory nerve in the gastrointestinal nerve plexus (non-patent document 1).

WO2014/102233 (patent document 1) discloses the following compound which is a COMT inhibitor and useful for the treatment of Parkinson's disease, dementia, depression, schizophrenia and the like.

I

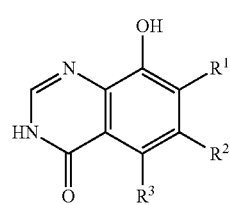

wherein each symbol is as defined in the document.

WO2007/020411 (patent document 2) discloses the following compound which is a cytokine inhibitor and useful for the treatment of rheumatoid arthritis, asthma, inflammatory bowel disease, multiple sclerosis, AIDS, sepsis shock and the like.

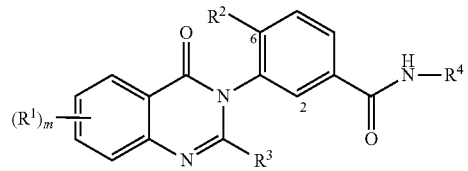

wherein each symbol is as defined in the document.

WO2006/090143 (patent document 3) discloses the following compound which is a cytokine inhibitor and useful for the treatment of rheumatoid arthritis, asthma, inflammatory bowel disease, multiple sclerosis, AIDS, sepsis shock and the like.

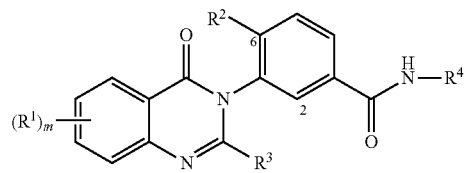

wherein each symbol is as defined in the document.

WO2001/007436 (patent document 4) discloses the following compound which is an FXa inhibitor and useful for the treatment of Alzheimer's disease and the like.

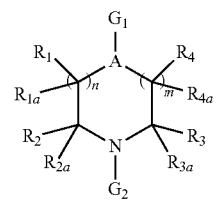

wherein each symbol is as defined in the document.

WO2000/032590 (patent document 5) discloses the following compound which is an FXa inhibitor and useful for the treatment of Alzheimer's disease and the like.

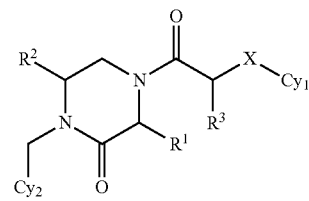

wherein each symbol is as defined in the document.

WO99/37304 (patent document 6) discloses the following compound which is an FXa inhibitor and useful for the treatment of Alzheimer's disease and the like.

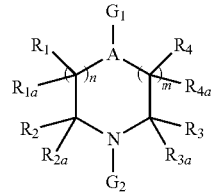

wherein each symbol is as defined in the document.

WO 2013/129622 (patent document 7) discloses the following compound having a cholinergic muscarinic M1 receptor positive allosteric modulator (M1PAM) activity and useful for the treatment of Alzheimer's disease, schizophrenia, pain, sleep disorder and the like.

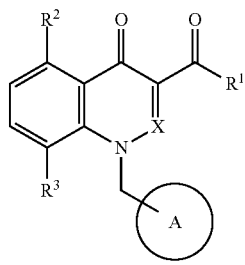

wherein each symbol is as defined in the document.

WO2014/077401 (patent document 8) discloses the following compound having an M1PAM activity and useful for the treatment of Alzheimer's disease, schizophrenia, pain, sleep disorder and the like.

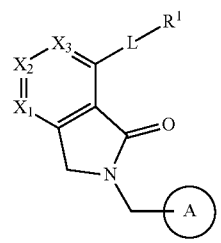

wherein each symbol is as defined in the document.

WO2015/174534 (patent document 9) discloses the following compound having an M1PAM activity and useful for the treatment of Alzheimer's disease, schizophrenia, pain, sleep disorder, Parkinson's disease dementia, Lewy body dementia and the like.

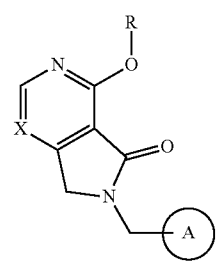

wherein each symbol is as defined in the document.

WO2015/163485 (patent document 10) discloses the following compound having an M1PAM activity and useful for the treatment of Alzheimer's disease, schizophrenia, pain, sleep disorder, Parkinson's disease dementia, Lewy body dementia and the like.

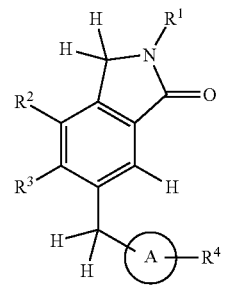

wherein each symbol is as defined in the document.

WO2016/208775 (patent document 11) discloses the following compound having an M1PAM activity and useful for the treatment of Alzheimer's disease, schizophrenia, pain, sleep disorder, Parkinson's disease dementia, Lewy body dementia and the like.

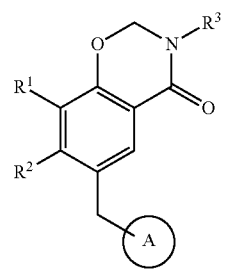

wherein each symbol is as defined in the document.

WO2015/190564 (patent document 12) discloses the following compound having an M1PAM activity and useful for the treatment of Alzheimer's disease, schizophrenia, pain, sleep disorder, Parkinson's disease dementia, Lewy body dementia and the like.

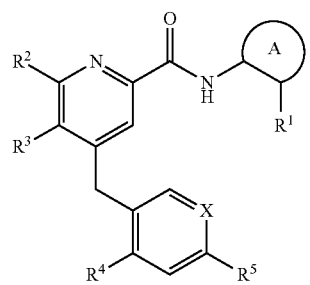

wherein each symbol is as defined in the document.

Non-patent document 2 discloses the following compounds.

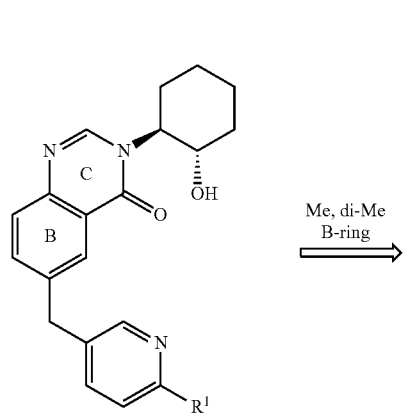

2 R¹ = 1-methylpyrazol-4-yl
3 R¹ = H

Me, di-Me
B-ring
⟹

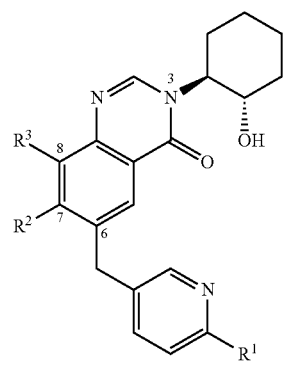

4 R¹ = 1-methylpyrazol-4-yl, R² = H, R³ = Me;
5 R¹ = 1-methylpyrazol-4-yl, R² = Me, R³ = H;
6 R¹ = 1-methylpyrazol-4-yl, R² = Me, R³ = Me;
7 R¹ = H, R² = Me, R³ = Me;

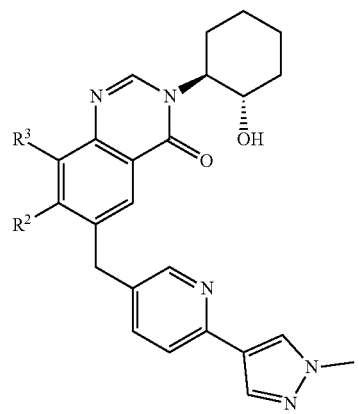

2 R² = R³ = H
4 R² = H, R³ = Me
5 R² = Me, R³ = H
6 R² = R³ = Me

+

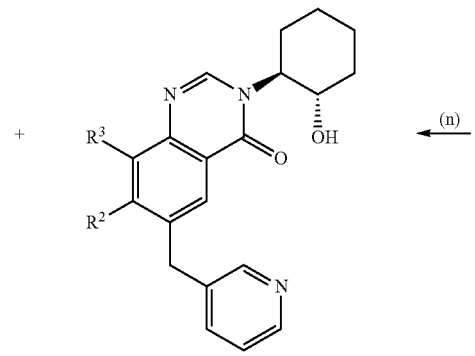

3 R² = R³ = H
7 R² = R³ = Me (n) ←

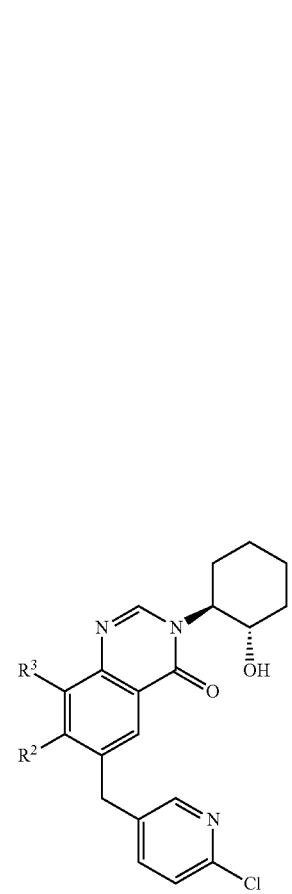

33 R² = R³ = H
34 R² = H, R³ = Me
35 R² = Me, R³ = H
36 R² = R³ = Me

DOCUMENT LIST

Patent Documents patent document 1: WO 2014/102233
patent document 2: WO 2007/020411
patent document 3: WO 2006/090143
patent document 4: WO 2001/007436
patent document 5: WO 2000/032590
patent document 6: WO 99/37304
patent document 7: WO 2013/129622
patent document 8: WO 2014/077401
patent document 9: WO 2015/174534
patent document 10: WO 2015/163485
patent document 11: WO 2016/208775
patent document 12: WO 2015/190564

Non-Patent Documents non-patent document 1: Journal of Chemical Neuroanatomy, 2007 July, 33(4), 193-201 non-patent document 2: ACS Chemical Neuroscience, 2016, 7(5), 647-661

SUMMARY OF THE INVENTION

Problems to be Solved by the Invention

The development of a compound having a cholinergic muscarine M1 receptor (M1 receptor) positive allosteric modulator activity and useful as a prophylactic or therapeutic agent for constipation, for example, constipation associated with neurological disease (e.g., Parkinson's disease, spinal cord injury, multiple sclerosis), age-related constipation, opioid-induced constipation and the like is desired. As used herein, the positive allosteric modulator activity means an action to bind to a site different from an endogenous activator (acetylcholine in this receptor) and potentiate the receptor function.

Means of Solving the Problems

The present inventors have conducted intensive studies in an attempt to solve the aforementioned problems and found that a compound represented by the following formula (I) may have a cholinergic muscarinic M1 receptor positive allosteric modulator activity, which resulted in the completion of the present invention.

Therefore, the present invention relates to the following.

[1] A compound represented by the formula (I):

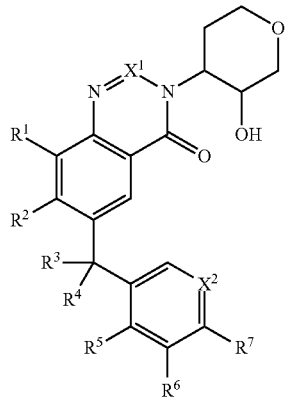

wherein

X$^1$ is CH or N;

X$^2$ is CR$^{10}$ or N;

R$^{10}$ is a hydrogen atom or a halogen atom;

R$^1$ and R$^2$ are each independently a hydrogen atom, a halogen atom, an optionally substituted C$_{1-6}$ alkyl group or an optionally substituted C$_{1-6}$ alkoxy group;

R$^3$ and R$^4$ are each independently a hydrogen atom, a halogen atom, a hydroxy group, an optionally substituted C$_{1-6}$ alkyl group or an optionally substituted C$_{1-6}$ alkoxy group;

R$^5$ and R$^6$ are each independently a hydrogen atom or a halogen atom;

R$^7$ is a substituted monocyclic heterocyclic group, an optionally substituted carbamoyl group, an optionally substituted C$_{1-6}$ alkyl group, a carboxy group, a substituted C$_{1-6}$ alkoxy group, an optionally substituted heteroaryloxy group or a group represented by N(R$^8$)COR$^9$ wherein R$^8$ is a hydrogen atom or an optionally substituted C$_{1-6}$ alkyl group and R$^9$ is an optionally substituted C$_{1-6}$ alkyl group, or a salt thereof (sometimes to be abbreviated as "compound (I)" in the present specification).

[2] The compound described in the above-mentioned [1], wherein

R$^1$ is a hydrogen atom, a halogen atom or a C$_{1-6}$ alkyl group;

R$^2$ is a C$_{1-6}$ alkyl group or a C$_{1-6}$ alkoxy group;

R$^3$ and R$^4$ are each independently a hydrogen atom or a halogen atom;

R$^5$ and R$^6$ are each independently a hydrogen atom or a halogen atom; and

R$^7$ is (1) a 5- or 6-membered monocyclic aromatic heterocyclic group substituted by 1 to 3 substituents selected from (a) a C$_{1-6}$ alkyl group optionally substituted by 1 to 3 substituents selected from a halogen atom, a C$_{3-10}$ cycloalkyl group, a C$_{1-6}$ alkoxy group and a mono- or di-C$_{1-6}$ alkyl-carbamoyl group, (b) a C$_{3-10}$ cycloalkyl group, and (c) a 3- to 8-membered monocyclic non-aromatic heterocyclic group, (2) a carbamoyl group substituted by 1 or 2 substituents selected from (a) a C$_{1-6}$ alkyl group optionally substituted by 1 to 3 substituents selected from (i) a halogen atom, (ii) a C$_{3-10}$ cycloalkyl group optionally substituted by 1 to 3 hydroxy groups, (iii) a mono- or di-C$_{1-6}$ alkyl-carbamoyl group, (iv) a C$_{1-6}$ alkoxy group, (v) a hydroxy group, (vi) a 3- to 8-membered monocyclic non-aromatic heterocyclic group optionally substituted by one oxo group, and (vii) a C$_{1-6}$ alkylsulfonyl group, (b) a C$_{3-10}$ cycloalkyl group optionally substituted by 1 to 3 substituents selected from a halogen atom, an optionally halogenated C$_{1-6}$ alkyl group and a cyano group, and (c) a 3- to 8-membered monocyclic non-aromatic heterocyclic group optionally substituted by 1 to 3 substituents selected from a C$_{1-6}$ alkyl group, an oxo group and a hydroxy group, (3) an azetidin-1-ylcarbonyl group optionally substituted by 1 to 3 substituents selected from an optionally halogenated C$_{1-6}$ alkyl group, a hydroxy group and a C$_{1-6}$ alkoxy group, (4) a C$_{1-6}$ alkyl group, or (5) a carboxy group, or a salt thereof.

[3] The compound described in the above-mentioned [1] or [2], wherein

R$^7$ is a carbamoyl group substituted by 1 or 2 substituents selected from (a) a C$_{1-6}$ alkyl group optionally substituted by 1 to 3 substituents selected from (i) a halogen atom, (ii) a C$_{3-10}$ cycloalkyl group optionally substituted by 1 to 3 hydroxy groups, (iii) a mono- or di-C$_{1-6}$ alkyl-carbamoyl group, (iv) a C$_{1-6}$ alkoxy group, (v) a hydroxy group, (vi) a 3- to 8-membered monocyclic non-aromatic heterocyclic group optionally substituted by one oxo group, and (vii) a C$_{1-6}$ alkylsulfonyl group, (b) a C$_{3-10}$ cycloalkyl group optionally substituted by 1 to 3 substituents selected from a halogen atom, an optionally halogenated C$_{1-6}$ alkyl group and a cyano group, and (c) a 3- to 8-membered monocyclic non-aromatic heterocyclic group optionally substituted by 1 to 3 substituents selected from a C$_{1-6}$ alkyl group, an oxo group and a hydroxy group, or a salt thereof.

[4] The compound described in the above-mentioned [1], wherein

R$^1$ is a halogen atom or a C$_{1-6}$ alkyl group;

R$^2$ is a C$_{1-6}$ alkyl group;

R$^3$ is a hydrogen atom;

R$^4$ is a hydrogen atom;

R$^5$ is a hydrogen atom;

R$^6$ is a hydrogen atom or a halogen atom; and

R$^7$ is (1) a 5- or 6-membered monocyclic aromatic heterocyclic group substituted by 1 to 3 substituents selected from (a) a C$_{1-6}$ alkyl group optionally substituted by 1 to 3 substituents selected from a C$_{3-10}$ cycloalkyl group and a C$_{1-6}$ alkoxy group, (b) a C$_{3-10}$ cycloalkyl group, and (c) a 3- to 8-membered monocyclic non-aromatic heterocyclic group, (2) a carbamoyl group substituted by 1 or 2 substituents selected from
(a) a $C_{1-6}$ alkyl group optionally substituted by 1 to 3 substituents selected from (i) a $C_{3-10}$ cycloalkyl group optionally substituted by 1 to 3 hydroxy groups, (ii) a mono- or di-$C_{1-6}$ alkyl-carbamoyl group, (iii) a $C_{1-6}$ alkoxy group, (iv) a hydroxy group, (v) a 3- to 8-membered monocyclic non-aromatic heterocyclic group optionally substituted by one oxo group, and
(vi) a $C_{1-6}$ alkylsulfonyl group,
(b) a $C_{3-10}$ cycloalkyl group optionally substituted by 1 to 3 halogen atoms, and
(c) a 3- to 8-membered monocyclic non-aromatic heterocyclic group optionally substituted by 1 to 3 substituents selected from a $C_{1-6}$ alkyl group and an oxo group, or
(3) an azetidin-1-ylcarbonyl group optionally substituted by 1 to 3 $C_{1-6}$ alkoxy groups,
or a salt thereof.
[5] The compound described in the above-mentioned [1], wherein
$R^1$ is a halogen atom or a $C_{1-6}$ alkyl group;
$R^2$ is a $C_{1-6}$ alkyl group;
$R^3$ is a hydrogen atom;
$R^4$ is a hydrogen atom;
$R^5$ is a hydrogen atom;
$R^6$ is a hydrogen atom or a halogen atom; and
$R^7$ is
(1) a 5- or 6-membered monocyclic aromatic heterocyclic group substituted by 1 to 3 $C_{1-6}$ alkyl groups, or
(2) a carbamoyl group substituted by a $C_{1-6}$ alkyl group optionally substituted by one substituent selected from a $C_{1-6}$ alkoxy group and a 3- to 8-membered monocyclic non-aromatic heterocyclic group,
or a salt thereof.
[6] 3-((3R,4S)-3-Hydroxytetrahydro-2H-pyran-4-yl)-7,8-dimethyl-6-((6-(1-methyl-1H-1,2,3-triazol-4-yl)pyridin-3-yl)methyl)quinazolin-4(3H)-one,
or a salt thereof.
[7] 2-Fluoro-4-((3-((3R,4S)-3-hydroxytetrahydro-2H-pyran-4-yl)-7,8-dimethyl-4-oxo-3,4-dihydroquinazolin-6-yl)methyl)-N-methylbenzamide,
or a salt thereof.
[8] 6-((6-(1,3-Dimethyl-1H-pyrazol-4-yl)pyridin-3-yl)methyl)-3-((3R,4S)-3-hydroxytetrahydro-2H-pyran-4-yl)-7,8-dimethylquinazolin-4(3H)-one,
or a salt thereof.
[9] 3-((3R,4S)-3-Hydroxytetrahydro-2H-pyran-4-yl)-7,8-dimethyl-6-((6-(1-methyl-1H-pyrazol-4-yl)pyridin-3-yl)methyl)quinazolin-4 (3H)-one,
or a salt thereof.
[10] 4-((8-Chloro-3-((3R,4S)-3-hydroxytetrahydro-2H-pyran-4-yl)-7-methyl-4-oxo-3,4-dihydrobenzo[d][1,2,3]triazin-6-yl)methyl)-2-fluoro-N-methylbenzamide,
or a salt thereof.
[11] 2-Fluoro-4-((3-((3R,4S)-3-hydroxytetrahydro-2H-pyran-4-yl)-7,8-dimethyl-4-oxo-3,4-dihydroquinazolin-6-yl)methyl)-N-(2-methoxyethyl)benzamide,
or a salt thereof.
[12] 2-Fluoro-4-((3-((3R,4S)-3-hydroxytetrahydro-2H-pyran-4-yl)-7,8-dimethyl-4-oxo-3,4-dihydroquinazolin-6-yl)methyl)-N—(((R)-tetrahydrofuran-2-yl)methyl)benzamide,
or a salt thereof.
[13] A medicament comprising the compound described in the above-mentioned [1] or a salt thereof.
[14] The medicament described in the above-mentioned [13], which is a cholinergic muscarinic M1 receptor positive allosteric modulator.
[15] The medicament described in the above-mentioned [13], which is a prophylactic or therapeutic agent for constipation.
[16] A method of cholinergic muscarinic M1 receptor positive allosteric modulation in a mammal, comprising administering an effective amount of the compound described in the above-mentioned [1] or a salt thereof to said mammal.
[17] A method for the prophylaxis or treatment of constipation in a mammal, comprising administering an effective amount of the compound described in the above-mentioned [1] or a salt thereof to the mammal.
[18] Use of the compound described in the above-mentioned [1] or a salt thereof in the production of a prophylactic or therapeutic agent for constipation.
[19] The compound described in the above-mentioned [1] or a salt thereof for use in the prophylaxis or treatment of constipation.

Effect of the Invention

The compound of the present invention may have a cholinergic muscarinic M1 receptor positive allosteric modulator activity, and may be useful as a medicament such as a prophylactic or therapeutic drug for, for example, constipation, such as constipation associated with neurological disease (e.g., Parkinson's disease, spinal cord injury, multiple sclerosis), age-related constipation, opioid-induced constipation and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),

(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., 20 methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocyclic group" include an aromatic heterocyclic group and a non-aromatic heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycycle (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocyclic groups such as aziridine, oxirane, thiirane, azetidine, oxetane, thietane, tetrahydrothiophene, tetrahydrofuran, Pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzoimidazole, dihydrobenzooxazole, dihydrobenzothiazole, dihydrobenzoisothiazole, dihydronaphto[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include the "heterocycle" containing at least one nitrogen atom as a ring-constituting atom.

In the present specification, examples of the "$C_{3-10}$ cycloalkyl group" also include bicyclo[1.1.1]pentyl.

Each symbol in the formula (I) is explained below.

$X^1$ is CH or N.

In one embodiment of the present invention, $X^1$ is preferably CH.

In another embodiment of the present invention, $X^1$ is preferably N.

$X^2$ is $CR^{10}$ or N, and $R^{10}$ is a hydrogen atom or a halogen atom.

In one embodiment of the present invention, $X^2$ is preferably $CR^{10}$.

In another embodiment of the present invention, $X^2$ is preferably N.

As the halogen atom for $R^{10}$, a fluorine atom, a chlorine atom and a bromine atom can be mentioned, with preference given to a fluorine atom.

In one embodiment of the present invention, $R^{10}$ is preferably a hydrogen atom or a fluorine atom.

In another embodiment of the present invention, $R^{10}$ is preferably a halogen atom, more preferably a fluorine atom.

$R^1$ and $R^2$ are each independently a hydrogen atom, a halogen atom, an optionally substituted $C_{1-6}$ alkyl group, or an optionally substituted $C_{1-6}$ alkoxy group.

$R^1$ is preferably a hydrogen atom, a halogen atom (e.g., chlorine atom, fluorine atom), a $C_{1-6}$ alkyl group (e.g., methyl), or a $C_{1-6}$ alkoxy group (e.g., methoxy), more preferably, a hydrogen atom, a halogen atom (e.g., chlorine atom, fluorine atom), or a $C_{1-6}$ alkyl group (e.g., methyl), further preferably a halogen atom (e.g., chlorine atom) or a $C_{1-6}$ alkyl group (e.g., methyl).

$R^2$ is preferably a hydrogen atom, a halogen atom (e.g., chlorine atom, fluorine atom), a $C_{1-6}$ alkyl group (e.g., methyl), or a $C_{1-6}$ alkoxy group (e.g., methoxy), more preferably a $C_{1-6}$ alkyl group (e.g., methyl) or a $C_{1-6}$ alkoxy group (e.g., methoxy), further preferably a $C_{1-6}$ alkyl group (e.g., methyl).

In a preferable embodiment of the present invention, when one of $R^1$ and $R^2$ is a hydrogen atom, the other is other than a hydrogen atom.

In one embodiment of the present invention, $R^1$ is a $C_{1-6}$ alkyl group (e.g., methyl) or a halogen atom (e.g., chlorine atom, fluorine atom), and $R^2$ is a $C_{1-6}$ alkyl group (e.g., methyl).

In another embodiment of the present invention, $R^1$ is a hydrogen atom and $R^2$ is a $C_{1-6}$ alkoxy group (e.g., methoxy).

$R^3$ and $R^4$ are each independently a hydrogen atom, a halogen atom, a hydroxy group, an optionally substituted $C_{1-6}$ alkyl group, or an optionally substituted $C_{1-6}$ alkoxy group.

Preferably, $R^3$ and $R^4$ are each independently a hydrogen atom, a halogen atom, a hydroxy group, a $C_{1-6}$ alkyl group or a $C_{1-6}$ alkoxy group, further preferably a hydrogen atom.

$R^5$ and $R^6$ are each independently a hydrogen atom or a halogen atom.

Examples of the halogen atom for $R^5$ or $R^6$ include a fluorine atom, a chlorine atom and a bromine atom.

In one embodiment of the present invention, $R^5$ and $R^6$ are each preferably a hydrogen atom.

In another embodiment of the present invention, $R^5$ is a hydrogen atom, and $R^6$ is a hydrogen atom or a halogen atom (e.g., fluorine atom).

$R^7$ is a substituted monocyclic heterocyclic group, an optionally substituted carbamoyl group, an optionally substituted $C_{1-6}$ alkyl group, a carboxy group, a substituted $C_{1-6}$ alkoxy group, an optionally substituted heteroaryloxy group, or a group represented by $N(R^8)COR^9$ wherein $R^8$ is a hydrogen atom or an optionally substituted $C_{1-6}$ alkyl group and $R^9$ is an optionally substituted $C_{1-6}$ alkyl group.

As the "monocyclic heterocyclic group" of the "substituted monocyclic heterocyclic group" for $R^7$, a 5- or 6-membered monocyclic aromatic heterocyclic group, a 3- to 8-membered monocyclic non-aromatic heterocyclic group and the like can be mentioned.

As the "5- or 6-membered monocyclic aromatic heterocyclic group" exemplified as the aforementioned "monocyclic heterocyclic group", a 5- or 6-membered monocyclic aromatic heterocyclic group containing, as a ring-constituting atom besides carbon atom, 1 to 4 hetero atoms selected from a nitrogen atom, a sulfur atom and an oxygen atom can be mentioned. Specifically, those similar to the examples recited as the "5- or 6-membered monocyclic aromatic heterocyclic group" from among the preferable examples of the aforementioned "aromatic heterocyclic group" can be mentioned.

As the "3- or 8-membered monocyclic non-aromatic heterocyclic group" exemplified as the aforementioned "monocyclic heterocyclic group", a 3- or 8-membered monocyclic non-aromatic heterocyclic group containing, as a ring-constituting atom besides carbon atom, 1 to 4 hetero atoms selected from a nitrogen atom, a sulfur atom and an oxygen atom can be mentioned. Specifically, those similar to the examples recited as the "3- or 8-membered monocyclic non-aromatic heterocyclic group" from among the preferable examples of the aforementioned "non-aromatic heterocyclic group" can be mentioned.

As the "monocyclic heterocyclic group", a 5- or 6-membered monocyclic aromatic heterocyclic group (e.g., pyrazolyl, triazolyl, imidazolyl, pyridazinyl) and a 3- to 8-membered monocyclic non-aromatic heterocyclic group (e.g., pyrrolidinyl, piperidinyl, piperazinyl, morpholinyl) can be mentioned. Preferably, a 5- or 6-membered monocyclic aromatic heterocyclic group (e.g., pyrazolyl, triazolyl, imidazolyl, pyridazinyl) can be mentioned, and further preferably, pyrazolyl and triazolyl can be mentioned.

The "monocyclic heterocyclic group" of the "substituted monocyclic heterocyclic group" for $R^7$ optionally has 1 to 5 (preferably 1 to 3) substituents at substitutable position(s). Examples of such substituent include the aforementioned "substituent" and an oxo group. When plural substituents are present, the respective substituents may be the same or different.

As the substituent of the "substituted monocyclic heterocyclic group" for $R^7$, an optionally substituted $C_{1-6}$ alkyl group, an optionally substituted $C_{3-10}$ cycloalkyl group, an optionally substituted heterocyclic group, an oxo group and the like can be mentioned.

The "substituted monocyclic heterocyclic group" for $R^7$ is preferably a 5- or 6-membered monocyclic aromatic heterocyclic group (e.g., pyrazolyl, triazolyl, imidazolyl, pyridazinyl) substituted by 1 to 3 (preferably 1 or 2) substituents selected from (a) a $C_{1-6}$ alkyl group (e.g., methyl, ethyl, tert-butyl) optionally substituted by 1 to 3 substituents selected from a halogen atom (e.g., fluorine atom), a $C_{3-10}$ cycloalkyl group (e.g., cyclopropyl), a $C_{1-6}$ alkoxy group (e.g., methoxy), and a mono- or di-$C_{1-6}$ alkyl-carbamoyl group (e.g., dimethylcarbamoyl), (b) a $C_{3-10}$ cycloalkyl group (e.g., cyclopropyl), and (c) a 3- to 8-membered monocyclic non-aromatic heterocyclic group (e.g., tetrahydropyranyl).

As the "optionally substituted carbamoyl group" for $R^7$, the aforementioned "optionally substituted carbamoyl group" can be mentioned.

The two substituents that the "carbamoyl group" of the "optionally substituted carbamoyl group" has may form an optionally substituted ring together with the adjacent nitrogen atom. As such ring, azetidine, pyrrolidine, piperidine, piperazine, morpholine, thiomorpholine, azepane, diazepane, azocane, diazocane, oxazepane and the like can be mentioned. The ring optionally has 1 to 5 (preferably 1 to 3) substituents at substitutable position(s). Examples of such substituent include the aforementioned "substituent". When plural substituents are present, the respective substituents may be the same or different.

Specifically, azetidin-1-ylcarbonyl, pyrrolidin-1-ylcarbonyl, piperidin-1-ylcarbonyl, piperazin-1-ylcarbonyl, morpholin-4-ylcarbonyl, thiomorpholin-4-ylcarbonyl, azepan-1-ylcarbonyl, 1,4-diazepan-1-ylcarbonyl, azocan-1-ylcarbonyl, 1,5-diazocan-1-ylcarbonyl, 1,4-oxazepan-4-ylcarbonyl and the like, each of which is optionally substituted, can be mentioned. Preferred is azetidin-1-ylcarbonyl. Examples of the substituent on the ring include 1 to 3 substituents selected from an optionally halogenated $C_{1-6}$ alkyl group, a hydroxy group, a $C_{1-6}$ alkoxy group and the like.

The "optionally substituted carbamoyl group" for $R^7$ is preferably
(1) a carbamoyl group optionally substituted by 1 or 2 (preferably 1) substituents selected from
(a) an optionally substituted $C_{1-6}$ alkyl group,
(b) an optionally substituted $C_{3-10}$ cycloalkyl group, and
(c) an optionally substituted heterocyclic group, or
(2) an optionally substituted azetidin-1-ylcarbonyl group.

The "optionally substituted carbamoyl group" for $R^7$ is more preferably
(1) a carbamoyl group substituted by 1 or 2 (preferably 1) substituents selected from
(a) a $C_{1-6}$ alkyl group (e.g., methyl, ethyl, propyl, isopropyl, isobutyl, tert-butyl) optionally substituted by 1 to 3 substituents selected from
  (i) a halogen atom (e.g., fluorine atom),
  (ii) a $C_{3-10}$ cycloalkyl group (e.g., cyclopropyl) optionally substituted by 1 to 3 (preferably 1) hydroxy groups,
  (iii) a mono- or di-$C_{1-6}$ alkyl-carbamoyl group (e.g., dimethylcarbamoyl),
  (iv) a $C_{1-6}$ alkoxy group (e.g., methoxy, ethoxy),
  (v) a hydroxy group,
  (vi) a 3- to 8-membered monocyclic non-aromatic heterocyclic group (e.g., oxetanyl, tetrahydrofuranyl, pyrrolidinyl, tetrahydropyranyl, morpholinyl) optionally substituted by one oxo group, and
  (vii) a $C_{1-6}$ alkylsulfonyl group (e.g., methylsulfonyl),
(b) a $C_{3-10}$ cycloalkyl group (e.g., cyclopropyl, cyclobutyl, bicyclo[1.1.1]pentyl) optionally substituted by 1 to 3 (preferably 1 or 2) substituents selected from a halogen atom (e.g., fluorine atom), an optionally halogenated $C_{1-6}$ alkyl group (e.g., methyl, difluoromethyl) and a cyano group, and
(c) a 3- to 8-membered monocyclic non-aromatic heterocyclic group (e.g., oxetanyl, thietanyl, tetrahydrofuranyl, tetrahydropyranyl) optionally substituted by 1 to 3 (preferably 1 or 2) substituents selected from a $C_{1-6}$ alkyl group (e.g., methyl), an oxo group and a hydroxy group, or
(2) an azetidin-1-ylcarbonyl group optionally substituted by 1 to 3 (preferably 1) substituents selected from an optionally halogenated $C_{1-6}$ alkyl group (e.g., difluoromethyl), a hydroxy group and a $C_{1-6}$ alkoxy group (e.g., methoxy).

The "$C_{1-6}$ alkyl group" of the "optionally substituted $C_{1-6}$ alkyl group" for $R^7$ optionally has 1 to 5 (preferably 1 to 3) substituents at substitutable position(s). Examples of such substituent include the aforementioned "substituent". When plural substituents are present, the respective substituents may be the same or different.

The "optionally substituted $C_{1-6}$ alkyl group" for $R^7$ is preferably a $C_{1-6}$ alkyl group.

The "$C_{1-6}$ alkoxy group" of the "substituted $C_{1-6}$ alkoxy group" for $R^7$ optionally has 1 to 5 (preferably 1 to 3) substituents at substitutable position(s). Examples of such substituent include the aforementioned "substituent". When plural substituents are present, the respective substituents may be the same or different.

The "substituted $C_{1-6}$ alkoxy group" for $R^7$ is preferably a $C_{1-6}$ alkoxy group substituted by 1 to 3 substituents selected from a halogen atom, a hydroxy group, a $C_{1-6}$ alkoxy group and the like.

As the "heteroaryloxy group" of the "optionally substituted heteroaryloxy group" for $R^7$, a heteroaryloxy group wherein the heteroaryl moiety is the aforementioned "aromatic heterocyclic group" can be mentioned. Examples of the heteroaryl moiety include those similar to the examples recited for the aforementioned "aromatic heterocyclic group".

The "heteroaryloxy group" of the "optionally substituted heteroaryloxy group" for $R^7$ optionally has 1 to 5 (preferably 1 to 3) substituents at substitutable position(s). Examples of such substituent include the aforementioned "substituent". When plural substituents are present, the respective substituents may be the same or different.

When $R^7$ is a group represented by $N(R^8)COR^9$, $R^8$ is a hydrogen atom or an optionally substituted $C_{1-6}$ alkyl group, and $R^9$ is an optionally substituted $C_{1-6}$ alkyl group.

The "$C_{1-6}$ alkyl group" of the "optionally substituted $C_{1-6}$ alkyl group" for $R^8$ or $R^9$ optionally has 1 to 5 (preferably 1 to 3) substituents at substitutable position(s). Examples of such substituent include the aforementioned "substituent". When plural substituents are present, the respective substituents may be the same or different.

The "optionally substituted $C_{1-6}$ alkyl group" for $R^8$ or $R^9$ is preferably a $C_{1-6}$ alkyl group.

$R^7$ is preferably
(1) a 5- or 6-membered monocyclic aromatic heterocyclic group (e.g., pyrazolyl, triazolyl, imidazolyl, pyridazinyl) substituted by 1 to 3 (preferably 1 or 2) substituents selected from
(a) a $C_{1-6}$ alkyl group (e.g., methyl, ethyl, tert-butyl) optionally substituted by 1 to 3 substituents selected from a halogen atom (e.g., fluorine atom), a $C_{3-10}$ cycloalkyl group (e.g., cyclopropyl), a $C_{1-6}$ alkoxy group (e.g., methoxy), and a mono- or di-$C_{1-6}$ alkyl-carbamoyl group (e.g., dimethylcarbamoyl),
(b) a $C_{3-10}$ cycloalkyl group (e.g., cyclopropyl), and
(c) a 3- to 8-membered monocyclic non-aromatic heterocyclic group (e.g., tetrahydropyranyl),
(2) a carbamoyl group substituted by 1 or 2 (preferably 1) substituents selected from
(a) a $C_{1-6}$ alkyl group (e.g., methyl, ethyl, propyl, isopropyl, isobutyl, tert-butyl) optionally substituted by 1 to 3 substituents selected from
  (i) a halogen atom (e.g., fluorine atom),
  (ii) a $C_{3-10}$ cycloalkyl group (e.g., cyclopropyl) optionally substituted by 1 to 3 (preferably 1) hydroxy groups,
  (iii) a mono- or di-$C_{1-6}$ alkyl-carbamoyl group (e.g., dimethylcarbamoyl),
  (iv) a $C_{1-6}$ alkoxy group (e.g., methoxy, ethoxy),
  (v) a hydroxy group,
  (vi) a 3- to 8-membered monocyclic non-aromatic heterocyclic group (e.g., oxetanyl, tetrahydrofuranyl, pyrrolidinyl, tetrahydropyranyl, morpholinyl) optionally substituted by one oxo group, and
  (vii) a $C_{1-6}$ alkylsulfonyl group (e.g., methylsulfonyl),
(b) a $C_{3-10}$ cycloalkyl group (e.g., cyclopropyl, cyclobutyl, bicyclo[1.1.1]pentyl) optionally substituted by 1 to 3 (preferably 1 or 2) substituents selected from a halogen atom (e.g., fluorine atom), an optionally halogenated $C_{1-6}$ alkyl group (e.g., methyl, difluoromethyl) and a cyano group, and
(c) a 3- to 8-membered monocyclic non-aromatic heterocyclic group (e.g., oxetanyl, thietanyl, tetrahydrofuranyl, tetrahydropyranyl) optionally substituted by 1 to 3 (preferably 1 or 2) substituents selected from a $C_{1-6}$ alkyl group (e.g., methyl), an oxo group and a hydroxy group,
(3) an azetidin-1-ylcarbonyl group optionally substituted by 1 to 3 (preferably 1) substituents selected from an optionally halogenated $C_{1-6}$ alkyl group (e.g., difluoromethyl), a hydroxy group and a $C_{1-6}$ alkoxy group (e.g., methoxy)
(4) a $C_{1-6}$ alkyl group (e.g., methyl), or
(5) a carboxy group.

$R^7$ is more preferably, (1) a 5- or 6-membered monocyclic aromatic heterocyclic group (e.g., pyrazolyl, triazolyl, imidazolyl, pyridazinyl) substituted by 1 to 3 (preferably 1 or 2) substituents selected from (a) a $C_{1-6}$ alkyl group (e.g., methyl, ethyl) optionally substituted by 1 to 3 (preferably 1) substituents selected from a $C_{3-10}$ cycloalkyl group (e.g., cyclopropyl) and a $C_{1-6}$ alkoxy group (e.g., methoxy), (b) a $C_{3-10}$ cycloalkyl group (e.g., cyclopropyl), and (c) a 3- to 8-membered monocyclic non-aromatic heterocyclic group (e.g., tetrahydropyranyl), (2) a carbamoyl group substituted by 1 or 2 (preferably 1) substituents selected from (a) a $C_{1-6}$ alkyl group (e.g., methyl, ethyl, propyl, isobutyl) optionally substituted by 1 to 3 substituents selected from (i) a $C_{3-10}$ cycloalkyl group (e.g., cyclopropyl) optionally substituted by 1 to 3 (preferably 1) hydroxy groups, (ii) a mono- or di-$C_{1-6}$ alkyl-carbamoyl group (e.g., dimethylcarbamoyl), (iii) a $C_{1-6}$ alkoxy group (e.g., methoxy, ethoxy), (iv) a hydroxy group, (v) a 3- to 8-membered monocyclic non-aromatic heterocyclic group (e.g., oxetanyl, tetrahydrofuranyl, pyrrolidinyl) optionally substituted by one oxo group, and (vi) a $C_{1-6}$ alkylsulfonyl group (e.g., methylsulfonyl), (b) a $C_{3-10}$ cycloalkyl group (e.g., cyclopropyl, cyclobutyl) optionally substituted by 1 to 3 (preferably 1 or 2) halogen atoms (e.g., fluorine atom), and (c) a 3- to 8-membered monocyclic non-aromatic heterocyclic group (e.g., oxetanyl, thietanyl, tetrahydrofuranyl) optionally substituted by 1 to 3 (preferably 1 or 2) substituents selected from a $C_{1-6}$ alkyl group (e.g., methyl) and an oxo group, or (3) an azetidin-1-ylcarbonyl group optionally substituted by 1 to 3 (preferably 1) $C_{1-6}$ alkoxy groups (e.g., methoxy).

$R^7$ is further preferably, (1) a pyrazolyl group or a triazolyl group each substituted by 1 or 2 substituents selected from (a) a $C_{1-6}$ alkyl group (e.g., methyl, ethyl, tert-butyl) optionally substituted by 1 to 3 substituents selected from a halogen atom (e.g., fluorine atom), a $C_{3-10}$ cycloalkyl group (e.g., cyclopropyl), and a $C_{1-6}$ alkoxy group (e.g., methoxy), and (b) a 3- to 8-membered monocyclic non-aromatic heterocyclic group (e.g., tetrahydropyranyl), or (2) a carbamoyl group substituted by one substituent selected from (a) a $C_{1-6}$ alkyl group (e.g., methyl, ethyl, propyl) optionally substituted by 1 to 3 (preferably 1) substituents selected from a $C_{1-6}$ alkoxy group (e.g., methoxy, ethoxy) and a 3- to 8-membered monocyclic non-aromatic heterocyclic group (e.g., tetrahydrofuranyl), and (b) a $C_{3-10}$ cycloalkyl group (e.g., cyclopropyl).

$R^7$ is furthermore preferably (1) a 5- or 6-membered monocyclic aromatic heterocyclic group (e.g., triazolyl, pyrazolyl) substituted by 1 to 3 $C_{1-6}$ alkyl groups, or (2) a carbamoyl group substituted by a $C_{1-6}$ alkyl group optionally substituted by one substituent selected from a $C_{1-6}$ alkoxy group and a 3- to 8-membered monocyclic non-aromatic heterocyclic group (e.g., tetrahydrofuranyl).

In one embodiment of the present invention, compound (I) is preferably a compound having a steric structure represented by the formula (I)-1, or a salt thereof.

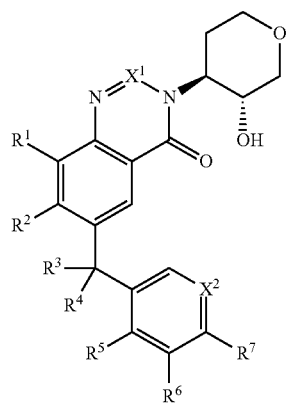

(I)-1 wherein each symbol is as defined above.

As preferable embodiments of compound (I), the following compounds can be mentioned.

[Compound I-1]

Compound (I) wherein $X^1$ is a CH or N;

$X^2$ is a $CR^{10}$ or N;

$R^{10}$ is a hydrogen atom or a halogen atom (e.g., fluorine atom);

$R^1$ and $R^2$ are each independently a hydrogen atom, a halogen atom (e.g., chlorine atom, fluorine atom), a $C_{1-6}$ alkyl group (e.g., methyl) or a $C_{1-6}$ alkoxy group (e.g., methoxy);

$R^3$ and $R^4$ are each independently a hydrogen atom or a halogen atom (e.g., fluorine atom);

$R^5$ and $R^6$ are each a hydrogen atom; and $R^7$ is (1) a 5- or 6-membered monocyclic aromatic heterocyclic group (e.g., pyrazolyl, triazolyl, imidazolyl, pyridazinyl) substituted by 1 to 3 substituents selected from (a) a $C_{1-6}$ alkyl group (e.g., methyl, ethyl, tert-butyl) optionally substituted by 1 to 3 substituents selected from a halogen atom (e.g., fluorine atom), a $C_{3-10}$ cycloalkyl group (e.g., cyclopropyl), a $C_{1-6}$ alkoxy group (e.g., methoxy), and a mono- or di-$C_{1-6}$ alkyl-carbamoyl group (e.g., dimethylcarbamoyl), (b) a $C_{3-10}$ cycloalkyl group (e.g., cyclopropyl), and (c) a 3- to 8-membered monocyclic non-aromatic heterocyclic group (e.g., tetrahydropyranyl), (2) a carbamoyl group substituted by 1 or 2 (preferably 1) substituents selected from (a) a $C_{1-6}$ alkyl group (e.g., methyl, ethyl, propyl, isopropyl, isobutyl, tert-butyl) optionally substituted by 1 to 3 substituents selected from (i) a halogen atom (e.g., fluorine atom), (ii) a $C_{3-10}$ cycloalkyl group (e.g., cyclopropyl) optionally substituted by 1 to 3 hydroxy groups, (iii) a mono- or di-$C_{1-6}$ alkyl-carbamoyl group (e.g., dimethylcarbamoyl), (iv) a $C_{1-6}$ alkoxy group (e.g., methoxy, ethoxy), (v) a hydroxy group, (vi) a 3- to 8-membered monocyclic non-aromatic heterocyclic group (e.g., oxetanyl, tetrahydrofuranyl, pyrrolidinyl, tetrahydropyranyl, morpholinyl) optionally substituted by one oxo group, and (vii) a $C_{1-6}$ alkylsulfonyl group (e.g., methylsulfonyl), (b) a $C_{3-10}$ cycloalkyl group (e.g., cyclopropyl, cyclobutyl, bicyclo[1.1.1]pentyl) optionally substituted by 1 to 3 substituents selected from a halogen atom (e.g., fluorine atom), an optionally halogenated $C_{1-6}$ alkyl group (e.g., methyl, difluoromethyl), and a cyano group, and (c) a 3- to 8-membered monocyclic non-aromatic heterocyclic group (e.g., oxetanyl, thietanyl, tetrahydrofuranyl, tetrahydropyranyl) optionally substituted by 1 to 3 substituents selected from a $C_{1-6}$ alkyl group (e.g., methyl), an oxo group and a hydroxy group, (3) an azetidin-1-ylcarbonyl group optionally substituted by 1 to 3 substituents selected from an optionally halogenated $C_{1-6}$ alkyl group (e.g., difluoromethyl), a hydroxy group and a $C_{1-6}$ alkoxy group (e.g., methoxy), (4) a $C_{1-6}$ alkyl group (e.g., methyl), or (5) a carboxy group.

[Compound I-2]

Compound (I) wherein $X^1$ is a CH or N;

$X^2$ is a $CR^{10}$ or N;

$R^{10}$ is a hydrogen atom or a halogen atom (e.g., fluorine atom);

$R^1$ and $R^2$ are each independently a hydrogen atom, a halogen atom (e.g., chlorine atom, fluorine atom), a $C_{1-6}$ alkyl group (e.g., methyl) or a $C_{1-6}$ alkoxy group (e.g., methoxy);

$R^3$ and $R^4$ are each a hydrogen atom;

$R^5$ and $R^6$ are each a hydrogen atom; and $R^7$ is (1) a 5- or 6-membered monocyclic aromatic heterocyclic group (e.g., pyrazolyl, triazolyl, imidazolyl, pyridazinyl) substituted by 1 to 3 substituents selected from (a) a $C_{1-6}$ alkyl group (e.g., methyl, ethyl, tert-butyl) optionally substituted by 1 to 3 substituents selected from a halogen atom (e.g., fluorine atom), a $C_{3-10}$ cycloalkyl group (e.g., cyclopropyl), a $C_{1-6}$ alkoxy group (e.g., methoxy), and a mono- or di-$C_{1-6}$ alkyl-carbamoyl group (e.g., dimethylcarbamoyl), (b) a $C_{3-10}$ cycloalkyl group (e.g., cyclopropyl), and (c) a 3- to 8-membered monocyclic non-aromatic heterocyclic group (e.g., tetrahydropyranyl), (2) a carbamoyl group substituted by 1 or 2 (preferably 1) substituents selected from (a) a $C_{1-6}$ alkyl group (e.g., methyl, ethyl, propyl, isopropyl, isobutyl, tert-butyl) optionally substituted by 1 to 3 substituents selected from (i) a halogen atom (e.g., fluorine atom), (ii) a $C_{3-10}$ cycloalkyl group (e.g., cyclopropyl) optionally substituted by 1 to 3 hydroxy groups, (iii) a mono- or di-$C_{1-6}$ alkyl-carbamoyl group (e.g., dimethylcarbamoyl), (iv) a $C_{1-6}$ alkoxy group (e.g., methoxy, ethoxy), (v) a hydroxy group, (vi) a 3- to 8-membered monocyclic non-aromatic heterocyclic group (e.g., oxetanyl, tetrahydrofuranyl, pyrrolidinyl, tetrahydropyranyl, morpholinyl) optionally substituted by one oxo group, and (vii) a $C_{1-6}$ alkylsulfonyl group (e.g., methylsulfonyl), (b) a $C_{3-10}$ cycloalkyl group (e.g., cyclopropyl, cyclobutyl, bicyclo[1.1.1]pentyl) optionally substituted by 1 to 3 substituents selected from a halogen atom (e.g., fluorine atom), an optionally halogenated $C_{1-6}$ alkyl group (e.g., methyl, difluoromethyl), and a cyano group, and (c) a 3- to 8-membered monocyclic non-aromatic heterocyclic group (e.g., oxetanyl, thietanyl, tetrahydrofuranyl, tetrahydropyranyl) optionally substituted by 1 to 3 substituents selected from a $C_{1-6}$ alkyl group (e.g., methyl), an oxo group and a hydroxy group, (3) an azetidin-1-ylcarbonyl group optionally substituted by 1 to 3 substituents selected from an optionally halogenated $C_{1-6}$ alkyl group (e.g., difluoromethyl), a hydroxy group and a $C_{1-6}$ alkoxy group (e.g., methoxy), (4) a $C_{1-6}$ alkyl group (e.g., methyl), or (5) a carboxy group.

[Compound I-3]

Compound (I) wherein $X^1$ is a CH or N;

$X^2$ is a $CR^{10}$ or N;

$R^{10}$ is a hydrogen atom or a halogen atom (e.g., fluorine atom);

$R^1$ and $R^2$ are each independently a hydrogen atom, a halogen atom (e.g., chlorine atom, fluorine atom), a $C_{1-6}$ alkyl group (e.g., methyl), or a $C_{1-6}$ alkoxy group (e.g., methoxy);

$R^3$ and $R^4$ are each a hydrogen atom;

$R^5$ and $R^6$ are each a hydrogen atom; and $R^7$ is (1) a 5- or 6-membered monocyclic aromatic heterocyclic group (e.g., pyrazolyl, triazolyl, imidazolyl, pyridazinyl) substituted by 1 to 3 substituents selected from (a) a $C_{1-6}$ alkyl group (e.g., methyl, ethyl) optionally substituted by 1 to 3 substituents selected from a $C_{3-10}$ cycloalkyl group (e.g., cyclopropyl) and a $C_{1-6}$ alkoxy group (e.g., methoxy), (b) a $C_{3-10}$ cycloalkyl group (e.g., cyclopropyl), and (c) a 3- to 8-membered monocyclic non-aromatic heterocyclic group (e.g., tetrahydropyranyl), (2) a carbamoyl group substituted by 1 or 2 (preferably 1) substituents selected from (a) a $C_{1-6}$ alkyl group (e.g., methyl, ethyl, propyl, isobutyl) optionally substituted by 1 to 3 substituents selected from (i) a $C_{3-10}$ cycloalkyl group (e.g., cyclopropyl) optionally substituted by 1 to 3 hydroxy groups, (ii) a mono- or di-$C_{1-6}$ alkyl-carbamoyl group (e.g., dimethylcarbamoyl), (iii) a $C_{1-6}$ alkoxy group (e.g., methoxy, ethoxy), (iv) a hydroxy group, (v) a 3- to 8-membered monocyclic non-aromatic heterocyclic group (e.g., oxetanyl, tetrahydrofuranyl, pyrrolidinyl) optionally substituted by one oxo group, and (vi) a $C_{1-6}$ alkylsulfonyl group (e.g., methylsulfonyl), (b) a $C_{3-10}$ cycloalkyl group (e.g., cyclopropyl, cyclobutyl) optionally substituted by 1 to 3 halogen atoms (e.g., fluorine atom), and (c) a 3- to 8-membered monocyclic non-aromatic heterocyclic group (e.g., oxetanyl, thietanyl, tetrahydrofuranyl) optionally substituted by 1 to 3 substituents selected from an $C_{1-6}$ alkyl group (e.g., methyl) and an oxo group, or (3) an azetidin-1-ylcarbonyl group optionally substituted by 1 to 3 $C_{1-6}$ alkoxy groups (e.g., methoxy).

[Compound I-4]

Compound (I) wherein $X^1$ is a CH or N;

$X^2$ is a $CR^{10}$ or N;

$R^{10}$ is a hydrogen atom or a halogen atom (e.g., fluorine atom);

$R^1$ and $R^2$ are each independently a halogen atom (e.g., chlorine atom) or a $C_{1-6}$ alkyl group (e.g., methyl);

$R^3$ and $R^4$ are each a hydrogen atom;

$R^5$ and $R^6$ are each a hydrogen atom; and $R^7$ is (1) a pyrazolyl group or a triazolyl group each substituted by 1 or 2 substituents selected from (a) a $C_{1-6}$ alkyl group (e.g., methyl, ethyl, tert-butyl) optionally substituted by 1 to 3 substituents selected from a halogen atom (e.g., fluorine atom), a $C_{3-10}$ cycloalkyl group (e.g., cyclopropyl), and a $C_{1-6}$ alkoxy group (e.g., methoxy), and (b) a 3- to 8-membered monocyclic non-aromatic heterocyclic group (e.g., tetrahydropyranyl), or (2) a carbamoyl group substituted by one substituent selected from (a) a $C_{1-6}$ alkyl group (e.g., methyl, ethyl, propyl) optionally substituted by 1 to 3 (preferably 1) substituents selected from a $C_{1-6}$ alkoxy group (e.g., methoxy, ethoxy) and a 3- to 8-membered monocyclic non-aromatic heterocyclic group (e.g., tetrahydrofuranyl), and (b) a $C_{3-10}$ cycloalkyl group (e.g., cyclopropyl).

[Compound I-5]

The aforementioned [Compound I-2] wherein $X^1$ is CH.

[Compound I-6]

Compound (I) wherein $X^1$ is N;

$X^2$ is $CR^{10}$ or N;

$R^{10}$ is a hydrogen atom or a halogen atom (e.g., fluorine atom);

$R^1$ and $R^2$ are each independently a halogen atom (e.g., chlorine atom) or a $C_{1-6}$ alkyl group (e.g., methyl);

$R^3$ and $R^4$ are each a hydrogen atom;

$R^5$ and $R^6$ are each a hydrogen atom; and $R^7$ is (1) a 5- or 6-membered monocyclic aromatic heterocyclic group (e.g., pyrazolyl, triazolyl) substituted by 1 to 3 $C_{1-6}$ alkyl groups (e.g., methyl), (2) a carbamoyl group substituted by 1 or 2 $C_{1-6}$ alkyl groups (e.g., methyl), or (3) a carboxy group.

[Compound I-7]

Compound (I) wherein $X^1$ is CH or N;

$X^2$ is $CR^{10}$ or N;

$R^{10}$ is a hydrogen atom or a halogen atom (e.g., fluorine atom);

$R^1$ is a halogen atom (e.g., fluorine atom, chlorine atom) or a $C_{1-6}$ alkyl group (e.g., methyl);

$R^2$ is a $C_{1-6}$ alkyl group (e.g., methyl) or a $C_{1-6}$ alkoxy group (e.g., methoxy);

$R^3$ and $R^4$ are each a hydrogen atom;

$R^5$ is a hydrogen atom;

$R^6$ is a hydrogen atom or a halogen atom (e.g., fluorine atom); and $R^7$ is a carbamoyl group substituted by 1 or 2 (preferably 1) substituents selected from (a) a $C_{1-6}$ alkyl group (e.g., methyl, ethyl, propyl, isopropyl, isobutyl, tert-butyl) optionally substituted by 1 to 3 substituents selected from (i) a halogen atom (e.g., fluorine atom), (ii) a $C_{3-10}$ cycloalkyl group (e.g., cyclopropyl) optionally substituted by 1 to 3 (preferably 1) hydroxy groups, (iii) a mono- or di-$C_{1-6}$ alkyl-carbamoyl group (e.g., dimethylcarbamoyl), (iv) a $C_{1-6}$ alkoxy group (e.g., methoxy, ethoxy), (v) a hydroxy group, (vi) a 3- to 8-membered monocyclic non-aromatic heterocyclic group (e.g., oxetanyl, tetrahydrofuranyl, pyrrolidinyl, tetrahydropyranyl, morpholinyl) optionally substituted by one oxo group, and (vii) a $C_{1-6}$ alkylsulfonyl group (e.g., methylsulfonyl), (b) a $C_{3-10}$ cycloalkyl group (e.g., cyclopropyl, cyclobutyl, bicyclo[1.1.1]pentyl) optionally substituted by 1 to 3 (preferably 1 or 2) substituents selected from a halogen atom (e.g., fluorine atom), an optionally halogenated $C_{1-6}$ alkyl group (e.g., methyl, difluoromethyl) and a cyano group, and (c) a 3- to 8-membered monocyclic non-aromatic heterocyclic group (e.g., oxetanyl, thietanyl, tetrahydrofuranyl, tetrahydropyranyl) optionally substituted by 1 to 3 (preferably 1 or 2) substituents selected from a $C_{1-6}$ alkyl group (e.g., methyl), an oxo group and a hydroxy group.

[Compound I-8]

Compound (I) wherein $X^1$ is CH or N;

$X^2$ is $CR^{10}$ or N;

$R^{10}$ is a hydrogen atom or a halogen atom (e.g., fluorine atom);

$R^1$ is a halogen atom (e.g., fluorine atom, chlorine atom) or a $C_{1-6}$ alkyl group (e.g., methyl);

$R^2$ is a $C_{1-6}$ alkyl group (e.g., methyl) or a $C_{1-6}$ alkoxy group (e.g., methoxy);

$R^3$, $R^4$, $R^5$ and $R^6$ are each a hydrogen atom; and $R^7$ is a 5- or 6-membered monocyclic aromatic heterocyclic group selected from

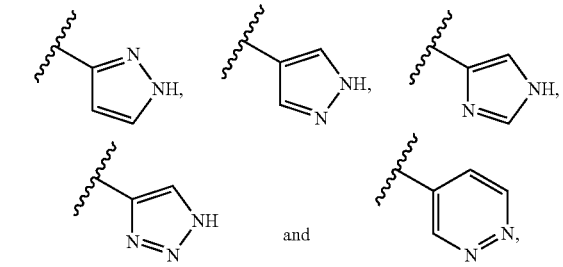

and which is substituted by 1 to 3 (preferably 1 or 2) substituents selected from (a) a $C_{1-6}$ alkyl group (e.g., methyl, ethyl, tert-butyl) optionally substituted by 1 to 3 substituents selected from a halogen atom (e.g., fluorine atom), a $C_{3-10}$ cycloalkyl group (e.g., cyclopropyl), a $C_{1-6}$ alkoxy group (e.g., methoxy), and a mono- or di-$C_{1-6}$ alkyl-carbamoyl group (e.g., dimethylcarbamoyl), (b) a $C_{3-10}$ cycloalkyl group (e.g., cyclopropyl), and (c) a 3- to 8-membered monocyclic non-aromatic heterocyclic group (e.g., tetrahydropyranyl).

Preferable specific examples of the compound represented by the formula (I) include the compounds of Examples 1-94.

When compound (I) is in the form of a salt, examples of such salt include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, examples of a preferable pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. compound (I) may be a compound labeled or substituted with an isotope (e.g., $^2$H, $^3$H, $^{11}$C, $^{14}$C, $^{18}$F, $^{35}$S, $^{125}$I). A compound labeled with or substituted by an isotope can be used, for example, as a tracer used for Positron Emission Tomography (PET) (PET tracer), and is useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are also encompassed in compound (I) of the present invention.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature—300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide and the like;
organic bases: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5, 6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride, a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining an alkyl halide form from alcohol by reacting with triphenylphosphine and carbon tetrachloride or carbon tetrabromide, and the like may be used. Alternatively, a method of synthesizing an alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonic acid esterification reaction is performed in each step, examples of the sulfonylating agent to be used include methanesulfonyl chloride, p-toluenesulfonyl chloride, methanesulfonic anhydride, p-toluenesulfonic anhydride and the like.

When hydrolysis reaction is performed in each step, an acid or a base is used as the reagent. In addition, when acid hydrolysis reaction of tert-butyl ester is performed, formic acid, triethylsilane and the like are sometimes added to reductively trap the by-produced tert-butyl cation.

When a dehydration reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Compound (I) can be produced by the method shown in the following schemes or a method analogous thereto or the method described in Examples.

Compound (I) wherein $X^1$ is CH, i.e., compound (IA), can be produced from compound (1) by the following method.

Compound (8) can be produced by a coupling reaction of compound (7) and bis(pinacolato)diboron in the presence of a metal catalyst.

Compound (9) can be produced by a coupling reaction of compound (8) and compound (6) in the presence of a metal catalyst.

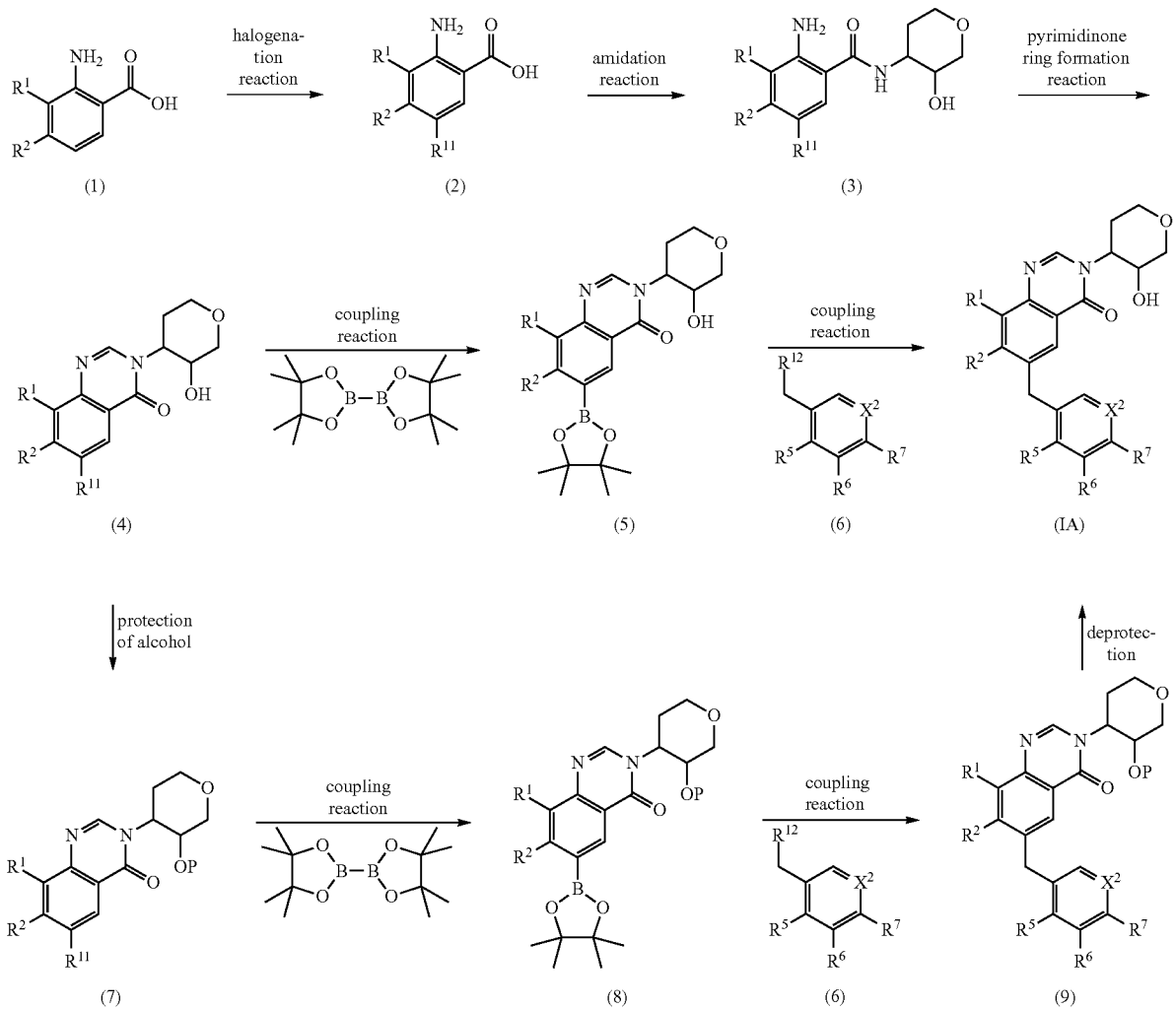

In the reaction formulas, $R^{11}$ and $R^{12}$ are each a halogen atom, P is an alcohol-protecting group and $R^1$, $R^2$, $R^5$ to $R^7$ and $X^2$ mean the same as above.

Compound (2) can be produced by halogenation of compound (1) and a halogenating agent such as bromine and the like.

Compound (3) can be produced by an amidation reaction of compound (2) and amines.

Compound (4) can be produced by a pyrimidinone ring formation reaction of compound (3) and N,N-dimethylformamide dimethyl acetal.

Compound (5) can be produced by a coupling reaction of compound (4) and bis(pinacolato)diboron in the presence of a metal catalyst.

Compound (7) can be produced by protecting alcohol of compound (4).

Compound (IA) can be produced by a coupling reaction of compound (5) and compound (6) in the presence of a metal catalyst, or deprotection of the alcohol-protecting group of compound (9).

Compound (I) wherein $X^1$ is N, i.e., compound (II), can be produced from compound (3) by the following method.

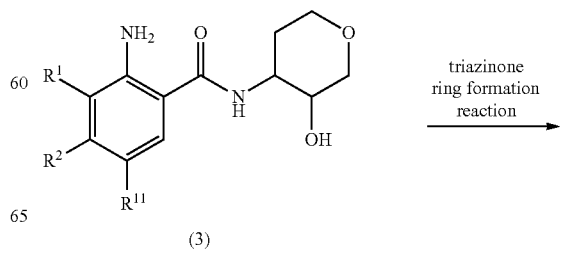

-continued

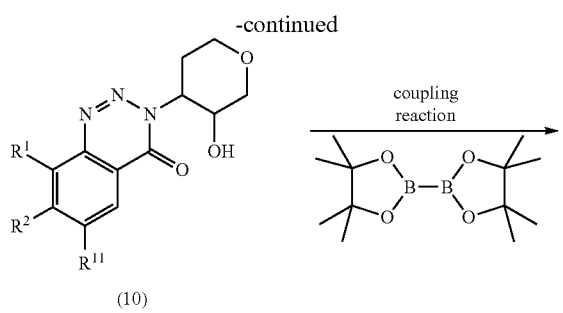

(10)

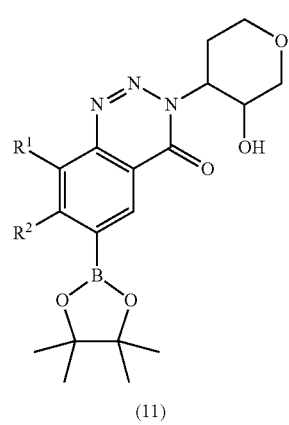

(11)

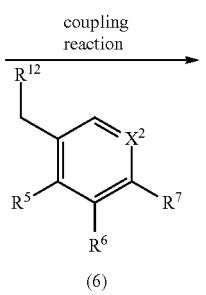

(6)

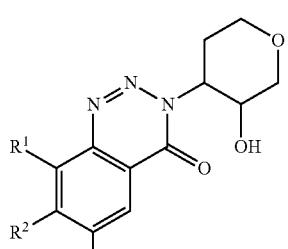

(II)

In the reaction formulas, $R^1$, $R^2$, $R^5$ to $R^7$, $R^{11}$, $R^{12}$ and $X^2$ mean the same as above.

Compound (10) can be produced by a triazinone ring formation reaction of compound (3) and sodium nitrite.

Compound (11) can be produced by a coupling reaction of compound (10) and bis(pinacolato)diboron in the presence of a metal catalyst.

Compound (II) can be produced by a coupling reaction of compound (11) and compound (6) in the presence of a metal catalyst.

Of compounds (IA) and (II), compound (13) wherein $R^7$ is a carboxy group and compound (14) wherein $R^7$ is an optionally substituted carbamoyl group can be produced from compound (5) or compound (11) by the following method.

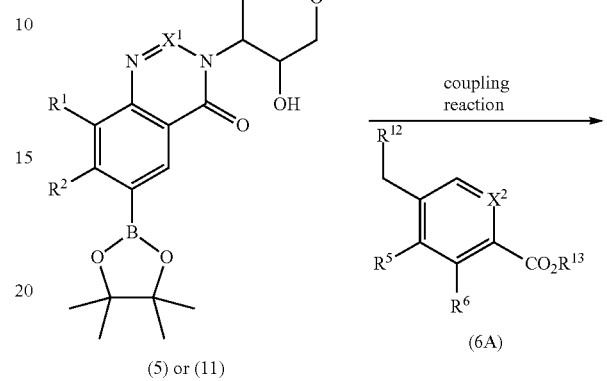

(5) or (11)                (6A)

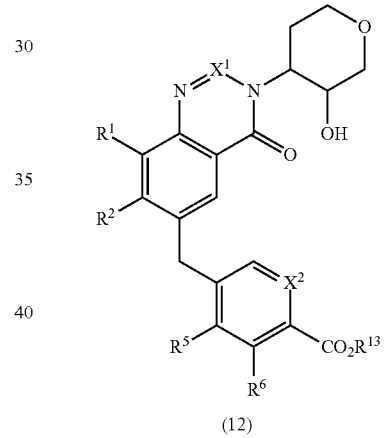

(12)

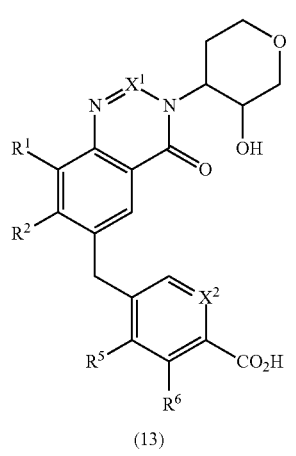

(13)

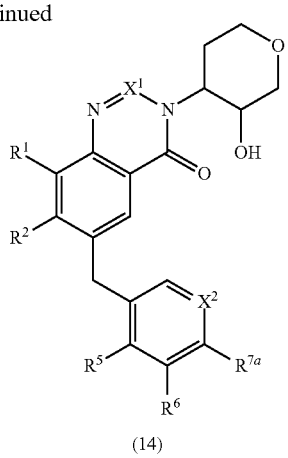

(14)

In the reaction formulas, $R^{13}$ is a $C_{1-6}$ alkyl group, $R^{7a}$ is an optionally substituted carbamoyl group, and $R^1$, $R^2$, $R^5$, $R^6$, $R^{12}$, $X^1$ and $X^2$ mean the same as above.

Compound (12) can be produced by a coupling reaction of compound (5) or compound (11) and compound (6A) in the presence of a metal catalyst.

Compound (13) can be produced by hydrolysis of compound (12).

Compound (14) can be produced by an amidation reaction of compound (13) and amines.

Of compounds (IA) and (II), compound (18) wherein $R^7$ is an optionally substituted pyrazolyl group can also be produced from compound (5) or compound (11) by the following method.

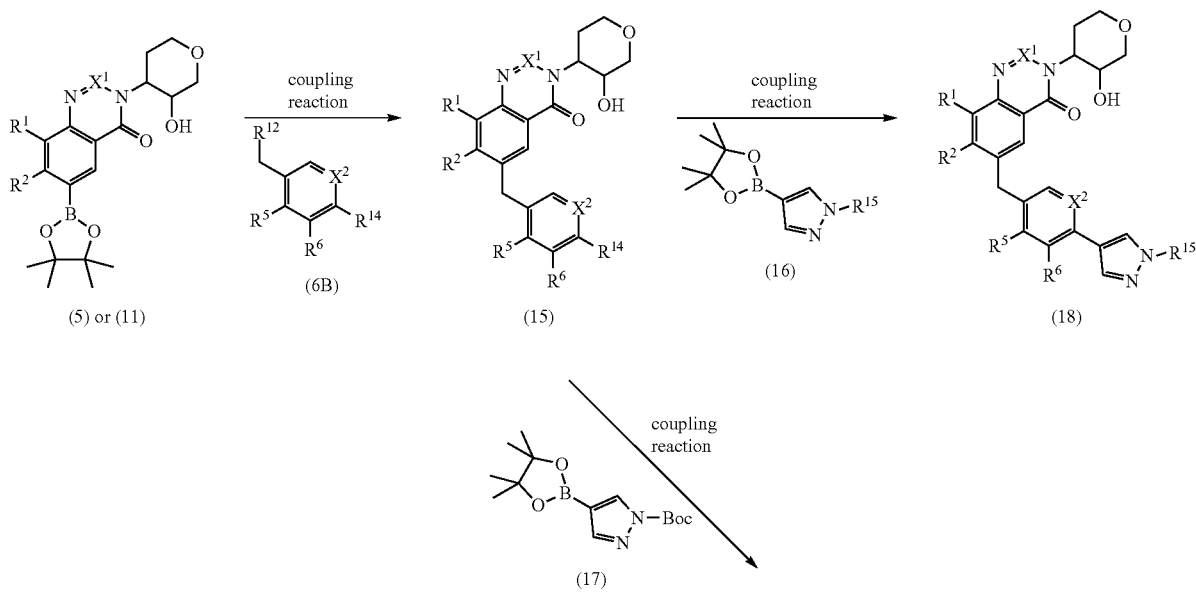

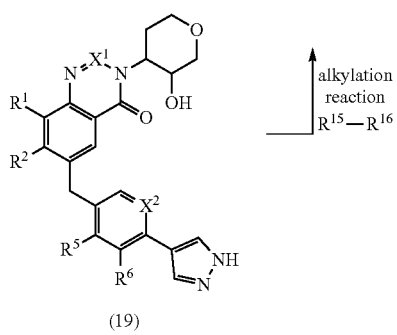

In the reaction formulas, $R^{14}$ and $R^{16}$ are each a halogen atom, $R^{15}$ is an optionally substituted hydrocarbon group or optionally substituted heterocyclic group and $R^1$, $R^2$, $R^5$, $R^6$, $R^{12}$, $X^1$ and $X^2$ mean the same as above.

Compound (15) can be produced by a coupling reaction of compound (5) or compound (11) and compound (6B) in the presence of a metal catalyst.

Compound (18) can be produced by a coupling reaction of compound (15) and compound (16) in the presence of a metal catalyst.

Compound (19) can be produced by a coupling reaction of compound (15) and compound (17) in the presence of a metal catalyst.

Compound (18) can be produced by an alkylation reaction of compound (19) and $R^{15}$-$R^{16}$ in the presence of a base.

Of compounds (I), compound (23) wherein one of $R^3$ and $R^4$ is a halogen atom and the other is a hydrogen atom, and compound (25) wherein one of $R^3$ and $R^4$ is an optionally substituted $C_{1-6}$ alkoxy group and the other is a hydrogen atom can be produced from compound (20) by the following method.

In the reaction formulas, $R^{17}$ and $R^{18}$ are each a halogen atom, $R^{19}$ is an optionally substituted $C_{1-6}$ alkyl group, and P, $R^1$, $R^2$, $R^5$, R, $R^7$, $R^{11}$, $X^1$ and $X^2$ mean the same as above.

Compound (22) can be produced by a Grignard reaction of compound (20) and compound (21).

Compound (23) can be produced by halogenating the hydroxy group of compound (22) and deprotection of the alcohol-protecting group. As a halogenating agent, a fluorinating agent such as (diethylamino)sulfur trifluoride and the like, and the like can be mentioned besides the aforementioned reagents.

Compound (25) can be produced by alkylating the hydroxy group of compound (22) with alkyl halide (24) and deprotection of the alcohol-protecting group.

Of compounds (I), compound (28) wherein one of $R^3$ and $R^4$ is an optionally substituted $C_{1-6}$ alkyl group and the other is a hydrogen atom can be produced from compound (20) by the following method.

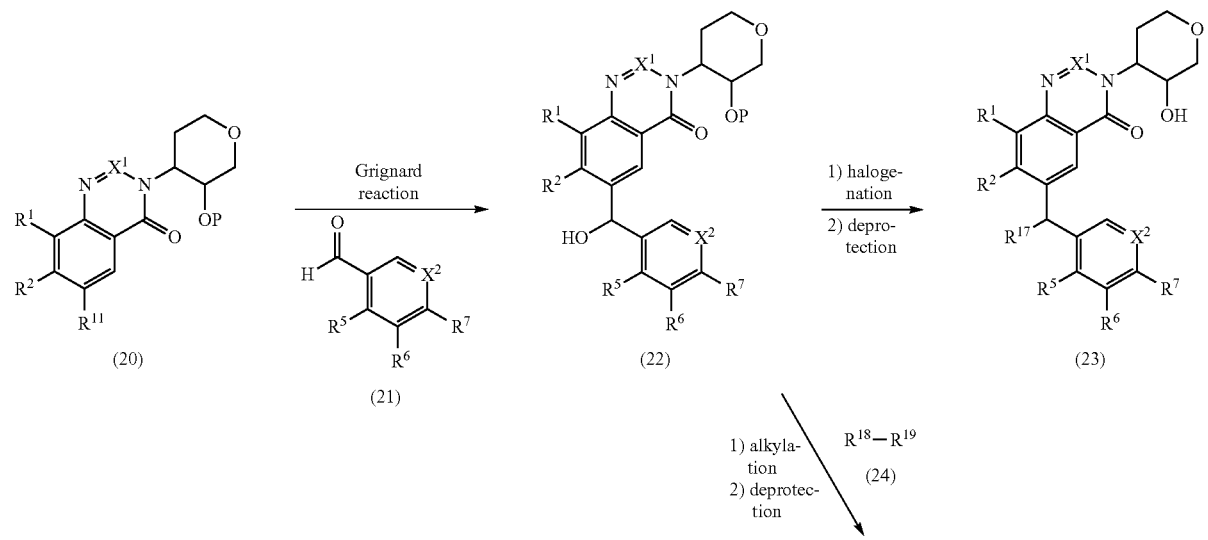

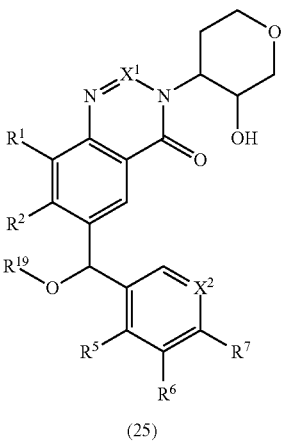

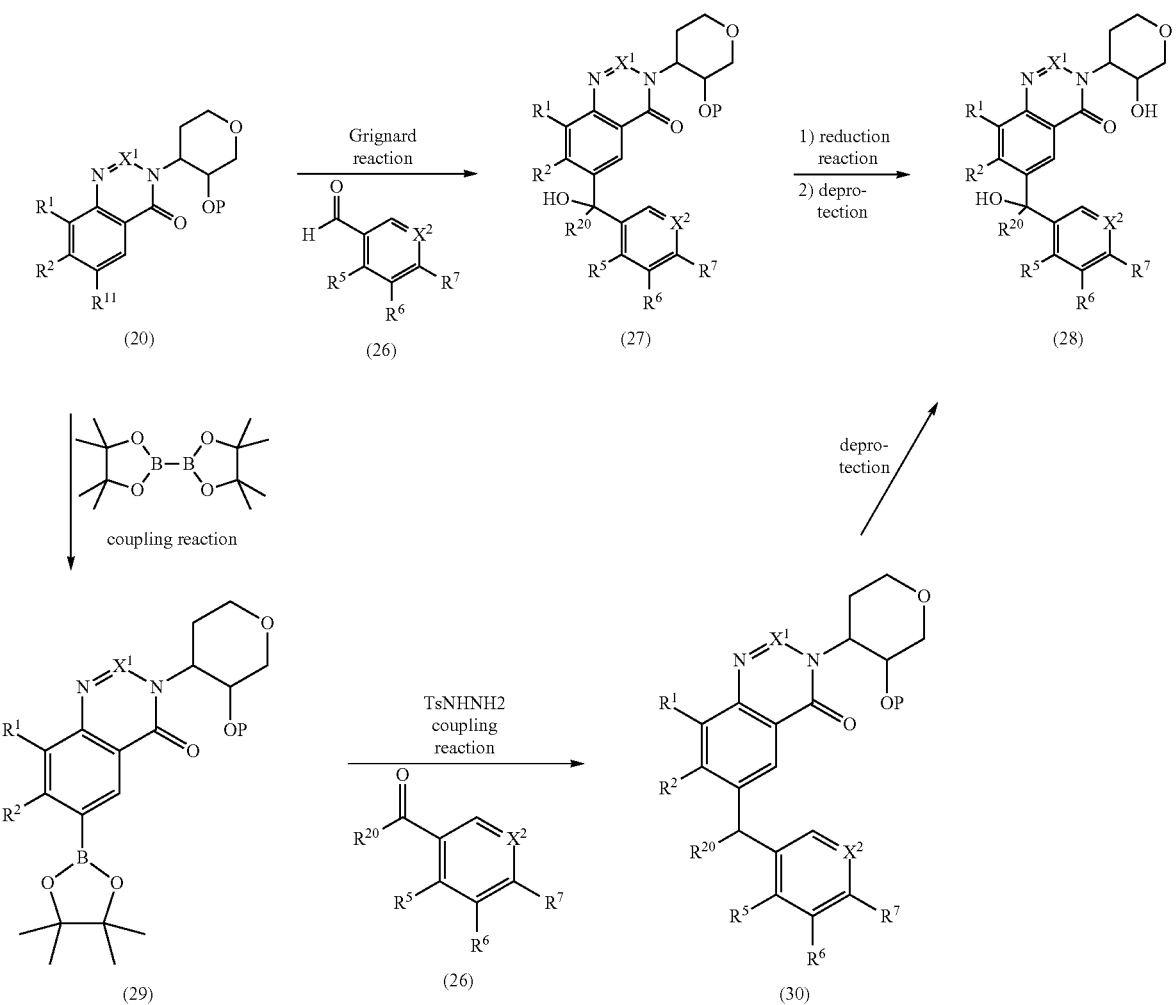

In the reaction formulas, $R^{20}$ is an optionally substituted $C_{1-6}$ alkyl group, and P, $R^1$, $R^2$, $R^5$, $R^6$, $R^7$, $R^{11}$, $X^1$ and $X^2$ mean the same as above.

Compound (27) can be produced by a Grignard reaction of compound (20) and compound (26).

Compound (28) can be produced by reducing the hydroxy group of compound (27) and deprotection of the alcohol-protecting group.

Compound (29) can be produced by a coupling reaction of compound (20) and bis(pinacolato)diboron in the presence of a metal catalyst.

Compound (30) can be produced by a coupling reaction of compound (29) and compound (26) in the presence of p-toluenesulfonyl hydrazide and an inorganic base according to the method described in (document) Tetrahedron, 73, 785-793 (2017). As the inorganic base, potassium carbonate, potassium phosphate and the like can be mentioned.

Compound (28) can be produced by deprotection of the alcohol-protecting group of compound (30).

Compound (1), compound (2), amines, compound (6), compound (6A), compound (6B), compound (16), compound (17), compound (20), compound (21), compound (26), $R^{15}$-$R^{16}$, $R^{18}$-$R^{19}$, N,N-dimethylformamide dimethyl acetal and sodium nitrite used as starting materials for the production of Compounds (IA) and (II) may be commercially available products or can be produced by a method known per se.

When compounds (IA) and (II) have an optical isomer, a stereoisomer, a regioisomer or a rotamer, these are also encompassed in compound (I), and can be obtained as a single product according to synthesis and separation methods known per se. For example, when compounds (IA) and (II) contain an optical isomer, an optical isomer resolved from these compounds is also encompassed in compounds (IA) and (II).

The optical isomer can be produced according to a method known per se. To be specific, an optically active synthetic intermediate is used, or the final racemate product is subjected to optical resolution according to a conventional method to give an optical isomer.

For example, the method of optical resolution may be a method known per se, such as a fractional recrystallization method, a chiral column method, a diastereomer method etc.

1) Fractional Recrystallization Method

A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series manufactured by Daicel Corporation and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis reaction and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis reaction.

When compound (I) is obtained as a free compound, the compound can be converted to an objective salt according to a method known per se or a method analogous thereto. Conversely, when it is obtained as a salt, the salt can be converted to a free form or other objective salt by a method known per se or a method analogous thereto.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include
a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, t-butylation and the like);
a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like);
a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be used for the prophylaxis or treatment of diseases, for example, constipation, for example, neurogenic constipation (constipation associated with diseases such as Parkinson's disease, multiple sclerosis, spinal cord injury, Alzheimer's disease, Hirschsprung's syndrome, Chagas' disease, and the like), idiopathic constipation, functional constipation, flaccid constipation, irritable bowel syndrome with constipation, constipation possibly complicated by other disease (Parkinson's disease, spinal cord injury, multiple sclerosis, etc.), age-related constipation, various drug-induced constipation (opioid agonist-induced constipation and the like), primary chronic constipation, drug-induced constipation (opioid, anticholinergic agent, calcium antagonist, anticancer agent, heavy metal toxicosis, and the like), constipation associated with underlying diseases such as endocrine diseases or metabolic abnormality (hypopituitarism, hypothyroidism, pheochromocytoma, and the like), muscle abnormalities disease (familial visceral skeletal muscle atrophy, scleroderma, amyloidosis, progressive systemic sclerosis, and the like), metabolic diseases (diabetes, porphyria, uremia, hypokalemia, hypercalcemia, and the like) and the like, and gastric hypomotility such as gastroparalysis and the like, post-operative gastrointestinal paralysis, upper gastrointestinal motility disorder and discomfort, nausea, vomiting, erosive esophagitis, gastric ulcer, duodenal ulcer, antiinflammatory agents (non-steroidal antiinflammatory agents)-induced gastrointestinal disorder, dysuria, bladder functional disorder and the like in mammals (e.g., mouse, rat, hamster, rabbit, cat, dog, bovine, sheep, monkey, human etc.).

Since compound (I) may have a cholinergic muscarinic M1 receptor positive allosteric modulator activity, it is expected to provide an excellent prophylactic or therapeutic effect for the above-mentioned diseases.

Generally, it is desirable that the therapeutic drugs for constipation exhibit effect promptly after administration and then the effect disappears quickly. Compound (I) is expected to show superior pharmacokinetics as a therapeutic drug for constipation and may be expected to exhibit effect within, for example, 3 hr after administration, preferably 2 hr after administration, further preferably 1 hr after administration, and the effect may be expected to disappear quickly thereafter.

Cholinergic muscarinic M1 receptor is known to express in the brain and gastrointestinal nerve plexus. Compound (I) is expected to show low central nervous system permeability, function efficiently in periphery and show excellent effect as a therapeutic drug for constipation. Regarding central nervous system permeability, for example, corrected efflux ratio of MDR1 in MDR1 membrane permeability test is preferably not less than 2.0, more preferably not less than 3.0, and furthermore preferably not less than 5.0.

Since compound (I) may be expected to be excellent in solubility in water, the Japanese Pharmacopoeia dissolution test 2nd fluid, or the Japanese Pharmacopoeia disintegration test 2nd fluid, excellent in pharmacokinetics (e.g., plasma drug half-life, metabolic stability, CYP inhibition), show low toxicity (e.g., more excellent as a medicament in terms of acute toxicity, chronic toxicity, genetic toxicity, reproductive toxicity, cardiotoxicity, drug interaction, carcinogenicity, phototoxicity and the like), and may also have excellent properties as a pharmaceutical product such as a few side effects and the like, it can be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

A medicament containing compound (I) (sometimes to be abbreviated as "medicament of the present invention" in the present specification) may have any form (preparation form) of a solid preparation such as powder, granule, tablet, capsule, orally disintegrable film and the like, or a liquid agent such as syrup, emulsion, injection and the like.

The medicament of the present invention may be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation can be produced according to the method described in JP-A-9-263545.

In the medicament of the present invention, the content of compound (I) varies depending on the form of the preparation, but is generally 0.01 to 100% by weight, preferably 0.1 to 50% by weight, more preferably 0.5 to 20% by weight, as the amount of compound (I) relative to the whole preparation (whole medicament).

Compound (I) may be used alone or in admixture with a suitable, pharmacologically acceptable carrier, for example, excipients (e.g., starch, lactose, white soft sugar, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and administered orally or parenterally. When compound (I) is formed as a preparation for topical administration, it can also be directly administered to the affected part of an articular disease. In this case, an injection is preferable. compound (I) can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound together with vegetable oil such as sesame oil, corn oil and the like or a mixture thereof with a phospholipid such as lecithin and the like, or medium-chain fatty acid triglyceride (e.g., miglyol 812 etc.) to give an injection to be actually used.

The dose of compound (I) varies depending on the subject of administration, administration route and symptoms and is not particularly limited. For example, for oral administration to adult patients (body weight adult 40 to 80 kg, for example, 60 kg) with constipation, the dose may be, for example, 0.001 to 1000 mg/kg body weight/day, preferably 0.01 to 100 mg/kg body weight/day, more preferably 0.1 to 10 mg/kg body weight/day, as compound (I). This amount may be administered in one to three portions per day.

The medicament of the present invention may be able to use the compound (I) solely or as a pharmaceutical composition of compound (I) mixed with a pharmacologically acceptable carrier according to a method known per se (e.g., the method described in the Japanese Pharmacopoeia etc.) as the production method of a pharmaceutical preparation. The medicament of the present invention may be administered safely in the form of, for example, a pharmaceutical composition such as tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal, lesion and the like).

As the aforementioned "pharmacologically acceptable carrier", various organic or inorganic carriers conventionally used as preparation materials (starting materials) may be used. For example, excipient, lubricant, binder, disintegrant and the like may be used for solid preparations, and solvent, solubilizing agent, suspending agent, isotonic agent, buffer, soothing agent and the like may be used for liquid preparations. Where necessary, preparation additives such as preservative, antioxidant, colorant, sweetening agent and the like may also be used.

Examples of the excipient include lactose, white soft sugar, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white soft sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphate salts, acetate salts, carbonate salts, citrate salts and the like.

Examples of the soothing agent include benzyl alcohol and the like.

Examples of the preservative include p-oxybenzoate esters, chlorobutanol, benzyl alcohol, phenylethyl alcohol, dehydroacetic acid, sorbic acid and the like.

Examples of the antioxidant include sulfite salts, ascorbic acid, α-tocopherol and the like.

While the pharmaceutical composition varies according to the dosage form, administration method, carrier and the like, it may be produced according to a conventional method by adding compound (I) in a proportion of generally 0.01-100% (w/w), preferably 0.1-95% (w/w), of the total amount of the preparation.

Compound (I) may be used in combination with other active ingredients (hereinafter to be abbreviated as concomitant drug).

Examples of the concomitant drug include the following.

Prokinetic agent (cholinesterase inhibitor (neostigmine, physostigmine etc.), 5-HT$_4$ agonist, ghrelin agonist (capromorelin etc.), motilin receptor agonist (camicinal, erythromycin etc.), opioid antagonist (naltrexone, naloxegol etc.)), intestinal water secretion promoter (guanylate cyclase C agonist (linaclotide etc.), chloride channel 2 opener (lubiprostone etc.), sodium/proton exchanger 3 inhibitor (tenapanor etc.)), anti-constipation drug (sennoside, magnesium oxide, magnesium hydroxide, bisacodyl, polycarbophil calcium, laxative sugars (lactulose etc.), laxoberon, crude drug having an anti-constipation action (psyllium etc.) etc.), benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-HT$_{1A}$ agonist (buspirone hydrochloride, tandospirone citrate, osemozotan hydrochloride etc.), 5-HT$_3$ antagonist (cyamemazine etc.), heart non-selective β inhibitor (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (aprepitant, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT$_{2A}$ antagonist, 5-HTA inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autisma, therapeutic drug for chronic fatigue syndrome, therapeutic drug for convulsion, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, combination of those drugs etc.), therapeutic drug for Parkinson's disease dementia (rivastigmine), therapeutic drug for Lewy body dementia (donepezil), therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for behavior abnormalities or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anticancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining compound (I) and a concomitant drug, a superior effect such as (1) the dose may be reduced as compared to single administration of the compound (I) or a concomitant drug,
(2) the drug to be combined with the compound (I) may be selected according to the condition of patients (mild case, severe case and the like),
(3) the period of treatment may be set longer by selecting a concomitant drug having different action and mechanism from the compound (I),
(4) a sustained treatment effect may be designed by selecting a concomitant drug having different action and mechanism from the compound (I),
(5) a synergistic effect may be afforded by a combined use of the compound (I) and a concomitant drug, and the like, can be achieved.

Hereinafter compound (I) and a concomitant drug used in combination are referred to as the "combination agent of the present invention".

When using the combination agent of the present invention, the administration time of compound (I) and the concomitant drug is not restricted, and compound (I) or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that compound (I) and the concomitant drug are combined in administration. Examples of the administration mode include the following methods:
(1) administration of a single preparation obtained by simultaneously processing compound (I) and the concomitant drug,
(2) simultaneous administration of two kinds of preparations of compound (I) and the concomitant drug, which have been separately produced, by the same administration route, (3) administration of two kinds of preparations of compound (I) and the concomitant drug, which have been separately produced, by the same administration route in a staggered manner, (4) simultaneous administration of two kinds of preparations of compound (I) and the concomitant drug, which have been separately produced, by different administration routes, (5) administration of two kinds of preparations of compound (I) and the concomitant drug, which have been separately produced, by different administration routes in a staggered manner (e.g., administration in the order of compound (I) and the concomitant drug, or in the reverse order) and the like.

The combination agent of the present invention can be expected to show low toxicity. For example, compound (I) or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions may be administered safely orally or non-orally (e.g., topical, rectal, intravenous administration etc.). Injection may be administered intravenously, intramuscularly, subcutaneously, or by intraorgan administration or directly to the lesion.

As the pharmacologically acceptable carriers that may be used for the production of a combination agent in the present invention, various organic or inorganic carrier substances conventionally used as preparation materials may be used. For solid preparations, for example, excipient, lubricant, binder and disintegrant may be used. For liquid preparations, for example, solvent, solubilizing agent, suspending agent, isotonic agent, buffering agent, soothing agent and the like may be used. Where necessary, a suitable amount of conventional preservative, antioxidant, colorant, sweetening agent, adsorbent, wetting agent and the like may be used as appropriate.

Examples of the excipient include lactose, white soft sugar, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white soft sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphate salts, acetate salts, carbonate salts, citrate salts and the like.

Examples of the soothing agent include benzyl alcohol and the like.

Examples of the preservative include p-oxybenzoate esters, chlorobutanol, benzyl alcohol, phenylethyl alcohol, dehydroacetic acid, sorbic acid and the like.

Examples of the antioxidant include sulfite salts, ascorbic acid, α-tocopherol and the like.

The mixing ratio of compound (I) to the concomitant drug in the combination agent of the present invention can be appropriately selected depending on an administration subject, administration route, diseases and the like.

For example, the content of compound (I) in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of the concomitant drug in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of additives such as a carrier and the like in the combination agent of the present invention differs depending on the form of a preparation, and usually from about 1 to 99.99 wt %, preferably from about 10 to 90 wt %, based on the whole preparation.

When compound (I) and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

Elution in column chromatography in the Examples was performed under observation by TLC (Thin Layer Chromatography) unless particularly indicated. In the TLC observation, 60 $F_{254}$ manufactured by Merck was used as a TLC plate, and the solvent used as an eluent in the column chromatography was used as an elution solvent. For detection, a UV detector was employed. In silica gel column chromatography, the indication of NH means use of aminopropylsilane-bonded silica gel, and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio of elution solvents is, unless otherwise specified, a volume mixing ratio.

For the analysis of $^1$H NMR, ACD/SpecManager (trade name) software and the like were used. Very mild peaks for protons of a hydroxy group, an amino group and the like may not be described.

MS was measured by LC/MS. As ionization method, ESI method or APCI method was used. The data indicates those found. Generally, molecular ion peaks are observed but may sometimes be observed as a fragment ion. In the case of a salt, generally, a molecular ion peak or a fragment ion peak of a free form is observed.

The unit of the sample concentration (c) by optical rotation ($[\alpha]_D$) is g/100 mL.

Elemental analytical value (Anal.) shows calculated value (Calcd) and measured value (Found).

The peak in powder X-ray diffraction in the Examples means a peak measured using Cu Kα ray as a radiation source and Ultima IV (Rigaku Corporation, Japan) at room temperature. The measurement conditions are as follows.

Electric pressure/Electric current: 40 kV/50 mA
Scan speed: 6 degree/min
Scan range of 2 Theta: 2-35 degree
The crystallinity by powder X-ray diffraction in the Examples was calculated by the Hermans method.

In Examples, the following abbreviations are used.
mp: melting point
MS: mass spectrum
M: mol concentration
N: normality
CDCl$_3$: deuterochloroform
DMSO-d$_6$: hexadeuterodimethyl sulfoxide
CD$_3$OD: tetradeuteromethanol
$^1$H NMR: proton nuclear magnetic resonance
LC/MS: liquid chromatography mass spectrometer
ESI: electrospray ionization
APCI: atmospheric pressure chemical ionization
AIBN: azobisisobutyronitrile
DIPEA: N,N-diisopropylethylamine
DMA: N,N-dimethylacetamide
DME: dimethoxyethane
DMF: N,N-dimethylformamide
DMSO: dimethyl sulfoxide
EtOH: ethanol
HATU: O-(7-azabenzotriazol-1-yl)-N,N,N',N'-tetramethyluronium hexafluorophosphate
IPE: diisopropyl ether
MeOH: methanol
MEK: methyl ethyl ketone
NBS: N-bromosuccinimide
NCS: N-chlorosuccinimide
PdCl$_2$ (Amphos)$_2$: bis(di-tert-butyl(4-dimethylaminophenyl)phosphine)dichloropalladium(II)
PdCl$_2$(dppf): 1,1'-bis(diphenylphosphino)ferrocene-palladium(II) dichloride
Pd(PPh$_3$)$_2$Cl$_2$: bis(triphenylphosphine) palladium(II) dichloride
TEA: triethylamine
TFA: trifluoroacetic acid
THF: tetrahydrofuran Example 1

1,5-anhydro-2,3-dideoxy-3-(7,8-dimethyl-6-((6-(1-methyl-1H-pyrazol-3-yl)pyridin-3-yl)methyl)-4-oxoquinazolin-3(4H)-yl)-L-threo-pentitol A) 2-amino-5-bromo-3,4-dimethylbenzoic acid To a mixture of 2-amino-3,4-dimethylbenzoic acid (10 g) and DMSO (100 mL) was added hydrobromic acid (48% v/v, 35 mL) at 0° C., and the mixture was stirred at room temperature for 20 hr. To the reaction mixture was added water (150 mL) at 0° C. and the mixture was stirred. The precipitate was collected by filtration, washed with water and dried to give the title compound (13.23 g).

MS, found: 244.1, 246.0.

B) 3-((2-amino-5-bromo-3,4-dimethylbenzoyl)amino)-1,5-anhydro-2,3-dideoxy-L-threo-pentitol To a mixture of 2-amino-5-bromo-3,4-dimethylbenzoic acid (10 g), 3-amino-1,5-anhydro-2,3-dideoxy-L-threo-pentitol hydrochloride (6.29 g), HATU (18.69 g) and DMF (100 mL) was added TEA (14.28 mL) at room temperature, and the mixture was stirred overnight. To the reaction mixture were added water and saturated aqueous sodium hydrogen carbonate solution, and the mixture was extracted with ethyl acetate. The aqueous layer was extracted with ethyl acetate/ THF. The organic layer was washed with water and saturated brine, dried over anhydrous sodium sulfate and concentrated under-reduced pressure. The residue was crystallized from ethyl acetate/IPE and the precipitate was collected by filtration and washed with IPE to give the title compound (14.19 g).

MS, found: 343.1, 345.1.

C) 1,5-anhydro-3-(6-bromo-7,8-dimethyl-4-oxoquinazolin-3(4H)-yl)-2,3-dideoxy-L-threo-pentitol A mixture of 3-((2-amino-5-bromo-3,4-dimethylbenzoyl) amino)-1,5-anhydro-2,3-dideoxy-L-threo-pentitol (14.19 g) and N,N-dimethylformamide dimethyl acetal (71.8 mL) was stirred at 90° C. under a nitrogen atmosphere for 3 hr. After cooling to room temperature, tert-butyl methyl ether (50 mL) was added, and the reaction mixture was stirred. The precipitate was collected by filtration and washed with tert-butyl methyl ether to give the title compound (11.0 g).

MS, found: 353.1, 355.1.

D) 1,5-anhydro-2,3-dideoxy-3-(7,8-dimethyl-4-oxo-6-(4,4,5,5-tetramethyl-1,3,2-dioxaborolan-2-yl)quinazolin-3(4H)-yl)-L-threo-pentitol To a mixture of 1,5-anhydro-3-(6-bromo-7,8-dimethyl-4-oxoquinazolin-3(4H)-yl)-2,3-dideoxy-L-threo-pentitol (5.00 g), bis(pinacolato)diboron (7.19 g), potassium acetate (6.95 g) and toluene (100 mL) was added Pd(PPh$_3$)$_2$Cl$_2$ (0.497 g), and the mixture was stirred under an argon atmosphere at 100° C. overnight. The insoluble material was filtered off, and the filtrate was concentrated under reduced pressure. The residue was purified by silica gel column chromatography (Diol, ethyl acetate/hexane) to give the title compound (7.56 g). The compound was used in the next step without further purification.

MS: [M+H]$^+$ 401.2.

E) 6-(1-methyl-1H-pyrazol-3-yl)nicotinaldehyde

To a mixture of 6-chloronicotinaldehyde (20.0 g), 1-methyl-3-(4,4,5,5-tetramethyl-1,3,2-dioxaborolan-2-yl)-1H-pyrazole (32.32 g), potassium carbonate (38.99 g), DME (400 mL) and water (40 mL) was added PdCl$_2$(dppf) dichloromethane adduct (3.45 g) at room temperature. Under an argon atmosphere, the reaction mixture was stirred overnight at 90° C., diluted with ethyl acetate at room temperature, and added to water. The organic layer was washed with water and saturated brine, and dried over anhydrous sodium sulfate and the solvent was evaporated under reduced pressure. The residue was purified by silica gel column chromatography (ethyl acetate/hexane) to give the title compound (25.0 g).

$^1$H NMR (400 MHz, CDCl$_3$) δ 4.01 (3H, s), 6.97 (1H, d, J=2.45 Hz), 7.45 (1H, d, J=2.45 Hz), 8.08 (1H, d, J=8.4 Hz), 8.19 (1H, dd, J=8.31, 1.96 Hz), 9.05 (1H, d, J=1.47 Hz), 10.09 (1H, s).

F) (6-(1-methyl-1H-pyrazol-3-yl)pyridin-3-yl) methanol

To a solution of 6-(1-methyl-1H-pyrazol-3-yl)nicotinaldehyde (25.0 g) in MeOH (375 mL) was added sodium borohydride (10.16 g) at 0° C., and the mixture was stirred at room temperature for 16 hr. To the reaction mixture was added water, and the mixture was extracted with ethyl acetate. The organic layer was washed with saturated brine and dried over anhydrous magnesium sulfate. The solvent was evaporated under reduced pressure. The residue was purified by silica gel column chromatography (ethyl acetate/ hexane) to give the title compound (18.0 g).

$^1$H NMR (500 MHz, CDCl$_3$) δ 1.81 (1H, brs), 3.98 (3H, s), 4.74 (2H, d, J=4.88 Hz), 6.85 (1H, d, J=2.44 Hz), 7.41 (1H, d, J=2.44 Hz), 7.74 (1H, dd, J=8.09, 2.29 Hz), 7.90 (1H, d, J=7.93 Hz), 8.59 (1H, d, J=1.83 Hz).

G) 5-(chloromethyl)-2-(1-methyl-1H-pyrazol-3-yl) pyridine hydrochloride

To a solution of (6-(1-methyl-1H-pyrazol-3-yl)pyridin-3-yl)methanol (18.0 g) in dichloromethane (270 mL) was added TEA (11.16 mL) at room temperature, and methanesulfonyl chloride (7.3 mL) was added dropwise at 0° C. After stirring at room temperature for 16 hr, water was added, and the reaction mixture was extracted with dichloromethane. The organic layer was washed with saturated brine and dried over anhydrous sodium sulfate. The solvent was evaporated under reduced pressure. The residue was purified by silica gel column chromatography (ethyl acetate/ hexane) to give the title compound (13.0 g).

MS: [M+H]$^+$ 208.0.

H) 1,5-anhydro-2,3-dideoxy-3-(7,8-dimethyl-6-((6-(1-methyl-1H-pyrazol-3-yl)pyridin-3-yl)methyl)-4-oxoquinazolin-3(4H)-yl)-L-threo-pentitol A mixture of 1,5-anhydro-2,3-dideoxy-3-(7,8-dimethyl-4-oxo-6-(4,4,5,5-tetramethyl-1,3,2-dioxaborolan-2-yl)quinazolin-3(4H)-yl)-L-threo-pentitol (100 mg), 5-(chloromethyl)-2-(1-methyl-1H-pyrazol-3-yl)pyridine hydrochloride (91 mg), PdCl$_2$(dppf) (91 mg), 2 M aqueous sodium carbonate solution (0.375 mL) and DME (3 mL) was subjected to microwave irradiation at 100° C. for 1 hr. To the mixture was added water at room temperature, and the mixture was extracted with ethyl acetate. The organic layer was washed with saturated brine, dried over anhydrous sodium sulfate, and concentrated under reduced pressure. The obtained solid was crystallized from acetonitrile/MeOH to give the title compound (45.3 mg).

Example 2

1,5-anhydro-2,3-dideoxy-3-(7,8-dimethyl-6-((6-(1-methyl-1H-1,2,3-triazol-4-yl)pyridin-3-yl)methyl)-4-oxoquinazolin-3(4H)-yl)-L-threo-pentitol (Synonym) 3-((3R,4S)-3-hydroxytetrahydro-2H-pyran-4-yl)-7,8-dimethyl-6-((6-(1-methyl-1H-1,2,3-triazol-4-yl)pyridin-3-yl)methyl)quinazolin-4(3H)-one A) 5-(((tert-butyl(dimethyl)silyl)oxy)methyl)-2-chloropyridine A mixture of (6-chloropyridin-3-yl)methanol (6.50 g), 1H-imidazole (6.16 g), tert-butyldimethylchlorosilane (6.82 g) and THF (40 mL) was stirred at room temperature overnight. The reaction mixture was poured into water at room temperature, and the mixture was extracted twice with ethyl acetate. The residue was purified by silica gel column chromatography (ethyl acetate/hexane) to give the title compound (11.1 g).

MS: [M+H]$^+$ 258.1.

B) 5-(((tert-butyl(dimethyl)silyl)oxy)methyl)-2-((trimethylsilyl)ethynyl)pyridine A mixture of 5-(((tert-butyl(dimethyl)silyl)oxy)methyl)-2-chloropyridine (8.98 g), ethynyltrimethylsilane (5.13 g), copper(I) iodide (0.33 g), TEA (52.9 g), PdCl$_2$(dppf) dichloromethane adduct (1.422 g) and acetonitrile (100 mL) was stirred under a nitrogen atmosphere at 70° C. for 3 hr. The reaction mixture was concentrated under reduced pressure, and the residue was diluted with water and extracted with ethyl acetate. The organic layer was washed with saturated brine and dried over anhydrous magnesium sulfate. The solvent was evaporated under reduced pressure. The residue was purified by silica gel column chromatography. (ethyl acetate/hexane) to give the title compound (11.1 g).

MS: [M+H]$^+$ 320.0.

C) 5-(((tert-butyl(dimethyl)silyl)oxy)methyl)-2-ethynylpyridine

A mixture of 5-(((tert-butyl(dimethyl)silyl)oxy)methyl)-2-((trimethylsilyl)ethynyl)pyridine (11.1 g), potassium carbonate (4.80 g) and MeOH (50 mL) was stirred at room temperature for 2 hr. The reaction mixture was concentrated under reduced pressure, the residue was diluted with saturated aqueous ammonium chloride solution, and the mixture was extracted with ethyl acetate. The organic layer was washed with saturated brine and dried over anhydrous magnesium sulfate. The solvent was evaporated under reduced pressure to give the title compound (8.60 g).

MS: [M+H]$^+$ 248.0.

D) 5-(((tert-butyl(dimethyl)silyl)oxy)methyl)-2-(1-methyl-1H-1,2,3-triazol-4-yl)pyridine To a mixture of 5-(((tert-butyl(dimethyl)silyl)oxy)methyl)-2-ethynylpyridine (8.60 g), copper(I) bromide triphenylphosphine adduct (3.07 g), methyl iodide (5.43 g) and DMSO (80 mL) was added dropwise a solution of sodium azide (3.39 g) in water (20 mL), and the mixture was stirred under a nitrogen atmosphere at room temperature overnight. The reaction mixture was diluted with water at room temperature and the precipitate was collected by filtration. The isolated precipitate was dissolved in ethanol and the resulting insoluble material was filtered off. The filtrate was extracted with ethyl acetate and the organic layer was washed with saturated brine and dried over anhydrous magnesium sulfate. The solvent was evaporated under reduced pressure and the residue was purified by silica gel column chromatography (ethyl acetate/hexane) to give the title compound (7.03 g).

MS: [M+H]$^+$ 305.3.

E) (6-(1-methyl-1H-1,2,3-triazol-4-yl)pyridin-3-yl)methanol

A mixture of 1 M solution of tetra-n-butylammonium fluoride in THE (69.3 mL), 5-(((tert-butyl(dimethyl)silyl)oxy)methyl)-2-(1-methyl-1H-1,2,3-triazol-4-yl)pyridine (7.03 g) and THE (70 mL) was stirred at room temperature for 18 hr. The reaction mixture was concentrated, and the residue was purified by silica gel column chromatography (MeOH/ethyl acetate) to give the title compound (3.78 g).

$^1$H NMR (300 MHz, CDCl$_3$) δ 1.92 (1H, t, J=5.8 Hz), 4.17 (3H, s), 4.77 (2H, d, J=5.3 Hz), 7.81 (1H, dd, J=8.1, 2.3 Hz), 8.11 (1H, s), 8.17 (1H, d, J=8.1 Hz), 8.56 (1H, d, J=1.7 Hz).

F) 5-(bromomethyl)-2-(1-methyl-1H-1,2,3-triazol-4-yl)pyridine

To a mixture of (6-(1-methyl-1H-1,2,3-triazol-4-yl)pyridin-3-yl)methanol (0.40 g) and acetonitrile (8 mL) was added phosphorus tribromide (0.85 g) under ice-cooling, and the mixture was stirred under an argon atmosphere at room temperature for 30 min. To the reaction mixture was added saturated aqueous sodium hydrogen carbonate solution, and the mixture was extracted with ethyl acetate. The organic layer was dried over anhydrous sodium sulfate, and the solvent was evaporated under reduced pressure. The residue was washed with ethyl acetate-hexane to give the title compound (0.27 g).

MS, found: 253.1, 255.1.

G) 1,5-anhydro-2,3-dideoxy-3-(7,8-dimethyl-6-((6-(1-methyl-1H-1,2,3-triazol-4-yl)pyridin-3-yl)methyl)-4-oxoquinazolin-3(4H)-yl)-L-threo-pentitol (Synonym) 3-((3R,4S)-3-hydroxytetrahydro-2H-pyran-4-yl)-7,8-dimethyl-6-((6-(1-methyl-1H-1,2,3-triazol-4-yl)pyridin-3-yl)methyl)quinazolin-4(3H)-one To a mixture of 1,5-anhydro-2,3-dideoxy-3-(7,8-dimethyl-4-oxo-6-(4,4,5,5-tetramethyl-1,3,2-dioxaborolan-2-yl)quinazolin-3(4H)-yl)-L-threo-pentitol (1.02 g), 5-(bromomethyl)-2-(1-methyl-1H-1,2,3-triazol-4-yl)pyridine (0.838 g), 2 M aqueous sodium carbonate solution (7.64 mL) and DME (35 mL) was added PdCl$_2$(dppf) (0.093 g) at room temperature. The mixture was stirred under a nitrogen atmosphere at 80° C. overnight. To the mixture was added water at room temperature, and the mixture was extracted with a mixed solvent of ethyl acetate/THF. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). To the obtained fraction was added saturated aqueous sodium hydrogen carbonate solution, and the mixture was extracted with ethyl acetate. The organic layer was dried over anhydrous magnesium sulfate and concentrated under reduced pressure. The obtained solid was crystallized from ethyl acetate/hexane to give the title compound (289 mg).

$^1$H NMR (300 MHz, DMSO-d$_6$) δ 1.82 (1H, dd, J=12.7, 4.0 Hz), 2.08-2.25 (1H, m), 2.30 (3H, s), 2.53 (3H, s), 3.11 (1H, t, J=10.6 Hz), 3.35-3.52 (1H, m), 3.93 (2H, dt, J=11.0, 5.5 Hz), 4.05-4.15 (4H, m), 4.22 (2H, s), 4.44-4.61 (1H, m), 5.24 (1H, d, J=5.7 Hz), 7.56 (1H, dd, J=7.9, 2.3 Hz), 7.85 (1H, s), 7.95 (1H, d, J=8.2 Hz), 8.44 (1H, s), 8.48 (1H, d, J=1.5 Hz), 8.51 (1H, s).

Example 3

1,5-anhydro-2,3-dideoxy-3-(6-(3-fluoro-4-(methylcarbamoyl)benzyl)-7,8-dimethyl-4-oxoquinazolin-3(4H)-yl)-L-threo-pentitol (Synonym) 2-fluoro-4-((3-((3R,4S)-3-hydroxytetrahydro-2H-pyran-4-yl)-7,8-dimethyl-4-oxo-3,4-dihydroquinazolin-6-yl)methyl)-N-methylbenzamide

A) 1,5-anhydro-3-(6-bromo-7,8-dimethyl-4-oxoquinazolin-3(4H)-yl)-2-O-(tert-butyl(dimethyl)silyl)-3,4-dideoxy-L-threo-pentitol To a mixture of 1,5-anhydro-3-(6-bromo-7,8-dimethyl-4-oxoquinazolin-3(4H)-yl)-2,3-dideoxy-L-threo-pentitol (4.6 g), 1H-imidazole (2.66 g) and DMF (46 mL) was added tert-butyl(chloro)dimethylsilane (3.64 mL) at 0° C. The mixture was stirred at room temperature overnight. To the mixture was added water at room temperature, and the mixture was extracted with ethyl acetate. The organic layer was washed with water and saturated brine, dried over anhydrous sodium sulfate and concentrated under reduced pressure. The residue was purified by silica gel column chromatography (ethyl acetate/hexane) to give the title compound (5.7 g).
MS, found: 467.2, 469.2.

B) 1,5-anhydro-2-O-(tert-butyl(dimethyl)silyl)-3,4-dideoxy-3-(7,8-dimethyl-4-oxo-6-(4,4,5,5-tetramethyl-1,3,2-dioxaborolan-2-yl)quinazolin-3(4H)-yl)-L-threo-pentitol To a mixture of 1,5-anhydro-3-(6-bromo-7,8-dimethyl-4-oxoquinazolin-3(4H)-yl)-2-O-(tert-butyl(dimethyl)silyl)-3,4-dideoxy-L-threo-pentitol (25 g), bis(pinacolato)diboron (20.37 g), potassium acetate (15.75 g) and toluene (250 mL) was added PdCl$_2$(dppf) (1.957 g), and the mixture was stirred under an argon atmosphere at 80° C. overnight. The reaction mixture was purified by silica gel column chromatography (ethyl acetate/hexane) to give the title compound (26.4 g).
MS: [M+H]$^+$ 515.4.

C) 4-(bromomethyl)-2-fluorobenzoic acid

To a mixture of 2-fluoro-4-methylbenzoic acid (25.0 g), NBS (31.8 g) and trifluorotoluene (50 mL) was added AIBN (2.66 g). The mixture was stirred under a nitrogen atmosphere at 90° C. for 3.5 hr and stirred at room temperature overnight. To the mixture was added ethyl acetate at room temperature, and the mixture was washed with water and saturated brine, dried over anhydrous sodium sulfate and concentrated under reduced pressure. To the obtained solid was added isopropyl acetate/heptane (1/3). The solid was collected by filtration and washed with heptane to give the title compound (22.2 g).
$^1$H NMR (300 MHz, DMSO-d$_6$) δ 4.73 (2H, s), 7.35-7.45 (2H, m), 7.85 (1H, t, J=7.9 Hz), 13.31 (1H, brs).

D) 4-(bromomethyl)-2-fluoro-N-methylbenzamide

To a mixture of 4-(bromomethyl)-2-fluorobenzoic acid (27.2 g), a catalytic amount of DMF and ethyl acetate (270 mL) was added dropwise oxalyl chloride (33.3 g) at 0° C. The mixture was stirred at room temperature for 1.5 hr and concentrated under reduced pressure. The residue was dissolved in THF (270 mL) and added dropwise to a mixture of 2 M solution of methylamine in THF (57.8 mL), DIPEA (22 mL) and THF (100 mL) at 0° C. The mixture was stirred under a nitrogen atmosphere at 0° C. for 2 hr. Water (200 mL) was added dropwise to the mixture at 0° C., and the mixture was extracted with ethyl acetate. The organic layer was washed with water and saturated brine, dried over anhydrous sodium sulfate and concentrated under reduced pressure. The residue was purified by silica gel column chromatography (ethyl acetate/hexane) to give a yellow solid (19.28 g). A mixture of the obtained yellow solid (19.28 g), sodium bromide (68.5 g), lithium bromide (57.8 g) and MEK (200 mL) was refluxed for 5 hr. Impurity was filtered off, and the filtrate was concentrated under reduced pressure. To the obtained residue was added ethyl acetate, and the mixture was washed with water and saturated brine, dried over anhydrous sodium sulfate and concentrated under reduced pressure. The obtained solid was crystallized from ethyl acetate/hexane to give the title compound (15.1 g).
MS, found: 246.0, 248.0.

E) 1,5-anhydro-2-O-(tert-butyl(dimethyl)silyl)-3,4-dideoxy-3-(6-(3-fluoro-4-(methylcarbamoyl)benzyl)-7,8-dimethyl-4-oxoquinazolin-3(4H)-yl)-L-threo-pentitol To a mixture of 1,5-anhydro-2-O-(tert-butyl(dimethyl)silyl)-3,4-dideoxy-3-(7,8-dimethyl-4-oxo-6-(4,4,5,5-tetramethyl-1,3,2-dioxaborolan-2-yl)quinazolin-3(4H)-yl)-L-threo-pentitol (26 g), 4-(bromomethyl)-2-fluoro-N-methylbenzamide (12.43 g), 2 M aqueous sodium carbonate solution (76 mL) and DME (260 mL) was added PdCl$_2$(dppf) (0.37 g), and the mixture was stirred under an argon atmosphere at 80° C. for 3 hr. To the mixture was added water at room temperature, and the mixture was extracted with ethyl acetate. The organic layer was washed with water and saturated brine, dried over anhydrous sodium sulfate and concentrated under reduced pressure. The residue was purified by silica gel column chromatography (NH, ethyl acetate/hexane) to give the title compound (24 g).
MS: [M+H]$^+$ 554.4.

F) 1,5-anhydro-2,3-dideoxy-3-(6-(3-fluoro-4-(methylcarbamoyl)benzyl)-7,8-dimethyl-4-oxoquinazolin-3(4H)-yl)-L-threo-pentitol (Synonym) 2-fluoro-4-((3-((3R,4S)-3-hydroxytetrahydro-2H-pyran-4-yl)-7,8-dimethyl-4-oxo-3,4-dihydroquinazolin-6-yl)methyl)-N-methylbenzamide To a mixture of 1,5-anhydro-2-O-(tert-butyl(dimethyl)silyl)-3,4-dideoxy-3-(6-(3-fluoro-4-(methylcarbamoyl)benzyl)-7,8-dimethyl-4-oxoquinazolin-3(4H)-yl)-L-threo-pentitol (24 g) and THF (48 mL) was added 1 M solution of tetra-n-butylammonium fluoride in THF (47.7 mL) at room temperature, and the mixture was stirred at room temperature for 2 hr. To the reaction mixture were added DME (240 mL) and water (120 mL), and the mixture was stirred. The precipitate was collected by filtration and washed with IPE. The obtained solid (17.5 g) was dissolved in a mixture of DMSO (136 mL) and EtOH (34 mL) at 50° C., water (340 mL) was added and the mixture was further stirred at 50° C. for 1 hr. The mixture was stirred at room temperature for 2 hr, and the precipitate was collected by filtration and dried to give the title compound (16.8 g).
$^1$H NMR (300 MHz, DMSO-d$_6$) δ 1.82 (1H, dd, J=12.8, 4.2 Hz), 2.08-2.22 (1H, m), 2.25 (3H, s), 2.52 (3H, s), 2.75

(3H, d, J=4.5 Hz), 3.11 (1H, t, J=10.4 Hz), 3.36-3.49 (1H, m), 3.86-3.99 (2H, m), 4.02-4.17 (1H, m), 4.22 (2H, s), 4.44-4.64 (1H, m), 5.24 (1H, d, J=5.3 Hz), 6.96-7.08 (2H, m), 7.55 (1H, t, J=7.9 Hz), 7.84 (1H, s), 8.16 (1H, dd, J=4.2, 2.6 Hz), 8.44 (1H, s).

Example 5

1,5-anhydro-2,3-dideoxy-3-(6-((6-(1,3-dimethyl-1H-pyrazol-4-yl)pyridin-3-yl)methyl)-7,8-dimethyl-4-oxoquinazolin-3(4H)-yl)-L-threo-pentitol (Synonym) 6-((6-(1,3-dimethyl-1H-pyrazol-4-yl)pyridin-3-yl)methyl)-3-((3R,4S)-3-hydroxytetrahydro-2H-pyran-4-yl)-7,8-dimethylquinazolin-4(3H)-one A) 6-(1,3-dimethyl-1H-pyrazol-4-yl)nicotinaldehyde To a mixture of 6-chloronicotinaldehyde (7.0 g), 1,4-dioxane (400 mL) and water (10 mL) were added $PdCl_2$(dppf) (0.5 g), potassium carbonate (13.8 g) and 1,3-dimethyl-4-(4,4,5,5-tetramethyl-1,3,2-dioxaborolan-2-yl)-1H-pyrazole (16.5 g), and the mixture was stirred under a nitrogen atmosphere at 110° C. for 16 hr. The mixture was concentrated under reduced pressure and the residue was purified by silica gel column chromatography (ethyl acetate/hexane) to give the title compound (8.0 g).
MS: $[M+H]^+$ 202.1.

B) (6-(1,3-dimethyl-1H-pyrazol-4-yl)pyridin-3-yl)methanol

To a solution of 6-(1,3-dimethyl-1H-pyrazol-4-yl)nicotinaldehyde (8.0 g) in MeOH (300 mL) was added sodium borohydride (4.5 g) at 0° C., and the mixture was stirred at room temperature for 16 hr. To the reaction mixture was added water, and the mixture was extracted with dichloromethane. The organic layer was washed with water and saturated brine and dried over anhydrous sodium sulfate. The solvent was evaporated under reduced pressure to give the title compound (6.0 g). The compound was used in the next step without further purification.
MS: $[M+H]^+$ 204.1.

C) 5-(chloromethyl)-2-(1,3-dimethyl-1H-pyrazol-4-yl)pyridine

To a mixture of (6-(1,3-dimethyl-1H-pyrazol-4-yl)pyridin-3-yl)methanol (6.0 g) and dichloromethane (150 mL) was added thionyl chloride (10.5 g) at 0° C., and the mixture was stirred at room temperature for 16 hr. The mixture was neutralized with saturated aqueous sodium hydrogen carbonate solution and extracted with dichloromethane. The organic layer was washed with saturated brine, dried over anhydrous sodium sulfate and concentrated under reduced pressure. The residue was purified by silica gel column chromatography (ethyl acetate/petroleum ether) to give the title compound (4.5 g).
MS: $[M+H]^+$ 222.1.

D) 1,5-anhydro-2,3-dideoxy-3-(6-((6-(1,3-dimethyl-1H-pyrazol-4-yl)pyridin-3-yl)methyl)-7,8-dimethyl-4-oxoquinazolin-3(4H)-yl)-L-threo-pentitol (Synonym) 6-((6-(1,3-dimethyl-1H-pyrazol-4-yl)pyridin-3-yl)methyl)-3-((3R,4S)-3-hydroxytetrahydro-2H-pyran-4-yl)-7,8-dimethylquinazolin-4(3H)-one A mixture of 1,5-anhydro-2,3-dideoxy-3-(7,8-dimethyl-4-oxo-6-(4,4,5,5-tetramethyl-1,3,2-dioxaborolan-2-yl)quinazolin-3(4H)-yl)-L-threo-pentitol (125 mg), 5-(chloromethyl)-2-(1,3-dimethyl-1H-pyrazol-4-yl)pyridine (97 mg), 2 M aqueous sodium carbonate solution (0.468 mL), DME (3 mL) and $PdCl_2$(dppf) (11.42 mg) was subjected to microwave irradiation at 100° C. for 1 hr. To the mixture was added water at room temperature, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from MeOH/hexane to give the title compound (43 mg).
$^1$H NMR (300 MHz, DMSO-$d_6$) δ 1.82 (1H, dt, J=12.7, 1.4 Hz), 2.07-2.26 (1H, m), 2.31 (3H, s), 2.40 (3H, s), 2.53 (3H, s), 3.11 (1H, t, J=10.4 Hz), 3.32-3.49 (1H, m), 3.78 (3H, s), 3.88-3.99 (2H, m), 4.02-4.20 (3H, m), 4.39-4.62 (1H, m), 5.08-5.35 (1H, m), 7.48 (2H, s), 7.83 (1H, s), 8.11 (1H, s), 8.41 (2H, d, J=11.7 Hz).

Example 6

1,5-anhydro-2,3-dideoxy-3-(7,8-dimethyl-6-((6-(1-methyl-1H-pyrazol-4-yl)pyridin-3-yl)methyl)-4-oxoquinazolin-3(4H)-yl)-L-threo-pentitol (Synonym) 3-((3R,4S)-3-hydroxytetrahydro-2H-pyran-4-yl)-7,8-dimethyl-6-((6-(1-methyl-1H-pyrazol-4-yl)pyridin-3-yl)methyl)quinazolin-4(3H)-one A mixture of 1,5-anhydro-2,3-dideoxy-3-(7,8-dimethyl-4-oxo-6-(4,4,5,5-tetramethyl-1,3,2-dioxaborolan-2-yl)quinazolin-3(4H)-yl)-L-threo-pentitol (150 mg), 5-(chloromethyl)-2-(1-methyl-1H-pyrazol-4-yl)pyridine (101 mg), 2 M aqueous sodium carbonate solution (0.562 mL), $PdCl_2$(dppf) (13.71 mg) and DME (4 mL) was subjected to microwave irradiation at 100° C. for 1 hr. To the mixture was added water at room temperature, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from MeOH/hexane to give the title compound (64.2 mg).
$^1$H NMR (300 MHz, DMSO-$d_6$) δ 1.82 (1H, dd, J=12.7, 4.0 Hz), 2.12-2.23 (1H, m), 2.30 (3H, s), 2.53 (3H, s), 3.04-3.15 (1H, m), 3.42 (1H, t, J=11.0 Hz), 3.85-3.95 (5H, m), 4.05-4.19 (3H, m), 4.45-4.61 (1H, m), 5.24 (1H, d, J=4.5 Hz), 7.45 (1H, d, J=8.3 Hz), 7.54 (1H, d, J=8.0 Hz), 7.81 (1H, s), 7.93 (1H, d, J=0.8 Hz), 8.21 (1H, s), 8.36 (1H, d, J=1.5 Hz), 8.43 (1H, s).

Example 10

1,5-anhydro-3-(8-chloro-6-(3-fluoro-4-(methylcarbamoyl)benzyl)-7-methyl-4-oxoquinazolin-3(4H)-yl)-2,3-dideoxy-L-threo-pentitol A) 2-amino-5-bromo-4-methylbenzoic acid To a mixture of 2-amino-4-methylbenzoic acid (6.14 g) and DMSO (60 mL) was added hydrobromic acid (48% v/v, 23 mL) at 0° C., and the mixture was stirred at room temperature overnight. To the reaction mixture was added water (150 mL) and the mixture was stirred for 30 min. The precipitate was collected by filtration, washed with water and dried to give the title compound (9.04 g).

MS, found: 230.0, 232.0.

B) 2-amino-5-bromo-3-chloro-4-methylbenzoic acid

To a mixture of 2-amino-5-bromo-4-methylbenzoic acid (9.04 g) and acetonitrile (180 mL) was added NCS (7.35 g) at room temperature. The mixture was stirred at room temperature overnight. The precipitate was collected by filtration, washed with a small amount of ethyl acetate and dried under reduced pressure to give the title compound (5.59 g).

MS, found: 264.0, 266.0.

C) 3-((2-amino-5-bromo-3-chloro-4-methylbenzoyl) amino)-1,5-anhydro-2,3-dideoxy-L-threo-pentitol To a mixture of 2-amino-5-bromo-3-chloro-4-methylbenzoic acid (5 g), 3-amino-1,5-anhydro-2,3-dideoxy-L-threo-pentitol hydrochloride (2.9 g), HATU (8.63 g) and DMF (100 mL) was added TEA (6.59 mL) at room temperature, and the mixture was stirred overnight. To the reaction mixture was added 5% aqueous sodium hydrogen carbonate solution, and the mixture was extracted with ethyl acetate. The organic layer was washed with saturated brine, dried over anhydrous sodium sulfate and concentrated under reduced pressure to give the title compound (8.75 g). Further purification was not performed and the compound was used in the next step.

MS, found: 363.0, 365.0.

D) 1,5-anhydro-3-(6-bromo-8-chloro-7-methyl-4-oxoquinazolin-3(4H)-yl)-2,3-dideoxy-L-threo-pentitol A mixture of 3-((2-amino-5-bromo-3-chloro-4-methylbenzoyl)amino)-1,5-anhydro-2,3-dideoxy-L-threo-pentitol (8.75 g) and N,N-dimethylformamide dimethyl acetal (80 mL) was stirred under a nitrogen atmosphere at 90° C. for 2 hr. The reaction mixture was concentrated under reduced pressure and the obtained solid was crystallized from ethyl acetate/hexane to give the title compound (6.52 g).

MS, found: 373.0, 375.0.

E) 1,5-anhydro-3-(8-chloro-7-methyl-4-oxo-6-(4,4,5,5-tetramethyl-1,3,2-dioxaborolan-2-yl)quinazolin-3(4H)-yl)-2,3-dideoxy-L-threo-pentitol To a mixture of 1,5-anhydro-3-(6-bromo-8-chloro-7-methyl-4-oxoquinazolin-3(4H)-yl)-2,3-dideoxy-L-threo-pentitol (3.5 g), bis(pinacolato)diboron (2.85 g), potassium acetate (2.76 g) and toluene (60 mL) was added $Pd(PPh_3)_2Cl_2$ (0.329 g), and the mixture was stirred under a nitrogen atmosphere at 110° C. overnight. To the reaction mixture was added 5% aqueous sodium hydrogen carbonate solution at room temperature, and the mixture was extracted with ethyl acetate/THF mixed solvent. The organic layer was washed with saturated brine and dried over anhydrous magnesium sulfate. The solvent was evaporated under reduced pressure. The obtained solid was washed with IPE to give the title compound (2.37 g). Further purification was not performed and the compound was used in the next step.

MS: [M+H]$^+$ 421.2.

F) 1,5-anhydro-3-(8-chloro-6-(3-fluoro-4-(methylcarbamoyl)benzyl)-7-methyl-4-oxoquinazolin-3(4H)-yl)-2,3-dideoxy-L-threo-pentitol A mixture of 1,5-anhydro-3-(8-chloro-7-methyl-4-oxo-6-(4,4,5,5-tetramethyl-1,3,2-dioxaborolan-2-yl)quinazolin-3(4H)-yl)-2,3-dideoxy-L-threo-pentitol (150 mg), 4-(bromomethyl)-2-fluoro-N-methylbenzamide (114 mg), 2 M aqueous sodium carbonate solution (0.535 mL), $PdCl_2(dppf)$ (13.04 mg) and DME (5 mL) was subjected to microwave irradiation at 100° C. for 1 hr. To the mixture was added water at room temperature, and the mixture was extracted with ethyl acetate/THF mixed solvent. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from acetonitrile/hexane to give the title compound (89 mg).

Example 17

1,5-anhydro-3-(6-(4-carboxybenzyl)-7,8-dimethyl-4-oxoquinazolin-3(4H)-yl)-2,3-dideoxy-L-threo-pentitol A) 1,5-anhydro-2,3-dideoxy-3-(6-(4-(methoxycarbonyl)benzyl)-7,8-dimethyl-4-oxoquinazolin-3(4H)-yl)-L-threo-pentitol A mixture of 1,5-anhydro-2,3-dideoxy-3-(7,8-dimethyl-4-oxo-6-(4,4,5,5-tetramethyl-1,3,2-dioxaborolan-2-yl)quinazolin-3(4H)-yl)-L-threo-pentitol (8.58 g), methyl 4-(chloromethyl)benzoate (3.75 g), $PdCl_2(dppf)$ (0.62 g), sodium carbonate (4.49 g), water (20 mL) and DME (120 mL) was stirred under an argon atmosphere at 80° C. for 10 hr. To the mixture was added water at room temperature, and the mixture was extracted with ethyl acetate. The organic layer was washed with water and saturated brine, dried over anhydrous sodium sulfate and concentrated under reduced pressure. The residue was purified by silica gel column chromatography (NH, ethyl acetate/hexane) to give the title compound (4.5 g).

MS: [M+H]$^+$ 423.3.

B) 1,5-anhydro-3-(6-(4-carboxybenzyl)-7,8-dimethyl-4-oxoquinazolin-3(4H)-yl)-2,3-dideoxy-L-threo-pentitol To a mixture of 1,5-anhydro-2,3-dideoxy-3-(6-(4-(methoxycarbonyl)benzyl)-7,8-dimethyl-4-oxoquinazolin-3(4H)-yl)-L-threo-pentitol (4.5 g), THF (45 mL) and MeOH (45 mL) was added 2 M aqueous sodium hydroxide solution (16 mL), and the mixture was stirred under a nitrogen atmosphere at room temperature overnight, and further stirred at 45° C. for 4 hr. The mixture was cooled to room temperature, neutralized with 2 M hydrochloric acid and concentrated under reduced pressure. To the residue was added ethyl acetate, and the mixture was concentrated again under reduced pressure. The precipitated solid was collected by filtration, washed with water, and dried to give the title compound (3.95 g).

$^1$H NMR (300 MHz, DMSO-d$_6$) δ 1.77-1.90 (1H, m), 2.11-2.32 (4H, m), 2.45-2.54 (3H, m), 3.06-3.16 (1H, m), 3.37-3.48 (1H, m), 3.87-3.99 (2H, m), 4.02-4.17 (1H, m), 4.24 (2H, s), 4.47-4.64 (1H, m), 5.25 (1H, d, J=5.7 Hz), 7.24 (2H, d, J=8.3 Hz), 7.83 (1H, s), 7.87 (2H, d, J=8.3 Hz), 8.43 (1H, s), 12.83 (1H, brs).

Example 18

1,5-anhydro-2,3-dideoxy-3-(7,8-dimethyl-6-(4-(methylcarbamoyl)benzyl)-4-oxoquinazolin-3(4H)-yl)-L-threo-pentitol To a mixture of 1,5-anhydro-3-(6-(4-carboxybenzyl)-7,8-dimethyl-4-oxoquinazolin-3(4H)-yl)-2,3-dideoxy-L-threo-pentitol (60 mg), methylamine hydrochloride (19.84 mg), DIPEA (76 mg) and DMA (2 mL) was added HATU (84 mg) at room temperature and the mixture was stirred for 10 hr. To the reaction mixture was added water, and the mixture was extracted with ethyl acetate. The organic layer was washed with water and saturated brine, dried over anhydrous sodium sulfate and concentrated under reduced pressure. The residue was purified by silica gel column chromatography (NH, ethyl acetate/hexane) to give the title compound (38.6 mg).

Example 19

1,5-anhydro-3-(8-chloro-6-(3-fluoro-4-(methylcarbamoyl)benzyl)-7-methyl-4-oxo-1,2,3-benzotriazin-3(4H)-yl)-2,3-dideoxy-L-threo-pentitol (Synonym) 4-((8-chloro-3-((3R,4S)-3-hydroxytetrahydro-2H-pyran-4-yl)-7-methyl-4-oxo-3,4-dihydrobenzo[d][1,2,3]triazin-6-yl)methyl)-2-fluoro-N-methylbenzamide A) 1,5-anhydro-3-(6-bromo-8-chloro-7-methyl-4-oxo-1,2,3-benzotriazin-3(4H)-yl)-2,3-dideoxy-L-threo-pentitol To a mixture of 3-((2-amino-5-bromo-3-chloro-4-methylbenzoyl)amino)-1,5-anhydro-2,3-dideoxy-L-threo-pentitol (4.59 g) and 2 M hydrochloric acid (38 mL) was added dropwise a solution of sodium nitrite (0.91 g) in water (10 mL) at 0° C., and the mixture was stirred at room temperature for 3 hr. The reaction mixture was neutralized with 2 M aqueous sodium hydroxide solution at 0° C., and the precipitate was collected by filtration and washed with water to give the title compound (1.9 g). Further purification was not performed and the compound was used in the next step.

MS, found: 374.1, 376.1.

B) 1,5-anhydro-3-(8-chloro-7-methyl-4-oxo-6-(4,4,5,5-tetramethyl-1,3,2-dioxaborolan-2-yl)-1,2,3-benzotriazin-3(4H)-yl)-2,3-dideoxy-L-threo-pentitol To a mixture of 1,5-anhydro-3-(6-bromo-8-chloro-7-methyl-4-oxo-1,2,3-benzotriazin-3(4H)-yl)-2,3-dideoxy-L-threo-pentitol (1.89 g), bis(pinacolato)diboron (1.54 g), potassium acetate (1.49 g) and toluene (60 mL) was added Pd(PPh$_3$)$_2$Cl$_2$ (0.33 g), and the mixture was stirred under a nitrogen atmosphere at 110° C. overnight. To the reaction mixture was added 5% aqueous sodium hydrogen carbonate solution, and the mixture was extracted with ethyl acetate/THF mixed solvent. The organic layer was washed with saturated brine and dried over anhydrous magnesium sulfate. The solvent was evaporated under reduced pressure. The obtained solid was crystallized from ethyl acetate/hexane to give the title compound (609 mg). Further purification was not performed and the compound was used in the next step.

MS: 422.2.

C) 1,5-anhydro-3-(8-chloro-6-(3-fluoro-4-(methylcarbamoyl)benzyl)-7-methyl-4-oxo-1,2,3-benzotriazin-3(4H)-yl)-2,3-dideoxy-L-threo-pentitol (Synonym) 4-((8-chloro-3-((3R,4S)-3-hydroxytetrahydro-2H-pyran-4-yl)-7-methyl-4-oxo-3,4-dihydrobenzo[d][1,2,3]triazin-6-yl)methyl)-2-fluoro-N-methylbenzamide A mixture of 1,5-anhydro-3-(8-chloro-7-methyl-4-oxo-6-(4,4,5,5-tetramethyl-1,3,2-dioxaborolan-2-yl)-1,2,3-benzotriazin-3(4H)-yl)-2,3-dideoxy-L-threo-pentitol (180 mg), 4-(bromomethyl)-2-fluoro-N-methylbenzamide (137 mg), 2 M aqueous sodium carbonate solution (0.640 mL), PdCl$_2$(dppf) (15.62 mg) and DME (5 mL) was subjected to microwave irradiation at 100° C. for 1 hr. To the mixture was added water at room temperature, and the mixture was extracted with ethyl acetate/THF mixed solvent. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction filtered through StratoSpheres SPE (PL-HCO3 MP-Resin) and concentrated under reduced pressure. The obtained solid was crystallized from acetonitrile/hexane to give the title compound (28 mg).

$^1$H NMR (400 MHz, CD$_3$OD) δ 1.98-2.07 (1H, m), 2.29 (1H, qd, J=12.6, 4.8 Hz), 2.54 (3H, s), 2.90 (4H, s), 3.30 (1H, dt, J=3.3, 1.5 Hz), 3.59 (1H, td, J=12.0, 2.1 Hz), 4.01-4.13 (2H, m), 4.29 (1H, td, J=10.0, 5.1 Hz), 4.35 (2H, s), 4.86 (1H, s), 5.09 (1H, ddd, J=12.1, 9.9, 4.6 Hz), 7.02 (1H, d, J=12.0 Hz), 7.08 (1H, dd, J=7.9, 1.6 Hz), 7.70 (1H, t, J=7.8 Hz), 8.01 (1H, s).

Example 21

1,5-anhydro-2,3-dideoxy-3-(8-fluoro-6-(3-fluoro-4-(methylcarbamoyl)benzyl)-7-methyl-4-oxoquinazolin-3(4H)-yl)-L-threo-pentitol A) 2-amino-5-bromo-3-fluoro-4-methylbenzoic acid To a mixture of 2-amino-3-fluoro-4-methylbenzoic acid (10 g) and DMF (200 mL) was added NBS (12.63 g) at 0° C. The mixture was stirred at 0° C. for 1 hr and further stirred at room temperature overnight. To the mixture was added water (300 mL) at room temperature, and the precipitated solid was collected by filtration, washed with water and dried under reduced pressure to give the title compound (14.4 g).

MS, found: 248.0, 250.0.

B) 3-((2-amino-5-bromo-3-fluoro-4-methylbenzoyl)amino)-1,5-anhydro-2,3-dideoxy-L-threo-pentitol To a mixture of 2-amino-5-bromo-3-fluoro-4-methylbenzoic acid (10 g), 3-amino-1,5-anhydro-2,3-dideoxy-L-threopentitol hydrochloride (6.19 g), HATU (18.4 g) and DMF (150 mL) was added TEA (14 mL) at room temperature and the mixture was stirred overnight. To the reaction mixture was added 5% aqueous sodium hydrogen carbonate solution, and the mixture was extracted with ethyl acetate. The organic layer was washed with saturated brine, dried over anhydrous magnesium sulfate and concentrated under reduced pressure. The obtained solid was crystallized from ethyl acetate to give the title compound (3.57 g).

MS, found: 347.1, 349.1.

C) 1,5-anhydro-3-(6-bromo-8-fluoro-7-methyl-4-oxoquinazolin-3(4H)-yl)-2,3-dideoxy-L-threo-pentitol A mixture of 3-((2-amino-5-bromo-3-fluoro-4-methylbenzoyl)amino)-1,5-anhydro-2,3-dideoxy-L-threo-pentitol (14.1 g) and N,N-dimethylformamide dimethyl acetal (50 mL) was stirred under a nitrogen atmosphere at 90° C. for 2 hr. The reaction mixture was concentrated under reduced pressure and the obtained solid was crystallized from ethyl acetate/hexane to give the title compound (8.36 g).

MS, found: 357.1, 359.1.

D) 1,5-anhydro-2,3-dideoxy-3-(8-fluoro-7-methyl-4-oxo-6-(4,4,5,5-tetramethyl-1,3,2-dioxaborolan-2-yl)quinazolin-3(4H)-yl)-L-threo-pentitol To a mixture of 1,5-anhydro-3-(6-bromo-8-fluoro-7-methyl-4-oxoquinazolin-3(4H)-yl)-2,3-dideoxy-L-threo-pentitol (5.0 g), bis(pinacolato)diboron (4.27 g), potassium acetate (4.12 g) and toluene (60 mL) was added Pd(PPh$_3$)$_2$Cl$_2$ (0.329 g), and the mixture was stirred under a nitrogen atmosphere at 110° C. overnight. To the reaction mixture was added 5% aqueous sodium hydrogen carbonate solution at room temperature, and the mixture was extracted with ethyl acetate/THF mixed solvent.

The organic layer was washed with saturated brine and dried over anhydrous magnesium sulfate. The solvent was evaporated under reduced pressure. The obtained solid was washed with IPE to give the title compound (3.47 g). Further purification was not performed and the compound was used in the next step.

MS: [M+H]$^+$ 405.3.

E) 1,5-anhydro-2,3-dideoxy-3-(8-fluoro-6-(3-fluoro-4-(methylcarbamoyl)benzyl)-7-methyl-4-oxoquinazolin-3(4H)-yl)-L-threo-pentitol A mixture of 1,5-anhydro-2,3-dideoxy-3-(8-fluoro-7-methyl-4-oxo-6-(4,4,5,5-tetramethyl-1,3,2-dioxaborolan-2-yl)quinazolin-3(4H)-yl)-L-threo-pentitol (150 mg), 4-(bromomethyl)-2-fluoro-N-methylbenzamide (119 mg), 2 M aqueous sodium carbonate solution (0.557 mL), PdCl$_2$(dppf) (13.58 mg) and DME (5 mL) was subjected to microwave irradiation at 100° C. for 1 hr. To the mixture was added water at room temperature, and the mixture was extracted with ethyl acetate/THF mixed solvent. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from MeOH/hexane to give the title compound (28.8 mg).

Example 60

1,5-anhydro-3-(6-(4-carboxy-3-fluorobenzyl)-7,8-dimethyl-4-oxoquinazolin-3(4H)-yl)-2,3-dideoxy-L-threo-pentitol A) 1,5-anhydro-2,3-dideoxy-3-(6-(3-fluoro-4-(methoxycarbonyl)benzyl)-7,8-dimethyl-4-oxoquinazolin-3(4H)-yl)-L-threo-pentitol To a mixture of 1,5-anhydro-2,3-dideoxy-3-(7,8-dimethyl-4-oxo-6-(4,4,5,5-tetramethyl-1,3,2-dioxaborolan-2-yl)quinazolin-3(4H)-yl)-L-threo-pentitol (6.75 g), methyl 4-(bromomethyl)-2-fluorobenzoate (5.00 g), 2 M aqueous sodium carbonate solution (25.3 mL) and DME (100 mL) was added PdCl$_2$(dppf) (0.62 g), and the mixture was stirred under a nitrogen atmosphere at 80° C. for 2 hr. To the mixture was added water at room temperature, and the mixture was extracted with ethyl acetate. The organic layer was washed with saturated brine, dried over anhydrous magnesium sulfate and concentrated under reduced pressure. The residue was purified by silica gel column chromatography (NH, ethyl acetate/hexane) and the obtained solid was crystallized from ethyl acetate/hexane to give the title compound (3.44 g).

MS: [M+H]+ 441.2.

B) 1,5-anhydro-3-(6-(4-carboxy-3-fluorobenzyl)-7,8-dimethyl-4-oxoquinazolin-3(4H)-yl)-2,3-dideoxy-L-threo-pentitol To a mixture of 1,5-anhydro-2,3-dideoxy-3-(6-(3-fluoro-4-(methoxycarbonyl)benzyl)-7,8-dimethyl-4-oxoquinazolin-3(4H)-yl)-L-threo-pentitol (4.06 g), THF (50 mL) and MeOH (25 mL) was added 2 M aqueous sodium hydroxide solution (10 mL), and the mixture was stirred at 50° C. overnight. The mixture was cooled to room temperature, neutralized with 2 M hydrochloric acid and extracted with ethyl acetate. The organic layer was washed with water and saturated brine, dried over anhydrous magnesium sulfate and concentrated under reduced pressure. The obtained solid was crystallized from ethyl acetate/hexane to give the title compound (3.41 g).

Example 66

1,5-anhydro-2,3-dideoxy-3-(6-(3-fluoro-4-((2-methoxyethyl)carbamoyl)benzyl)-7,8-dimethyl-4-oxoquinazolin-3(4H)-yl)-L-threo-pentitol (Synonym) 2-fluoro-4-((3-((3R,4S)-3-hydroxytetrahydro-2H-pyran-4-yl)-7,8-dimethyl-4-oxo-3,4-dihydroquinazolin-6-yl)methyl)-N-(2-methoxyethyl)benzamide To a mixture of 1,5-anhydro-3-(6-(4-carboxy-3-fluorobenzyl)-7,8-dimethyl-4-oxoquinazolin-3(4H)-yl)-2,3-dideoxy-L-threo-pentitol (110 mg), 2-methoxyethanamine (38.7 mg), DIPEA (0.18 mL) and DMA (4 mL) was added HATU (147 mg) at room temperature. The mixture was stirred at room temperature overnight. Water was added to the mixture, and the precipitated solid was collected by filtration, washed with water and dried under reduced pressure to give the title compound (94 mg).

$^1$H NMR (300 MHz, DMSO-d$_6$) δ 1.74-1.87 (1H, m), 2.11-2.31 (4H, m), 2.52 (3H, brs), 3.11 (1H, t, J=10.6 Hz), 3.26 (3H, s), 3.36-3.46 (5H, m), 3.93 (2H, dt, J=11.0, 5.1

Hz), 3.99-4.14 (1H, m), 4.22 (2H, s), 4.41-4.64 (1H, m), 5.24 (1H, d, J=5.3 Hz), 6.94-7.10 (2H, m), 7.54 (1H, t, J=7.9 Hz), 7.84 (1H, s), 8.21 (1H, d, J=3.0 Hz), 8.44 (1H, s).

Example 71

1,5-anhydro-3-(6-((6-(1-(cyclopropylmethyl)-1H-pyrazol-4-yl)pyridin-3-yl)methyl)-7,8-dimethyl-4-oxoquinazolin-3(4H)-yl)-2,3-dideoxy-L-threo-pentitol (Synonym) 6-((6-(1-(cyclopropylmethyl)-1H-pyrazol-4-yl)pyridin-3-yl)methyl)-3-((3R,4S)-3-hydroxytetrahydro-2H-pyran-4-yl)-7,8-dimethylquinazolin-4(3H)-one A) 1,5-anhydro-3-(6-((6-chloropyridin-3-yl)methyl)-7,8-dimethyl-4-oxoquinazolin-3(4H)-yl)-2,3-dideoxy-L-threo-pentitol To a mixture of 1,5-anhydro-2,3-dideoxy-3-(7,8-dimethyl-4-oxo-6-(4,4,5,5-tetramethyl-1,3,2-dioxaborolan-2-yl)quinazolin-3(4H)-yl)-L-threo-pentitol (1500 mg), 2-chloro-5-(chloromethyl)pyridine (729 mg), 2 M aqueous sodium carbonate solution (5.62 mL) and DME (50 mL) was added PdCl$_2$(dppf) (0.137 g), and the mixture was stirred under a nitrogen atmosphere at 80° C. overnight. To the mixture was added water at room temperature, and the mixture was extracted with ethyl acetate.

The organic layer was washed with saturated brine, dried over anhydrous magnesium sulfate and concentrated under reduced pressure. The residue was purified by silica gel column chromatography (Diol, ethyl acetate/hexane) to give the title compound (952 mg).

MS: [M+H]$^+$ 400.2.

B) 1,5-anhydro-3-(6-((6-(1-(cyclopropylmethyl)-1H-pyrazol-4-yl)pyridin-3-yl)methyl)-7,8-dimethyl-4-oxoquinazolin-3(4H)-yl)-2,3-dideoxy-L-threo-pentitol (Synonym) 6-((6-(1-(cyclopropylmethyl)-1H-pyrazol-4-yl)pyridin-3-yl)methyl)-3-((3R,4S)-3-hydroxytetrahydro-2H-pyran-4-yl)-7,8-dimethylquinazolin-4(3H)-one A mixture of 1,5-anhydro-3-(6-((6-chloropyridin-3-yl)methyl)-7,8-dimethyl-4-oxoquinazolin-3(4H)-yl)-2,3-dideoxy-L-threo-pentitol (140 mg), 1-(cyclopropylmethyl)-4-(4,4,5,5-tetramethyl-1,3,2-dioxaborolan-2-yl)-1H-pyrazole (130 mg), PdCl$_2$(Amphos)$_2$ (23.55 mg), 2 M aqueous sodium carbonate solution (0.525 mL) and DME (4 mL) was subjected to microwave irradiation at 110° C. for 1 hr. To the mixture was added water at room temperature, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from ethyl acetate/hexane to give the title compound (39 mg).

$^1$H NMR (300 MHz, DMSO-d$_6$) δ 0.35-0.42 (2H, m), 0.51-0.58 (2H, m), 1.21-1.28 (1H, m), 1.82 (1H, dd, J=12.3, 3.6 Hz), 2.06-2.26 (1H, m), 2.30 (3H, s), 2.53 (3H, s), 3.11 (1H, t, J=10.4 Hz), 3.42 (1H, t, J=11.0 Hz), 3.87-4.13 (6H, m), 4.19 (2H, s), 4.53 (1H, brs), 7.55-7.71 (2H, m), 7.83 (1H, s), 8.01 (1H, s), 8.36 (1H, s), 8.40-8.46 (2H, m).

Example 72

1,5-anhydro-3-(6-((6-(1-tert-butyl-1H-pyrazol-4-yl)pyridin-3-yl)methyl)-7,8-dimethyl-4-oxoquinazolin-3(4H)-yl)-2,3-dideoxy-L-threo-pentitol (Synonym) 6-((6-(1-(tert-butyl)-1H-pyrazol-4-yl)pyridin-3-yl)methyl)-3-((3R,4S)-3-hydroxytetrahydro-2H-pyran-4-yl)-7,8-dimethylquinazolin-4(3H)-one A mixture of 1,5-anhydro-3-(6-((6-chloropyridin-3-yl)methyl)-7,8-dimethyl-4-oxoquinazolin-3(4H)-yl)-2,3-dideoxy-L-threo-pentitol (140 mg), 1-tert-butyl-4-(4,4,5,5-tetramethyl-1,3,2-dioxaborolan-2-yl)-1H-pyrazole (131 mg), PdCl$_2$(Amphos)$_2$ (23.55 mg) and 2 M aqueous sodium carbonate solution (0.525 mL) and DME (4 mL) was subjected to microwave irradiation at 110° C. for 1 hr. To the mixture was added water at room temperature, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin), and concentrated under reduced pressure. The obtained solid was crystallized from ethyl acetate/hexane to give the title compound (55.4 mg).

$^1$H NMR (300 MHz, DMSO-d$_6$) δ 1.55 (9H, s), 1.70-1.90 (1H, m), 2.05-2.24 (1H, m), 2.30 (3H, s), 2.53 (3H, s), 3.11 (1H, t, J=10.4 Hz), 3.42 (1H, t, J=11.0 Hz), 3.83-4.19 (5H, m), 4.43-4.63 (1H, m), 5.24 (1H, d, J=5.3 Hz), 7.45 (1H, dd, J=8.1, 2.1 Hz), 7.60 (1H, d, J=7.9 Hz), 7.80 (1H, s), 7.97 (1H, s), 8.31-8.45 (3H, m).

Example 73

1,5-anhydro-2,3-dideoxy-3-(6-((6-(1-(2-methoxyethyl)-1H-pyrazol-4-yl)pyridin-3-yl)methyl)-7,8-dimethyl-4-oxoquinazolin-3(4H)-yl)-L-threo-pentitol (Synonym) 3-((3R,4S)-3-hydroxytetrahydro-2H-pyran-4-yl)-6-((6-(1-(2-methoxyethyl)-1H-pyrazol-4-yl)pyridin-3-yl)methyl)-7,8-dimethylquinazolin-4(3H)-one A mixture of 1,5-anhydro-3-(6-((6-chloropyridin-3-yl)methyl)-7,8-dimethyl-4-oxoquinazolin-3(4H)-yl)-2,3-dideoxy-L-threo-pentitol (140 mg), 1-(2-methoxyethyl)-4-(4,4,5,5-tetramethyl-1,3,2-dioxaborolan-2-yl)-1H-pyrazole (132 mg), PdCl$_2$(Amphos)$_2$ (23.55 mg), 2 M aqueous sodium carbonate solution (0.525 mL) and DME (4 mL) was subjected to microwave irradiation at 110° C. for 1 hr. To the mixture was added water at room temperature, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from ethyl acetate/hexane to give the title compound (45.2 mg).

¹H NMR (300 MHz, DMSO-d₆) δ 1.71-1.92 (1H, m), 2.08-2.34 (4H, m), 2.53 (3H, s), 3.11 (1H, t, J=10.4 Hz), 3.23 (3H, s), 3.34-3.50 (1H, m), 3.71 (2H, t, J=5.1 Hz), 3.87-3.97 (2H, m), 4.04-4.14 (1H, m), 4.22 (2H, s), 4.32 (2H, t, J=5.3 Hz), 4.42-4.69 (1H, m), 4.99-5.85 (1H, m), 7.60-7.76 (2H, m), 7.84 (1H, s), 8.07 (1H, s), 8.35 (1H, s), 8.42-8.48 (2H, m).

Example 74

1,5-anhydro-2,3-dideoxy-3-(7,8-dimethyl-4-oxo-6-((6-(1-(2,2,2-trifluoroethyl)-1H-pyrazol-4-yl)pyridin-3-yl)methyl)quinazolin-3(4H)-yl)-L-threo-pentitol (Synonym) 3-((3R,4S)-3-hydroxytetrahydro-2H-pyran-4-yl)-7,8-dimethyl-6-((6-(1-(2,2,2-trifluoroethyl)-1H-pyrazol-4-yl)pyridin-3-yl)methyl)quinazolin-4(3H)-one A mixture of 1,5-anhydro-3-(6-((6-chloropyridin-3-yl)methyl)-7,8-dimethyl-4-oxoquinazolin-3(4H)-yl)-2,3-dideoxy-L-threo-pentitol (140 mg), 4-(4,4,5,5-tetramethyl-1,3,2-dioxaborolan-2-yl)-1-(2,2,2-trifluoroethyl)-1H-pyrazole (145 mg), PdCl₂(Amphos)₂ (23.55 mg), 2 M aqueous sodium carbonate solution (0.525 mL) and DME (4 mL) was subjected to microwave irradiation at 110° C. for 1 hr. To the mixture was added water at room temperature, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from ethyl acetate/hexane to give the title compound (75 mg).

¹H NMR (300 MHz, DMSO-d₆) δ 1.72-1.72 (1H, m), 2.08-2.34 (4H, m), 2.53 (3H, s), 3.11 (1H, t, J=10.2 Hz), 3.42 (1H, t, J=11.0 Hz), 3.93 (2H, dt, J=10.9, 5.3 Hz), 4.03-4.14 (1H, m), 4.18 (2H, s), 4.44-4.61 (1H, m), 5.13-5.28 (3H, m), 7.49 (1H, dd, J=8.3, 2.3 Hz), 7.62 (1H, d, J=7.9 Hz), 7.82 (1H, s), 8.11 (1H, s), 8.36-8.45 (3H, m).

Example 75

1,5-anhydro-2,3-dideoxy-3-(7,8-dimethyl-4-oxo-6-((6-(1-(tetrahydro-2H-pyran-4-yl)-1H-pyrazol-4-yl)pyridin-3-yl)methyl)quinazolin-3(4H)-yl)-L-threo-pentitol (Synonym) 3-((3R,4S)-3-hydroxytetrahydro-2H-pyran-4-yl)-7,8-dimethyl-6-((6-(1-(tetrahydro-2H-pyran-4-yl)-1H-pyrazol-4-yl)pyridin-3-yl)methyl)quinazolin-4(3H)-one A mixture of 1,5-anhydro-3-(6-((6-chloropyridin-3-yl)methyl)-7,8-dimethyl-4-oxoquinazolin-3(4H)-yl)-2,3-dideoxy-L-threo-pentitol (140 mg), 1-(tetrahydro-2H-pyran-4-yl)-4-(4,4,5,5-tetramethyl-1,3,2-dioxaborolan-2-yl)-1H-pyrazole (146 mg), PdCl₂(Amphos)₂ (23.55 mg), 2 M aqueous sodium carbonate solution (0.525 mL) and DME (4 mL) was subjected to microwave irradiation at 110° C. for 1 hr. To the mixture was added water at room temperature, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from ethyl acetate/hexane to give the title compound (42 mg).

¹H NMR (300 MHz, DMSO-d₆) δ 1.75-1.88 (1H, m), 1.96-2.03 (4H, m), 2.10-2.25 (1H, m), 2.31 (3H, s), 2.53 (3H, s), 3.11 (1H, t, J=10.4 Hz), 3.37-3.53 (3H, m), 3.88-4.13 (6H, m), 4.23 (2H, s), 4.42-4.58 (2H, m), 7.72-7.85 (3H, m), 8.11 (1H, s), 8.43-8.51 (3H, m).

Example 81

1,5-anhydro-2,3-dideoxy-3-(6-(3-fluoro-4-(((2R)-tetrahydrofuran-2-ylmethyl)carbamoyl)benzyl)-7,8-dimethyl-4-oxoquinazolin-3(4H)-yl)-L-threo-pentitol (Synonym) 2-fluoro-4-((3-((3R,4S)-3-hydroxytetrahydro-2H-pyran-4-yl)-7,8-dimethyl-4-oxo-3,4-dihydroquinazolin-6-yl)methyl)-N—(((R)-tetrahydrofuran-2-yl)methyl)benzamide To a mixture of 1,5-anhydro-3-(6-(4-carboxy-3-fluorobenzyl)-7,8-dimethyl-4-oxoquinazolin-3(4H)-yl)-2,3-dideoxy-L-threo-pentitol (90 mg), (S)-(tetrahydrofuran-2-yl)methanamine (28.2 mg), DIPEA (0.144 mL) and DMA (3 mL) was added HATU (120 mg) at room temperature. The mixture was stirred at room temperature overnight. To the mixture was added water at room temperature, and the mixture was extracted with ethyl acetate. The organic layer was washed with saturated brine, dried over anhydrous magnesium sulfate and concentrated under reduced pressure. The residue was purified by silica gel column chromatography (NH, MeOH/ethyl acetate) and the obtained solid was crystallized from ethyl acetate/IPE/hexane to give the title compound (54.9 mg).

¹H NMR (300 MHz, DMSO-d₆) δ 1.49-1.65 (1H, m), 1.73-1.93 (4H, m), 2.09-2.23 (1H, m, J=4.2 Hz), 2.25 (3H, s), 2.52 (3H, brs), 3.11 (1H, t, J=10.4 Hz), 3.26-3.30 (1H, m), 3.35-3.50 (1H, m), 3.56-3.66 (2H, m), 3.72-3.80 (1H, m), 3.89-4.01 (3H, m), 4.02-4.16 (1H, m), 4.22 (2H, s), 4.38-4.74 (1H, m), 5.24 (1H, d, J=5.3 Hz), 6.98-7.06 (2H, m), 7.53 (1H, t, J=7.9 Hz), 7.85 (1H, s), 8.21 (1H, d, J=3.0 Hz), 8.44 (1H, s).

Example 82

1,5-anhydro-2,3-dideoxy-3-(6-((6-(1-(2-(dimethylamino)-2-oxoethyl)-1H-pyrazol-4-yl)pyridin-3-yl)methyl)-7,8-dimethyl-4-oxoquinazolin-3(4H)-yl)-L-threo-pentitol A) 1,5-anhydro-2,3-dideoxy-3-(7,8-dimethyl-4-oxo-6-((6-(1H-pyrazol-4-yl)pyridin-3-yl)methyl)quinazolin-3(4H)-yl)-L-threo-pentitol A mixture of 1,5-anhydro-3-(6-((6-chloropyridin-3-yl)methyl)-7,8-dimethyl-4-oxoquinazolin-3(4H)-yl)-2,3-dideoxy-L-threo-pentitol (150 mg), tert-butyl 4-(4,4,5,5-tetramethyl-1,3,2-dioxaborolan-2-yl)-1H-pyrazole-1-carboxylate (166 mg), PdCl₂(dppf) (25.2 mg), 2 M aqueous sodium carbonate solution (0.563 mL) and DME (4 mL) was subjected to microwave irradiation at 110° C. for 1 hr. To the mixture was added water at room temperature, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 0.1% TFA)). The obtained fraction was filtered through StratoSpheres SPE (PL-HCO3 MP-Resin) and concentrated under reduced pressure. The obtained solid was crystallized from acetonitrile/MeOH to give the title compound (43.0 mg).
MS: [M+H]$^+$ 432.2.

B) 1,5-anhydro-2,3-dideoxy-3-(6-((6-(1-(2-(dimethylamino)-2-oxoethyl)-1H-pyrazol-4-yl)pyridin-3-yl)methyl)-7,8-dimethyl-4-oxoquinazolin-3(4H)-yl)-L-threo-pentitol To a mixture of 1,5-anhydro-2,3-dideoxy-3-(7,8-dimethyl-4-oxo-6-((6-(1H-pyrazol-4-yl)pyridin-3-yl)methyl)quinazolin-3(4H)-yl)-L-threo-pentitol (39.5 mg) and DMF (2 mL) was added 60% sodium hydride (10 mg) at room temperature. The reaction mixture was stirred under a nitrogen atmosphere at room temperature for 30 min, and 2-chloro-N,N-dimethylacetamide (20 mg) was added. After stirring at room temperature overnight, to the mixture was added water, and the mixture was extracted with ethyl acetate. The organic layer was washed with saturated brine, dried over anhydrous magnesium sulfate and concentrated under reduced pressure. The residue was purified by HPLC (L-Column 2 ODS, mobile phase: water/acetonitrile (containing 10 mM ammonium bicarbonate)). The obtained fraction was concentrated under reduced pressure to give the title compound (10.9 mg).
$^1$H NMR (300 MHz, CD$_3$OD) δ 1.90-1.99 (1H, m), 2.27-2.39 (4H, m), 2.57 (3H, s), 2.97 (3H, s), 3.13 (3H, s), 3.23 (1H, dd, J=11.0, 10.2 Hz), 3.53 (1H, d, J=1.9 Hz), 3.97-4.11 (2H, m), 4.16-4.29 (3H, m), 4.48-4.66 (1H, m), 5.17 (2H, s), 6.92 (1H, d, J=0.8 Hz), 7.50-7.60 (2H, m), 7.93 (1H, s), 8.01 (1H, d, J=0.8 Hz), 8.13 (1H, s), 8.26-8.32 (2H, m).

Example 85

1,5-anhydro-2,3-dideoxy-3-(6-(4-((2-ethoxyethyl)carbamoyl)-3-fluorobenzyl)-7,8-dimethyl-4-oxoquinazolin-3(4H)-yl)-L-threo-pentitol (Synonym) N-(2-ethoxyethyl)-2-fluoro-4-((3-((3R,4S)-3-hydroxytetrahydro-2H-pyran-4-yl)-7,8-dimethyl-4-oxo-3,4-dihydroquinazolin-6-yl)methyl)benzamide To a mixture of 1,5-anhydro-3-(6-(4-carboxy-3-fluorobenzyl)-7,8-dimethyl-4-oxoquinazolin-3(4H)-yl)-2,3-dideoxy-L-threo-pentitol (90 mg), 2-ethoxyethanamine (28.2 mg), DIPEA (0.14 mL) and DMA (3 mL) was added HATU (120 mg) at room temperature. The mixture was stirred at room temperature overnight. To the mixture was added water at room temperature, and the mixture was extracted with ethyl acetate. The organic layer was washed with saturated brine, dried over anhydrous magnesium sulfate and concentrated under reduced pressure. The residue was purified by silica gel column chromatography (NH, MeOH/ethyl acetate) and the obtained solid was crystallized from ethyl acetate/hexane to give the title compound (71.4 mg).
$^1$H NMR (300 MHz, DMSO-d$_6$) δ 1.10 (3H, t, J=7.0 Hz), 1.77-1.87 (1H, m), 2.08-2.30 (4H, m), 2.52 (3H, brs), 3.11 (1H, t, J=10.4 Hz), 3.35-3.48 (7H, m), 3.93 (2H, dt, J=10.9, 5.3 Hz), 4.00-4.16 (1H, m), 4.22 (2H, s), 4.42-4.67 (1H, m), 5.24 (1H, d, J=5.3 Hz), 6.99-7.06 (2H, m), 7.55 (1H, t, J=8.0 Hz), 7.85 (1H, s), 8.16-8.24 (1H, m), 8.44 (1H, s).

Example 86

1,5-anhydro-2,3-dideoxy-3-(6-(3-fluoro-4-((3-methoxypropyl)carbamoyl)benzyl)-7,8-dimethyl-4-oxoquinazolin-3(4H)-yl)-L-threo-pentitol (Synonym) 2-fluoro-4-((3-((3R,4S)-3-hydroxytetrahydro-2H-pyran-4-yl)-7,8-dimethyl-4-oxo-3,4-dihydroquinazolin-6-yl)methyl)-N-(3-methoxypropyl)benzamide To a mixture of 1,5-anhydro-3-(6-(4-carboxy-3-fluorobenzyl)-7,8-dimethyl-4-oxoquinazolin-3(4H)-yl)-2,3-dideoxy-L-threo-pentitol (90 mg), 3-methoxypropan-1-amine (37.6 mg), DIPEA (0.14 mL) and DMA (3 mL) was added HATU (120 mg) at room temperature. The mixture was stirred at room temperature overnight. To the mixture was added water at room temperature, and the mixture was extracted with ethyl acetate. The organic layer was washed with saturated brine, dried over anhydrous magnesium sulfate and concentrated under reduced pressure. The residue was purified by silica gel column chromatography (NH, MeOH/ethyl acetate) and the obtained solid was crystallized from ethyl acetate/IPE/hexane to give the title compound (55.7 mg).
$^1$H NMR (300 MHz, DMSO-d$_6$) δ 1.63-1.87 (3H, m), 2.09-2.31 (4H, m), 2.52 (3H, s), 3.11 (1H, t, J=10.4 Hz), 3.24-3.53 (8H, m), 3.93 (2H, dt, J=10.9, 5.3 Hz), 4.01-4.15 (1H, m), 4.22 (2H, s), 4.39-4.71 (1H, m), 5.24 (1H, d, J=5.3 Hz), 6.98-7.06 (2H, m), 7.53 (1H, t, J=7.8 Hz), 7.84 (1H, s), 8.18-8.26 (1H, m), 8.44 (1H, s).

Example 87

1,5-anhydro-3-(6-(4-(cyclopropylcarbamoyl)-3-fluorobenzyl)-7,8-dimethyl-4-oxoquinazolin-3(4H)-yl)-2,3-dideoxy-L-threo-pentitol (Synonym) N-cyclopropyl-2-fluoro-4-((3-((3R,4S)-3-hydroxytetrahydro-2H-pyran-4-yl)-7,8-dimethyl-4-oxo-3,4-dihydroquinazolin-6-yl)methyl)benzamide To a mixture of 1,5-anhydro-3-(6-(4-carboxy-3-fluorobenzyl)-7,8-dimethyl-4-oxoquinazolin-3(4H)-yl)-2,3-dideoxy-L-threo-pentitol (90 mg), cyclopropanamine (24.10 mg), DIPEA (0.14 mL) and DMA (3 mL) was added HATU (120 mg) at room temperature. The mixture was stirred at room temperature for 15 hr. To the mixture was added water, and the precipitated solid was collected by filtration, washed with water and IPE and dried under reduced pressure to give the title compound (83 mg).
$^1$H NMR (300 MHz, DMSO-d$_6$) δ 0.46-0.59 (2H, m), 0.61-0.70 (2H, m), 1.73-1.89 (1H, m), 2.10-2.30 (4H, m), 2.52 (3H, s), 2.76-2.86 (1H, m), 3.11 (1H, t, J=10.4 Hz), 3.35-3.52 (1H, m), 3.93 (2H, dt, J=10.8, 5.2 Hz), 4.03-4.14 (1H, m), 4.21 (2H, s), 4.42-4.66 (1H, m), 5.24 (1H, d, J=5.7

Hz), 6.97-7.04 (2H, m), 7.47 (1H, t, J=7.9 Hz), 7.83 (1H, s), 8.28 (1H, d, J=3.8 Hz), 8.43 (1H, s).

Example 92

1,5-anhydro-2,3-dideoxy-3-(6-((fluoro(3-fluoro-4-(methylcarbamoyl)phenyl)methyl)-7,8-dimethyl-4-oxoquinazolin-3(4H)-yl)-L-threo-pentitol (Diastereomeric Mixture)

A) 2-fluoro-4-(hydroxymethyl)-N-methylbenzamide

To a mixture of 4-(bromomethyl)-2-fluoro-N-methylbenzamide (3 g) and DMF (12 mL) was added potassium acetate (1.436 g), and the mixture was stirred at room temperature for 3 hr. Potassium carbonate (3.37 g) and methanol (4 mL) were added and the mixture was stirred at room temperature for 3 hr. To the mixture was added water, and the mixture was extracted 7 times with mixture of ethyl acetate and 2-propanol. The organic layer was separated, dried over anhydrous sodium sulfate and concentrated under reduced pressure. The residue was purified by silica gel column chromatography (ethyl acetate/hexane) to give the title compound (2.0 g).
MS: [M+H]$^+$ 184.2.

B) 2-fluoro-4-formyl-N-methylbenzamide

To a mixture of 2-fluoro-4-(hydroxymethyl)-N-methylbenzamide (100 mg) and toluene (5 mL) was added manganese dioxide (237 mg) at 70° C. The mixture was stirred at 70° C. for 2 hr, and the reaction mixture was purified by silica gel column chromatography (ethyl acetate/hexane) to give the title compound (74 mg).
$^1$H NMR (300 MHz, DMSO-d$_6$) δ 2.79 (3H, d, J=4.5 Hz), 7.68-7.90 (3H, m), 8.48 (1H, brs), 10.03 (1H, d, J=1.5 Hz).

C) 1,5-anhydro-2-O-(tert-butyl(dimethyl)silyl)-3,4-dideoxy-3-(6-iodo-7,8-dimethyl-4-oxoquinazolin-3(4H)-yl)-L-threo-pentitol A mixture of 1,5-anhydro-3-(6-bromo-7,8-dimethyl-4-oxoquinazolin-3(4H)-yl)-2-O-(tert-butyl(dimethyl)silyl)-3,4-dideoxy-L-threo-pentitol (1.0 g), trans-1,2-bis(methylamino)cyclohexane (30 mg), copper(I) iodide (20 mg), sodium iodide (962 mg) and acetonitrile was subjected to microwave irradiation at 130° C. for 24 hr. To the mixture was added aqueous ammonia at room temperature, and the mixture was extracted with ethyl acetate. The organic layer was washed with water and saturated brine, dried over anhydrous magnesium sulfate and concentrated under reduced pressure. The residue was purified by silica gel column chromatography (ethyl acetate/hexane) to give the title compound (860 mg).
MS: [M+H]$^+$ 515.3.

D) 1,5-anhydro-2-O-(tert-butyl(dimethyl)silyl)-3,4-dideoxy-3-(6-((3-fluoro-4-(methylcarbamoyl)phenyl)(hydroxy)methyl)-7,8-dimethyl-4-oxoquinazolin-3(4H)-yl)-L-threo-pentitol (Diastereomic Mixture)

To a solution of 1,5-anhydro-2-O-(tert-butyl(dimethyl)silyl)-3,4-dideoxy-3-(6-iodo-7,8-dimethyl-4-oxoquinazolin-3(4H)-yl)-L-threo-pentitol (760 mg) in THF was added dropwise 1.3 M THF solution (1.136 mL) of isopropylmagnesium chloride-lithium chloride complex under an argon atmosphere at −10° C. The reaction mixture was stirred at −10° C. for 30 min and 2-fluoro-4-formyl-N-methylbenzamide (268 mg) was added. To the mixture was added saturated aqueous ammonium chloride solution, and the mixture was extracted with ethyl acetate. The organic layer was separated, washed with water and saturated brine, dried over anhydrous sodium sulfate, and concentrated under reduced pressure. The residue was purified by silica gel column chromatography (NH, ethyl acetate/hexane) to give the title compound (220 mg).
MS: [M+H]$^+$ 570.4.

E) 1,5-anhydro-2-O-(tert-butyl(dimethyl)silyl)-3,4-dideoxy-3-(6-(fluoro(3-fluoro-4-(methylcarbamoyl)phenyl)methyl)-7,8-dimethyl-4-oxoquinazolin-3(4H)-yl)-L-threo-pentitol (Diastereomeric Mixture)

To a mixture of 1,5-anhydro-2-O-(tert-butyl(dimethyl)silyl)-3,4-dideoxy-3-(6-((3-fluoro-4-(methylcarbamoyl)phenyl)(hydroxy)methyl)-7,8-dimethyl-4-oxoquinazolin-3(4H)-yl)-L-threo-pentitol (diastereomeric mixture) (220 mg) and toluene was added (diethylamino)sulfur trifluoride (0.0663 mL) under an argon atmosphere at −40° C. The mixture was stirred at −40° C. for 1 hr, saturated aqueous sodium hydrogen carbonate was added, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (174 mg).
MS: [M+H]$^+$ 572.4.

F) 1,5-anhydro-2,3-dideoxy-3-(6-(fluoro(3-fluoro-4-(methylcarbamoyl)phenyl)methyl)-7,8-dimethyl-4-oxoquinazolin-3(4H)-yl)-L-threo-pentitol (Diastereomeric Mixture)

To a mixture of 1,5-anhydro-2-O-(tert-butyl(dimethyl)silyl)-3,4-dideoxy-3-(6-(fluoro(3-fluoro-4-(methylcarbamoyl)phenyl)methyl)-7,8-dimethyl-4-oxoquinazolin-3(4H)-yl)-L-threo-pentitol (25 mg) and THF was added 1 M tetra-N-butylammonium fluoride THF solution (0.0568 mL) at room temperature, and the mixture was stirred at room temperature for 1 hr. To the reaction mixture were added DME and water, and the mixture was stirred. The precipitate was collected by filtration and dried to give the title compound (12.2 mg).

Example 93

1,5-anhydro-2,3-dideoxy-3-(6-(fluoro(3-fluoro-4-(methylcarbamoyl)phenyl)methyl)-7,8-dimethyl-4-oxoquinazolin-3(4H)-yl)-L-threo-pentitol (Epimer of Example 94)

A) 1,5-anhydro-2-O-(tert-butyl(dimethyl)silyl)-3,4-dideoxy-3-(6-(fluoro(3-fluoro-4-(methylcarbamoyl)phenyl)methyl)-7,8-dimethyl-4-oxoquinazolin-3(4H)-yl)-L-threo-pentitol (Stereoisomer: Retention Time Short)

1,5-Anhydro-2-O-(tert-butyl(dimethyl)silyl)-3,4-dideoxy-3-(6-(fluoro(3-fluoro-4-(methylcarbamoyl)phenyl)methyl)-7,8-dimethyl-4-oxoquinazolin-3(4H)-yl)-L-threo-pentitol (diastereomeric mixture) (177 mg) obtained in step E of Example 92 was separated by SFC (column: CHIRALPAK AD-H, 20 mmID×250 mmL, mobile phase: carbon dioxide/EtOH=740/260, flow rate: 50 mL/min) to give the title compound (69 mg) having a shorter retention time (tR1).

100% ee (SFC (column: CHIRALPAK IC, 4.6 mmID× 250 mmL, mobile phase: carbon dioxide/EtOH=740/260, flow rate: 2.5 mL/min, retention time: 3.98 min))

MS: [M+H]$^+$ 572.3.

B) 1,5-anhydro-2,3-dideoxy-3-(6-(fluoro(3-fluoro-4-(methylcarbamoyl)phenyl)methyl)-7,8-dimethyl-4-oxoquinazolin-3(4H)-yl)-L-threo-pentitol (Epimer of Example 94)

The title compound was obtained by a method similar to that in step F of Example 92.

Example 94

1,5-anhydro-2,3-dideoxy-3-(6-(fluoro(3-fluoro-4-(methylcarbamoyl)phenyl)methyl)-7,8-dimethyl-4-oxoquinazolin-3(4H)-yl)-L-threo-pentitol (Epimer of Example 93)

A) 1,5-anhydro-2-O-(tert-butyl(dimethyl)silyl)-3,4-dideoxy-3-(6-(fluoro(3-fluoro-4-(methylcarbamoyl)phenyl)methyl)-7,8-dimethyl-4-oxoquinazolin-3(4H)-yl)-L-threo-pentitol (Stereoisomer: Retention Time Long)

1,5-Anhydro-2-O-(tert-butyl(dimethyl)silyl)-3,4-dideoxy-3-(6-(fluoro(3-fluoro-4-(methylcarbamoyl)phenyl)methyl)-7,8-dimethyl-4-oxoquinazolin-3(4H)-yl)-L-threo-pentitol (diastereomeric mixture) (177 mg) obtained in step E of Example 92 was separated by SFC (column: CHIRALPAK AD-H, 20 mmID×250 mmL, mobile phase: carbon dioxide/EtOH=740/260, flow rate: 50 mL/min) to give the title compound (74 mg) having a longer retention time (tR2).

100% ee (SFC (column: CHIRALPAK IC, 4.6 mmID× 250 mmL, mobile phase: carbon dioxide/EtOH=740/260, flow rate: 2.5 mL/min, retention time: 4.65 min))

MS: [M+H]$^+$ 572.3.

B) 1,5-anhydro-2,3-dideoxy-3-(6-(fluoro(3-fluoro-4-(methylcarbamoyl)phenyl)methyl)-7,8-dimethyl-4-oxoquinazolin-3(4H)-yl)-L-threo-pentitol (Epimer of Example 93)

The title compound was obtained by a method similar to that in step F of Example 92.

The compounds of Examples are shown in the following Tables. In the Tables, MS means measured values. The compounds of Examples 4, 7-9, 11-16, 20, 22-59, 61-65, 67-70, 76-80, 83, 84 and 88-91 in the following Tables were produced by the methods shown in the above-mentioned Examples or a method analogous thereto.

TABLE 1-1

| Ex. No. | IUPAC name | structural formula | salt | MS |
|---|---|---|---|---|
| 1 | 1,5-anhydro-2,3-dideoxy-3-(7,8-dimethyl-6-((6-(1-methyl-1H-pyrazol-3-yl)pyridin-3-yl)methyl)-4-oxoquinazolin-3(4H)-yl)-L-threo-pentitol | | | 446.3 |
| 2 | 1,5-anhydro-2,3-dideoxy-3-(7,8-dimethyl-6-((6-(1-methyl-1H-1,2,3-triazol-4-yl)pyridin-3-yl)methyl)-4-oxoquinazolin-3(4H)-yl)-L-threo-pentitol (synonym) 3-((3R,4S)-3-hydroxytetrahydro-2H-pyran-4-yl)-7,8-dimethyl-6-((6-(1-methyl-1H-1,2,3-triazol-4-yl)pyridin-3-yl)methyl)quinazolin-4(3H)-one | | | 447.1 |

TABLE 1-1-continued

| Ex. No. | IUPAC name | structural formula | salt | MS |
|---|---|---|---|---|
| 3 | 1,5-anhydro-2,3-dideoxy-3-(6-(3-fluoro-4-(methylcarbamoyl)benzyl)-7,8-dimethyl-4-oxoquinazolin-3(4H)-yl)-L-threo-pentitol (synonym) 2-fluoro-4-((3-((3R,4S)-3-hydroxytetrahydro-2H-pyran-4-yl)-7,8-dimethyl-4-oxo-3,4-dihydroquinazolin-6-yl)methyl)-N-methylbenzamide | | | 440.2 |
| 4 | 1,5-anhydro-2,3-dideoxy-3-(7,8-dimethyl-6-(4-(6-methylpyridazin-4-yl)benzyl)-4.-oxoquinazolin-3(4H)-yl)-L-threo-pentitol | | | 457.2 |

TABLE 1-2

| Ex. No. | IUPAC name | structural formula | salt | MS |
|---|---|---|---|---|
| 5 | 1,5-anhydro-2,3-dideoxy-3-(6-((6-(1,3-dimethyl-1H-pyrazol-4-yl)pyridin-3-yl)methyl)-7,8-dimethyl-4-oxoquinazolin-3(4H)-yl)-L-threo-pentitol (synonym) 6-((6-(1,3-dimethyl-1H-pyrazol-4-yl)pyridin-3-yl)methyl)-3-((3R,4S)-3-hydroxytetrahydro-2H-pyran-4-yl)-7,8-dimethylquinazolin-4(3H)-one | | | 460.3 |

TABLE 1-2-continued

| Ex. No. | IUPAC name | structural formula | salt | MS |
|---|---|---|---|---|
| 6 | 1,5-anhydro-2,3-dideoxy-3-(7,8-dimethyl-6-((6-(1-methyl-1H-pyrazol-4-yl)pyridin-3-yl)methyl)-4-oxoquinazolin-3(4H)-yl)-L-threo-pentitol (synonym) 3-((3R,4S)-3-hydroxytetrahydro-2H-pyran-4-yl)-7,8-dimethyl-6-((6-(1-methyl-1H-pyrazol-4-yl)pyridin-3-yl)methyl)quinazolin-4(3H)-one | | | 446.3 |
| 7 | 1,5-anhydro-2,3-dideoxy-3-(7,8-dimethyl-6-((6-methylpyridin-3-yl)methyl)-4-oxoquinazolin-3(4H)-yl)-L-threo-pentitol | | | 380.3 |
| 8 | 1,5-anhydro-2,3-dideoxy-3-(7,8-dimethyl-6-(4-(1-methyl-1H-1,2,3-triazol-4-yl)benzyl)-4-oxoquinazolin-3(4H)-yl)-L-threo-pentitol | | | 446.2 |

TABLE 1-3

| Ex. No. | IUPAC name | structural formula | salt | MS |
|---|---|---|---|---|
| 9 | 1,5-anhydro-2,3-dideoxy-3-(7,8-dimethyl-6-(4-(1-methyl-1H-pyrazol-4-yl)benzyl)-4-oxoquinazolin-3(4H)-yl)-L-threo-pentitol | | | 445.3 |
| 10 | 1,5-anhydro-3-(8-chloro-6-(3-fluoro-4-(methylcarbamoyl)benzyl)-7-methyl-4-oxoquinazolin-3(4H)-yl)-2,3-dideoxy-1-threo-pentitol | | | 460.2 |
| 11 | 1,5-anhydro-3-(8-chloro-7-methyl-6-((6-(1-methyl-1H-pyrazol-4-yl)pyridin-3-yl)methyl)-4-oxoquinazolin-3(4H)-yl)-2,3-dideoxy-L-threo-pentitol | | | 466.2 |

TABLE 1-3-continued

| Ex. No. | IUPAC name | structural formula | salt | MS |
|---|---|---|---|---|
| 12 | 1,5-anhydro-3-(8-chloro-6-((6-(1,3-dimethyl-1H-pyrazol-4-yl)pyridin-3-yl)methyl)-7-methyl-4-oxoquinazolin-3(4H)-yl)-2,3-dideoxy-L-threo-pentitol | | | 480.2 |
| 13 | 1,5-anhydro-3-(8-chloro-7-methyl-6-((6-(1-methyl-1H-pyrazol-3-yl)pyridin-3-yl)methyl)-4-oxoquinazolin-3(4H)-yl)-2,3-dideoxy-L-threo-pentitol | | | 466.2 |

TABLE 1-4

| Ex. No. | IUPAC name | structural formula | salt | MS |
|---|---|---|---|---|
| 14 | 1,5-anhydro-3-(8-chloro-7-methyl-6-((6-(1-methyl-1H-1,2,3-triazol-4-yl)pyridin-3-yl)methyl)-4-oxoquinazolin-3(4H)-yl)-2,3-dideoxy-L-threo-pentitol | | | 467.2 |

TABLE 1-4-continued

| Ex. No. | IUPAC name | structural formula | salt | MS |
|---|---|---|---|---|
| 15 | 1,5-anhydro-3-(8-chloro-7-methyl-6-(4-(1-methyl-1H-1,2,3-triazol-4-yl)benzyl)-4-oxoquinazolin-3(4H)-yl)-2,3-dideoxy-L-threo-pentitol | | | 466.2 |
| 16 | 1,5-anhydro-3-(8-chloro-7-methyl-6-((6-methylpyridin-3-yl)methyl)-4-oxoquinazolin-3(4H)-yl)-2,3-dideoxy-L-threo-pentitol | | | 400.2 |
| 17 | 1,5-anhydro-3-(6-(4-carboxybenzyl)-7,8-dimethyl-4-oxoquinazolin-3(4H)-yl)-2,3-dideoxy-L-threo-pentitol | | | 407.1 |

TABLE 1-4-continued

| Ex. No. | IUPAC name | structural formula | salt | MS |
|---|---|---|---|---|
| 18 | 1,5-anhydro-2,3-dideoxy-3-(7,8-dimethyl-6-(4-(methylcarbamoyl)benzyl)-4-oxoquinazolin-3(4H)-yl)-L-threo-pentitol | | | 422.2 |

TABLE 1-5

| Ex. No. | IUPAC name | structural formula | salt | MS |
|---|---|---|---|---|
| 19 | 1,5-anhydro-3-(8-chloro-6-(3-fluoro-4-(methylcarbamoyl)benzyl)-7-methyl-4-oxo-1,2,3-benzotriazin-3(4H)-yl)-2,3-dideoxy-L-threo-pentitol (synonym) 4-((8-chloro-3-((3R,4S)-3-hydroxytetrahydro-2H-pyran-4-yl)-7-methyl-4-oxo-3,4-dihydrobenzo[d][1,2,3]triazin-6-yl)methyl)-2-fluoro-N-methylbenzamide | | | 461.2 |
| 20 | 1,5-anhydro-3-(8-chloro-7-methyl-6-(4-(1-methyl-1H-1,2,3-triazol-4-yl)benzyl)-4-oxo-1,2,3-benzotriazin-3(4H)-yl)-2,3-dideoxy-L-threo-pentitol | | | 467.2 |

TABLE 1-5-continued

| Ex. No. | IUPAC name | structural formula | salt | MS |
|---|---|---|---|---|
| 21 | 1,5-anhydro-2,3-dideoxy-3-(8-fluoro-6-(3-fluoro-4-(methylcarbamoyl)benzyl)-7-methyl-4-oxoquinazolin-3(4H)-yl)-L-threo-pentitol | | | 444.2 |
| 22 | 1,5-anhydro-2,3-dideoxy-3-(8-fluoro-7-methyl-6-(4-(1-methyl-1H-1,2,3-triazol-4-yl)benzyl)-4-oxoquinazolin-3(4H)-yl)-L-threo-pentitol | | | 450.2 |

TABLE 1-6

| Ex. No. | IUPAC name | structural formula | salt | MS |
|---|---|---|---|---|
| 23 | 1,5-anhydro-2,3-dideoxy-3-(6-((6-(1,3-dimethyl-1H-pyrazol-4-yl)pyridin-3-yl)methyl)-8-fluoro-7-methyl-4-oxoquinazolin-3(4H)-yl)-L-threo-pentitol | | | 464.2 |

TABLE 1-6-continued

| Ex. No. | IUPAC name | structural formula | salt | MS |
|---|---|---|---|---|
| 24 | 1,5-anhydro-2,3-dideoxy-3-(8-fluoro-7-methyl-6-(4-(1-methyl-1H-pyrazol-4-yl)benzyl)-4-oxoquinazolin-3(4H)-yl)-L-threo-pentitol | | | 449.1 |
| 25 | 1,5-anhydro-2,3-dideoxy-3-(6-(4-((3,3-difluorocyclobutyl)-carbamoyl)benzyl)-7,8-dimethyl-4-oxoquinazolin-3(4H)-yl)-L-threo-pentitol | | | 498.2 |
| 26 | 1,5-anhydro-2,3-dideoxy-3-(7,8-dimethyl-6-(4-((3-methyloxetan-3-yl)carbamoyl)benzyl)-4-oxoquinazolin-3(4H)-yl)-L-threo-pentitol | | | 478.2 |

TABLE 1-6-continued

| Ex. No. | IUPAC name | structural formula | salt | MS |
|---|---|---|---|---|
| 27 | 1,5-anhydro-2,3-dideoxy-3-(7,8-dimethyl-6-(4-(oxetan-3-ylcarbamoyl)benzyl)-4-oxoquinazolin-3(4H)-yl)-L-threo-pentitol | 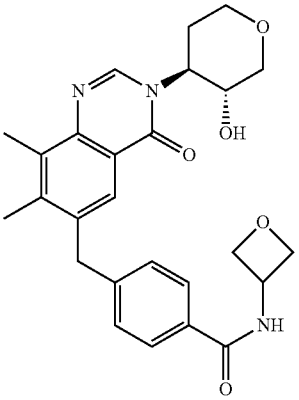 [SMILES: Cc1c(Cc2ccc(C(=O)NC3COC3)cc2)cc2c(=O)n([C@H]3CCOC[C@@H]3O)cnc2c1C] | | 464.2 |

TABLE 1-7

| Ex. No. | IUPAC name | structural formula | salt | MS |
|---|---|---|---|---|
| 28 | 1,5-anhydro-2,3-dideoxy-3-(6-(4-(ethylcarbamoyl)benzyl)-7,8-dimethyl-4-oxoquinazolin-3 (4H)-yl)-L-threo-pentitol | 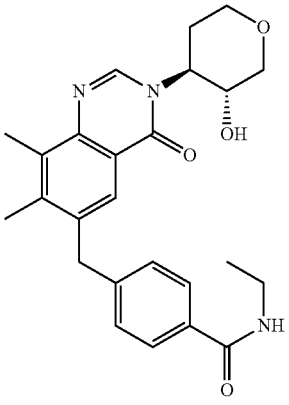 [SMILES: CCNC(=O)c1ccc(Cc2cc3c(=O)n([C@H]4CCOC[C@@H]4O)cnc3c(C)c2C)cc1] | | 436.2 |
| 29 | 1,5-anhydro-3-(6-(4-((cyclopropylmethyl)carbamoyl)-benzyl)-7,8-dimethyl-4-oxoquinazolin-3 (4H)-yl)-2,3-dideoxy-L-threo-pentitol | 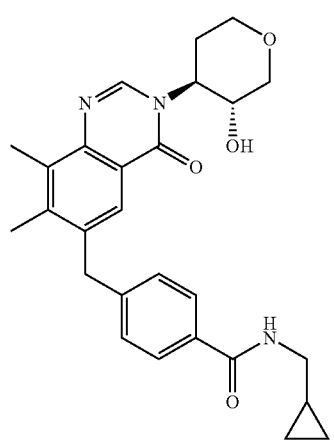 [SMILES: Cc1c(Cc2ccc(C(=O)NCC3CC3)cc2)cc2c(=O)n([C@H]3CCOC[C@@H]3O)cnc2c1C] | | 462.2 |

TABLE 1-7-continued

| Ex. No. | IUPAC name | structural formula | salt | MS |
|---|---|---|---|---|
| 30 | 1,5-anhydro-2,3-dideoxy-3-(6-(4-((2-(dimethylamino)-2-oxoethyl)carbamoyl)benzyl)-7,8-dimethyl-4-oxoquinazolin-3 (4H)-yl)-L-threo-pentitol | | | 493.2 |
| 31 | 1,5-anhydro-2,3-dideoxy-3-(6-(4-((2-methoxy-2-methylpropyl)carbamoyl)benzyl)-7,8-dimethyl-4-oxoquinazolin-3 (4H)-yl)-L-threo-pentitol | | | 494.3 |
| 32 | 1,5-anhydro-2,3-dideoxy-3-(7,8-dimethyl-4-oxo-6-(4-(tetrahydro-2H-pyran-4-ylcarbamoyl)benzyl)quinazolin-3 (4H)-yl)-L-threo-pentitol | | | 492.3 |

TABLE 1-8
| Ex. No. | IUPAC name | structural formula | salt | MS |
|---|---|---|---|---|
| 33 | 1,5-anhydro-2,3-dideoxy-3-(7,8-dimethyl-4-oxo-6-(4-(tetrahydrofuran-3-ylcarbamoyl)benzyl)quinazolin-3(4H)-yl)-L-threo-pentitol | 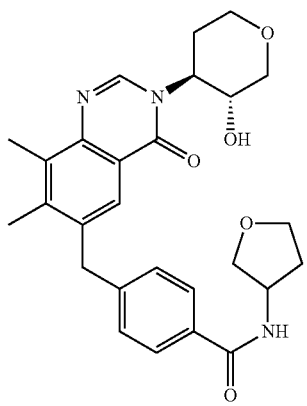 [SMILES: Cc1c(Cc2ccc(C(=O)NC3CCOC3)cc2)cc2c(=O)n([C@H]3CCOC[C@@H]3O)cnc2c1C] | | 478.2 |
| 34 | 1,5-anhydro-2,3-dideoxy-3-(6-(4-((3-fluoropropyl)carbamoyl)benzyl)-7,8-dimethyl-4-oxoquinazolin-3(4H)-yl)-L-threo-pentitol | 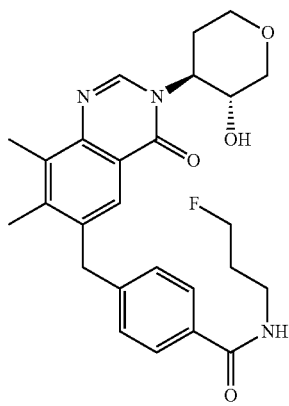 [SMILES: Cc1c(Cc2ccc(C(=O)NCCCF)cc2)cc2c(=O)n([C@H]3CCOC[C@@H]3O)cnc2c1C] | | 468.2 |
| 35 | 1,5-anhydro-2,3-dideoxy-3-(6-(4-((1-(difluoromethyl)-cyclopropyl)carbamoyl)benzyl)-7,8-dimethyl-4-oxoquinazolin-3(4H)-yl)-L-threo-pentitol | 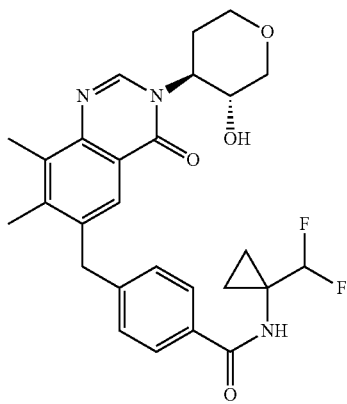 [SMILES: Cc1c(Cc2ccc(C(=O)NC3(C(F)F)CC3)cc2)cc2c(=O)n([C@H]3CCOC[C@@H]3O)cnc2c1C] | | 498.2 |

TABLE 1-8-continued

| Ex. No. | IUPAC name | structural formula | salt | MS |
|---|---|---|---|---|
| 36 | 1,5-anhydro-2,3-dideoxy-3-(6-(4-(isopropylcarbamoyl)benzyl)-7,8-dimethyl-4-oxoquinazolin-3 (4H)-yl)-L-threo-pentitol | | | 450.2 |
| 37 | 1,5-anhydro-2,3-dideoxy-3-(6-(4-((2-fluoroethyl)carbamoyl)benzyl)-7,8-dimethyl-4-oxoquinazolin-3 (4H)-yl)-L-threo-pentitol | | | 454.2 |

TABLE 1-9

| Ex. No. | IUPAC name | structural formula | salt | MS |
|---|---|---|---|---|
| 38 | 1,5-anhydro-2,3-dideoxy-3-(6-(4-((3-methoxypropyl)carbamoyl)benzyl)-7,8-dimethyl-4-oxoquinazolin-3 (4H)-yl)-L-threo-pentitol | | | 480.2 |

TABLE 1-9-continued

| Ex. No. | IUPAC name | structural formula | salt | MS |
|---|---|---|---|---|
| 39 | 1,5-anhydro-2,3-dideoxy-3-(6-(4-((2-hydroxy-2-methylpropyl)carbamoyl)benzyl)-7,8-dimethyl-4-oxoquinazolin-3(4H)-yl)-L-threo-pentitol | | | 480.2 |
| 40 | 1,5-anhydro-2,3-dideoxy-3-(6-(4-((3-hydroxyazetidin-1-yl)carbonyl)benzyl)-7,8-dimethyl-4-oxoquinazolin-3(4H)-yl)-L-threo-pentitol | | | 464.2 |
| 41 | 1,5-anhydro-2,3-dideoxy-3-(6-(4-((3-methoxyazetidin-1-yl)carbonyl)benzyl)-7,8-dimethyl-4-oxoquinazolin-3(4H)-yl)-L-threo-pentitol | | | 478.2 |

TABLE 1-9-continued

| Ex. No. | IUPAC name | structural formula | salt | MS |
|---|---|---|---|---|
| 42 | 1,5-anhydro-3-(6-(4-(bicyclo[1.1.1]penta-1-ylcarbamoyl)benzyl)-7,8-dimethyl-4-oxoquinazolin-3 (4H)-yl)-2,3-dideoxy-L-threo-pentitol | | | 474.2 |

TABLE 1-10

| Ex. No. | IUPAC name | structural formula | salt | MS |
|---|---|---|---|---|
| 43 | 1,5-anhydro-2,3-dideoxy-3-(7,8-dimethyl-6-(4-((1-methylcyclopropyl)carbamoyl)-benzyl)-4-oxoquinazolin-3 (4H)-yl)-L-threo-pentitol | | | 462.2 |
| 44 | 1,5-anhydro-3-(6-(4-(cyclopropylcarbamoyl)benzyl)-7,8-dimethyl-4-oxoquinazolin-3 (4H)-yl)-2,3-dideoxy-L-threo pentitol | | | 448.2 |

TABLE 1-10-continued

| Ex. No. | IUPAC name | structural formula | salt | MS |
|---|---|---|---|---|
| 45 | 1,5-anhydro-2,3-dideoxy-3-(7,8-dimethyl-4-oxo-6-(4-((tetrahydrofuran-2-ylmethyl)carbamoyl)benzyl)quinazolin-3 (4H)-yl)-L-threo-pentitol | | | 492.3 |
| 46 | 1,5-anhydro-2,3-dideoxy-3-(6-(4-((3-fluorocyclobutyl)-carbamoyl)benzyl)-7,8-dimethyl-4-oxoquinazolin-3 (4H)-yl)-L-threo-pentitol | | | 480.2 |
| 47 | 1,5-anhydro-2,3-dideoxy-3-(7,8-dimethyl-6-(4-((2-(morpholin-4-yl)ethyl)carbamoyl)benzyl)-4-oxoquinazolin-3 (4H)-yl)-L-threo-pentitol | | | 521.3 |

TABLE 1-11

| Ex. No. | IUPAC name | structural formula | salt | MS |
|---|---|---|---|---|
| 48 | 1,5-anhydro-2,3-dideoxy-3-(6-(4-((1-hydroxy-2-methylpropan-2-yl)carbamoyl)benzyl)-7,8-dimethyl-4-oxoquinazolin-3 (4H)-yl)-L-threo-pentitol | | | 480.2 |
| 49 | 1,5-anhydro-2,3-dideoxy-3-(6-(4-((2-methoxyethyl)carbamoyl)benzyl)-7,8-dimethyl-4-oxoquinazolin-3 (4H)-yl)-L-threo-pentitol | | | 466.1 |
| 50 | 1,5-anhydro-2,3-dideoxy-3-(6-(4-((2-hydroxyethyl)carbamoyl)benzyl)-7,8-dimethyl-4-oxoquinazolin-3 (4H)-yl)-L-threo-pentitol | | | 452.2 |

TABLE 1-11-continued

| Ex. No. | IUPAC name | structural formula | salt | MS |
|---|---|---|---|---|
| 51 | 1,5-anhydro-2,3-dideoxy-3-(7,8-dimethyl-4-oxo-6-(4-((tetrahydro-2H-pyran-4-ylmethyl)carbamoyl)-benzyl)quinazolin-3 (4H)-yl)-L-threo-pentitol | | | 506.3 |
| 52 | 1,5-anhydro-2,3-dideoxy-3-(6-(4-((3-(difluoromethyl)azetidin-1-yl)carbonyl)benzyl)-7,8-dimethyl-4-oxoquinazolin-3 (4H)-yl)-L-threo-pentitol | | | 498.2 |

TABLE 1-12

| Ex. No. | IUPAC name | structural formula | salt | MS |
|---|---|---|---|---|
| 53 | 1,5-anhydro-2,3-dideoxy-3-(7,8-dimethyl-4-oxo-6-(4-((3,3,3-trifluoropropyl)carbamoyl)-benzyl)quinazolin-3 (4H)-yl)-L-threo-pentitol | | | 504.2 |

TABLE 1-12-continued

| Ex. No. | IUPAC name | structural formula | salt | MS |
|---|---|---|---|---|
| 54 | 1,5-anhydro-3-(8-chloro-7-methyl-6-((6-(1-methyl-1H-pyrazol-4-yl)pyridin-3-yl)methyl)-4-oxo-1,2,3-benzotriazin-3 (4H)-yl)-2,3-dideoxy-L-threo-pentitol | | | 467.1 |
| 55 | 1,5-anhydro-2,3-dideoxy-3-(6-(3-fluoro-4-(methylcarbamoyl)benzyl)-7,8-dimethyl-4-oxo-1,2,3-benzotriazin-3 (4H)-yl)-L-threo-pentitol | | | 441.1 |
| 56 | 1,5-anhydro-3-(6-((6-(1-cyclopropyl-1H-pyrazol-4-yl)pyridin-3-yl)methyl)-7,8-dimethyl-4-oxoquinazolin-3 (4H)-yl)-2,3-dideoxy-L-threo-pentitol | | | 472.2 |

TABLE 1-12-continued

| Ex. No. | IUPAC name | structural formula | salt | MS |
|---|---|---|---|---|
| 57 | 1,5-anhydro-2,3-dideoxy-3-(6-(3-fluoro-4-(methylcarbamoyl)benzyl)-7-methoxy-4-oxoquinazolin-3 (4H)-yl)-L-threo-pentitol | | | 442.1 |

TABLE 1-13

| Ex. No. | IUPAC name | structural formula | salt | MS |
|---|---|---|---|---|
| 58 | 1,5-anhydro-2,3-dideoxy-3-(7-methoxy-6-((6-(1-methyl-1H-pyrazol-4-yl)pyridin-3-yl)methyl)-4-oxoquinazolin-3 (4H)-yl)-L-threo-pentitol | | | 448.1 |
| 59 | 1,5-anhydro-2,3-dideoxy-3-(7,8-dimethyl-6-((6-(1-methyl-1H-pyrazol-3-yl)pyridin-3-yl)methyl)-4-oxo-1,2,3-benzotriazin-3 (4H)-yl)-L-threo-pentitol | | | 447.1 |

TABLE 1-13-continued

| Ex. No. | IUPAC name | structural formula | salt | MS |
|---|---|---|---|---|
| 60 | 1,5-anhydro-3-(6-(4-carboxy-3-fluorobenzyl)-7,8-dimethyl-4-oxoquinazolin-3 (4H)-yl)-2,3-dideoxy-L-threo-pentitol | | | 427.2 |
| 61 | 1,5-anhydro-2,3-dideoxy-3-(7-methoxy-6-(4-(1-methyl-1H-imidazol-4-yl)benzyl)-4-oxoquinazolin-3 (4H)-yl)-L-threo-pentitol | | | 447.1 |
| 62 | 1,5-anhydro-2,3-dideoxy-3-(7,8-dimethyl-6-((6-(1-methyl-1H-1,2,3-triazol-4-yl)pyridin-3-yl)methyl)-4-oxo-1,2,3-benzotriazin-3 (4H)-yl)-L-threo-pentitol | | | 448 |

TABLE 1-14

| Ex. No. | IUPAC name | structural formula | salt | MS |
|---|---|---|---|---|
| 63 | 1,5-anhydro-2,3-dideoxy-3-(7-methoxy-6-((6-(1-methyl-1H-pyrazol-3-yl)pyridin-3-yl)methyl)-4-oxoquinazolin-3 (4H)-yl)-L-threo-pentitol | | | 448.1 |
| 64 | 1,5-anhydro-2,3-dideoxy-3-(7-methoxy-6-((6-(1-methyl-1H-1,2,3-triazol-4-yl)pyridin-3-yl)methyl)-4-oxoquinazolin-3 (4H)-yl)-L-threo-pentitol | | | 449.1 |
| 65 | 1,5-anhydro-2,3-dideoxy-3-(6-(3-fluoro-4-((3-methyloxetan-3-yl)carbamoyl)benzyl)-7,8-dimethyl-4-oxoquinazolin-3 (4H)-yl)-L-threo-pentitol | | | 496.1 |

TABLE 1-14-continued

| Ex. No. | IUPAC name | structural formula | salt | MS |
|---|---|---|---|---|
| 66 | 1,5-anhydro-2,3-dideoxy-3-(6-(3-fluoro-4-((2-methoxyethyl)carbamoyl)benzyl)-7,8-dimethyl-4-oxoquinazolin-3 (4H)-yl)-L-threo-pentitol (synonym) 2-fluoro-4-((3-((3R,4S)-3-hydroxytetrahydro-2H-pyran-4-yl)-7,8-dimethyl-4-oxo-3,4-dihydroquinazolin-6-yl)methyl)-N-(2-methoxyethyl)benzamide | | | 484.2 |

TABLE 1-15

| Ex. No. | IUPAC name | structural formula | salt | MS |
|---|---|---|---|---|
| 67 | 1,5-anhydro-2,3-dideoxy-3-(6-(3-fluoro-4-((2-fluoroethyl)carbamoyl)benzyl)-7,8-dimethyl-4-oxoquinazolin-3 (4H)-yl)-L-threo-pentitol | | | 472.2 |
| 68 | 1,5-anhydro-2,3-dideoxy-3-(6-(4-((2-(dimethylamino)-2-oxoethyl)carbamoyl)-3-fluorobenzyl)-7,8-dimethyl-4-oxoquinazolin-3 (4H)-yl)-L-threo-pentitol | | | 511.2 |

TABLE 1-15-continued

| Ex. No. | IUPAC name | structural formula | salt | MS |
|---|---|---|---|---|
| 69 | 1,5-anhydro-2,3-dideoxy-3-(6-(3-fluoro-4-(methylcarbamoyl)benzyl)-7,8-dimethyl-4-oxoquinazolin-3 (4H)-yl)-D-threo-pentitol | | | 440.1 |
| 70 | 1,5-anhydro-2,3-dideoxy-3-(6-(3-fluoro-4-((3-(methylsulfonyl)propyl)-carbamoyl)benzyl)-7,8-dimethyl-4-oxoquinazolin-3 (4H)-yl)-L-threo-pentitol | | | 546.2 |

TABLE 1-16

| Ex. No. | IUPAC name | structural formula | salt | MS |
|---|---|---|---|---|
| 71 | 1,5-anhydro-3-(6-((6-(1-(cyclopropylmethyl)-1H-pyrazol-4-yl)pyridin-3-yl)methyl)-7,8-dimethyl-4-oxoquinazolin-3 (4H)-yl)-2,3-dideoxy-L-threo-pentitol (synonym) 6-((6-(1-(cyclopropylmethyl)-1H-pyrazol-4-yl)pyridin-3-yl)methyl)-3-((3R,4S)-3-hydroxytetrahydro-2H-pyran-4-yl)-1,8-dimethylquinazolin-4 (3H)-one | | | 486.2 |

TABLE 1-16-continued

| Ex. No. | IUPAC name | structural formula | salt | MS |
|---|---|---|---|---|
| 72 | 1,5-anhydro-3-(6-((6-(1-tert-butyl-1H-pyrazol-4-yl)pyridin-3-yl)methyl)-7,8-dimethyl-4-oxoquinazolin-3 (4H)-yl)-2,3-dideoxy-L-threo-pentitol (synonym) 6-((6-(1-(tert-butyl)-1H-pyrazol-4-yl)pyridin-3-yl)methyl)-3-((3R,4S)-3-hydroxytetrahydro-2H-pyran-4-yl)-7,8-dimethylquinazolin-4 (3H)-one | | | 488.2 |
| 73 | 1,5-anhydro-2,3-dideoxy-3-(6-((6-(1-(2-methoxyethyl)-1H-pyrazol-4-yl)pyridin-3-yl)methyl)-7,8-dimethyl-4-oxoquinazolin-3 (4H)-yl)-L-threo-pentitol (synonym) 3-((3R,4S)-3-hydroxytetrahydro-2H-pyran-4-yl)-6-((6-(1-(2-methoxyethyl)-1H-pyrazol-4-yl)pyridin-3-yl)methyl)-7,8-dimethylquinazolin-4 (3H)-one | | | 490.2 |

TABLE 1-17

| Ex. No. | IUPAC name | structural formula | salt | MS |
|---|---|---|---|---|
| 74 | 1,5-anhydro-2,3-dideoxy-3-(7,8-dimethyl-4-oxo-6-((6-(1-(2,2,2-trifluoroethyl)-1H-pyrazol-4-yl)pyridin-3-yl)methyl)quinazolin-3 (4H)-yl)-L-threo-pentitol (synonym) 3-((3R,4S)-3-hydroxytetrahydro-2H-pyran-4-yl)-7,8-dimethyl-6-((6-(1-(2,2,2-trifluoroethyl)-1H-pyrazol-4-yl)pyridin-3-yl)methyl)quinazolin-4 (3H)-one | | | 514.1 |
| 75 | 1,5-anhydro-2,3-dideoxy-3-(7,8-dimethyl-4-oxo-6-((6-(1-(tetrahydro-2H-pyran-4-yl)-1H-pyrazol-4-yl)pyridin-3-yl)methyl)quinazolin-3 (4H)-yl)-L-threo-pentitol (synonym) 3-((3R,4S)-3-hydroxytetrahydro-2H-pyran-4-yl)-7,8-dimethyl-6-((6-(1-(tetrahydro-2H-pyran-4-yl)-1H-pyrazol-4-yl)pyridin-3-yl)methyl)quinazolin-4 (3H)-one | | | 516.2 |
| 76 | 1,5-anhydro-2,3-dideoxy-3-(6-(3-fluoro-4-(((1-hydroxycyclopropyl)methyl)-carbamoyl)benzyl)-7,8-dimethyl-4-oxoquinazolin-3 (4H)-yl)-L-threo-pentitol | | | 496.1 |

TABLE 1-17-continued

| Ex. No. | IUPAC name | structural formula | salt | MS |
|---|---|---|---|---|
| 77 | 1,5-anhydro-2,3-dideoxy-3-(6-(3-fluoro-4-((2-(2-oxopyrrolidin-1-yl)ethyl)carbamoyl)benzyl)-7,8-dimethyl-4-oxoquinazolin-3(4H)-yl)-L-threo-pentitol | 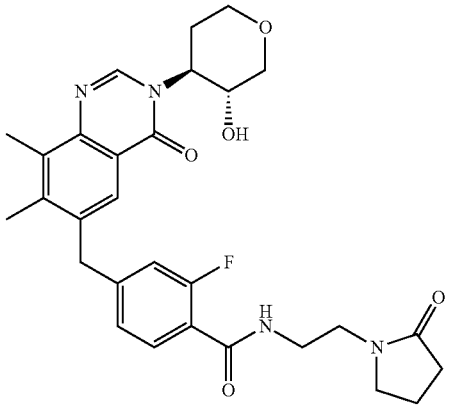 [SMILES: Cc1c(Cc2ccc(C(=O)NCCN3CCCC3=O)c(F)c2)cc2c(=O)n([C@H]3CCOC[C@@H]3O)cnc2c1C] | | 537.2 |

TABLE 1-18

| Ex. No. | IUPAC name | structural formula | salt | MS |
|---|---|---|---|---|
| 78 | 1,5-anhydro-2,3-dideoxy-3-(6-(3-fluoro-4-((2-(pyrrolidin-1-yl)ethyl)carbamoyl)benzyl)-7,8-dimethyl-4-oxoquinazolin-3(4H)-yl)-L-threo-pentitol | 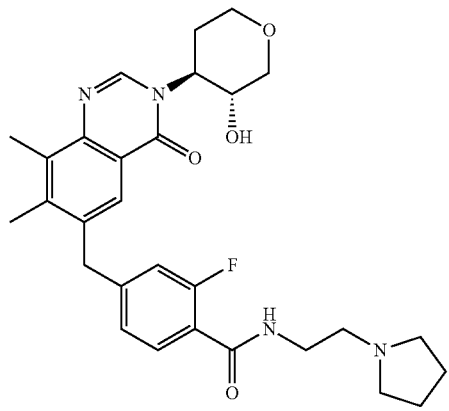 [SMILES: Cc1c(Cc2ccc(C(=O)NCCN3CCCC3)c(F)c2)cc2c(=O)n([C@H]3CCOC[C@@H]3O)cnc2c1C] | | 523.2 |
| 79 | 1,5-anhydro-2,3-dideoxy-3-(6-(3-fluoro-4-((oxetan-3-ylmethyl)carbamoyl)benzyl)-7,8-dimethyl-4-oxoquinazolin-3(4H)-yl)-L-threo-pentitol | 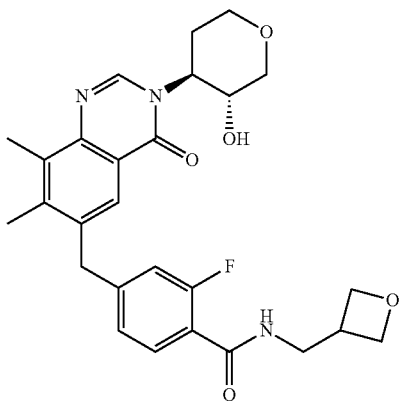 [SMILES: Cc1c(Cc2ccc(C(=O)NCC3COC3)c(F)c2)cc2c(=O)n([C@H]3CCOC[C@@H]3O)cnc2c1C] | | 496.2 |

TABLE 1-18-continued

| Ex. No. | IUPAC name | structural formula | salt | MS |
|---|---|---|---|---|
| 80 | 1,5-anhydro-2,3-dideoxy-3-(6-(3-fluoro-4-(((2S)-tetrahydrofuran-2-ylmethyl)carbamoyl)benzyl)-7,8-dimethyl-4-oxoquinazolin-3(4H)-yl)-L-threo-pentitol | | | 510.2 |
| 81 | 1,5-anhydro-2,3-dideoxy-3-(6-(3-fluoro-4-(((2R)-tetrahydrofuran-2-ylmethyl)carbamoyl)benzyl)-7,8-dimethyl-4-oxoquinazolin-3(4H)-yl)-L-threo-pentitol (synonym) 2-fluoro-4-((3-((3R,4S)-3-hydroxytetrahydro-2H-pyran-4-yl)-7,8-dimethyl-4-oxo-3,4-dihydroquinazolin-6-yl)methyl)-N-(((R)-tetrahydrofuran-2-yl)methyl)benzamide | | | 510.2 |

TABLE 1-19

| Ex. No. | IUPAC name | structural formula | salt | MS |
|---|---|---|---|---|
| 82 | 1,5-anhydro-2,3-dideoxy-3-(6-((6-(1-(2-(dimethylamino)-2-oxoethyl)-1H-pyrazol-4-yl)pyridin-3-yl)methyl)-7,8-dimethyl-4-oxoquinazolin-3(4H)-yl)-L-threo-pentitol | | | 517.2 |

TABLE 1-19-continued

| Ex. No. | IUPAC name | structural formula | salt | MS |
|---|---|---|---|---|
| 83 | 1,5-anhydro-2,3-dideoxy-3-(6-(4-((1,1-dioxidethietan-3-yl)carbamoyl)-3-fluorobenzyl)-7,8-dimethyl-4-oxoquinazolin-3 (4H)-yl)-L-threo-pentitol | | | 530.1 |
| 84 | 1,5-anhydro-2,3-dideoxy-3-(6-(3-fluoro-4-((2-(methylsulfonyl)ethyl)-carbamoyl)benzyl)-7,8-dimethyl-4-oxoquinazolin-3 (4H)-yl)-L-threo-pentitol | | | 532.1 |
| 85 | 1,5-anhydro-2,3-dideoxy-3-(6-(4-((2-ethoxyethyl)carbamoyl)-3-fluorobenzyl)-7,8-dimethyl-4-oxoquinazolin-3 (4H)-yl)-L-threo-pentitol (synonym) N-(2-ethoxyethyl)-2-fluoro-4-((3-((3R,4S)-3-hydroxytetrahydro-2H-pyran-4-yl)-7,8-dimethyl-4-oxo-3,4-dihydroquinazolin-6-yl)methyl)benzamide | | | 498.2 |

TABLE 1-20

| Ex. No. | IUPAC name | structural formula | salt | MS |
|---|---|---|---|---|
| 86 | 1,5-anhydro-2,3-dideoxy-3-(6-(3-fluoro-4-((3-methoxypropyl)carbamoyl)-benzyl)-7,8-dimethyl-4-oxoquinazolin-3 (4H)-yl)-L-threo-pentitol (synonym) 2-fluoro-4-((3-((3R,4S)-3-hydroxytetrahydro-2H-pyran-4-yl)-1,8-dimethyl-4-oxo-3,4-dihydroquinazolin-6-yl)methyl)-N-(3-methoxypropyl)benzamide | | | 498.1 |
| 87 | 1,5-anhydro-3-(6-(4-(cyclopropylcarbamoyl)-3-fluorobenzyl)-7,8-dimethyl-4-oxoquinazolin-3 (4H)-yl)-2,3-dideoxy-L-threo-pentitol (synonym) N-cyclopropyl-2-fluoro-4-((3-((3R,4S)-3-hydroxytetrahydro-2H-pyran-4-yl)-7,8-dimethyl-4-oxo-3,4-dihydroquinazolin-6-yl)methyl)benzamide | | | 466.1 |
| 88 | 2-fluoro-N-((3R,4S)-3-hydroxytetrahydro-2H-pyran-4-yl)-4-((3-((3R,4S)-3-hydroxytetrahydro-2H-pyran-4-yl)-7,8-dimethyl-4-oxo-3,4-dihydroquinazolin-6-yl)methyl)benzamide | | | 526.2 |

TABLE 1-20-continued

| Ex. No. | IUPAC name | structural formula | salt | MS |
|---|---|---|---|---|
| 89 | 1,5-anhydro-3-(6-(4-((1-cyanocyclopropyl)carbamoyl)-3-fluorobenzyl)-7,8-dimethyl-4-oxoquinazolin-3 (4H)-yl)-2,3-dideoxy-L-threo-pentitol | | | 491.2 |

TABLE 1-21

| Ex. No. | IUPAC name | structural formula | salt | MS |
|---|---|---|---|---|
| 90 | 1,5-anhydro-3-(6-((6-carboxypyridin-3-yl)methyl)-7,8-dimethyl-4-oxo-1,2,3-benzotriazin-3 (4H)-yl)-2,3-dideoxy-L-threo-pentitol | | | 411.1 |
| 91 | 1,5-anhydro-2,3-dideoxy-3-(7,8-dimethyl-6-((6-(methylcarbamoyl)pyridin-3-yl)methyl)-4-oxo-1,2,3-benzotriazin-3 (4H)-yl)-L-threo-pentitol | | | 424 |

TABLE 1-21-continued

| Ex. No. | IUPAC name | structural formula | salt | MS |
|---|---|---|---|---|
| 92 | 1,5-anhydro-2,3-dideoxy-3-(6-(fluoro(3-fluoro-4-(methylcarbamoyl)phenyl)methyl)-7,8-dimethyl-4-oxoquinazolin-3(4H)-yl)-L-threo-pentitol (diastereomeric mixture) | | | 458.1 |
| 93 | 1,5-anhydro-2,3-dideoxy-3-(6-(fluoro(3-fluoro-4-(methylcarbamoyl)phenyl)methyl)-7,8-dimethyl-4-oxoquinazolin-3(4H)-yl)-L-threo-pentitol (epimer of Example 94) | | | 458.1 |
| 94 | 1,5-anhydro-2,3-dideoxy-3-(6-(fluoro(3-fluoro-4-(methylcarbamoyl)phenyl)methyl)-7,8-dimethyl-4-oxoquinazolin-3(4H)-yl)-L-threo-pentitol (epimer of Example 93) | | | 458.1 |

Comparative Example 1

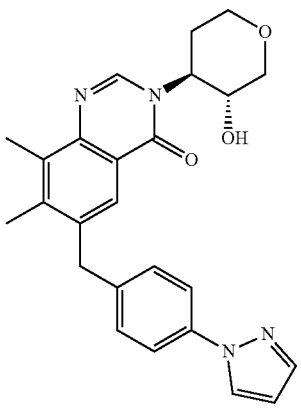 [SMILES: Cc1c(Cc2ccc(-n3cccn3)cc2)cc2c(=O)n([C@H]3CCOC[C@@H]3O)cnc2c1C]

3-((3R,4S)-3-hydroxytetrahydro-2H-pyran-4-yl)-7,8-dimethyl-6-(4-(1H-pyrazol-1-yl)benzyl)quinazolin-4(3H)-one Synonym: 1,5-anhydro-2,3-dideoxy-3-(7,8-dimethyl-4-oxo-6-(4-(1H-pyrazol-1-yl)benzyl)quinazolin-3(4H)-yl)-L-threo-pentitol

A) 2-amino-5-bromo-3,4-dimethylbenzoic acid

To a solution of 2-amino-3,4-dimethylbenzoic acid (2.0 g) in DMSO (25 mL) was added hydrobromic acid (48% v/v, 10.2 g) under water cooling, and the mixture was stirred at room temperature for 48 hr. To the reaction mixture was added water (25 mL), and the mixture was cooled at 0° C. for 10 min. The precipitate was collected by filtration, washed with water, and dried under reduced pressure to give the title compound (2.41 g).
MS: [M−H]⁻ 242.0, 244.0.

B) methyl 2-amino-5-bromo-3,4-dimethylbenzoate

To a mixed solution of 2-amino-5-bromo-3,4-dimethylbenzoic acid (3.0 g) and DMF (50 mL) was added cesium carbonate (6.01 g), and the mixture was stirred at room temperature for 30 min. To the reaction solution was added methyl iodide (2.09 g), and the mixture was stirred at room temperature overnight. To the reaction mixture was added water, and the mixture was extracted with ethyl acetate. The organic layer was washed with water, and dried over anhydrous magnesium sulfate and the solvent was evaporated under reduced pressure. The residue was purified by silica gel column chromatography (ethyl acetate/hexane) to give the title compound (3.0 g).
MS: [M+H]⁺ 257.8, 259.8

C) methyl 2-amino-3,4-dimethyl-5-(4,4,5,5-tetramethyl-1,3,2-dioxaborolan-2-yl)benzoate To a mixture of methyl 2-amino-5-bromo-3,4-dimethylbenzoate (3.7 g), bis(pinacolato)diboron (7.28 g), potassium acetate (4.22 g) and toluene (100 mL) was added bis(triphenylphosphine)palladium(II) chloride (1.01 g), and the mixture was stirred under an argon atmosphere at 110° C. overnight. Insoluble material was filtered off and the filtrate was concentrated under reduced pressure. The residue was purified by silica gel column chromatography (ethyl acetate/hexane) and triturated with ethyl acetate-hexane to give the title compound (0.7 g).
MS: [M+H]⁺ 306.0

D) methyl 5-(4-(1H-pyrazol-1-yl)benzyl)-2-amino-3,4-dimethylbenzoate

To a mixture of methyl 2-amino-3,4-dimethyl-5-(4,4,5,5-tetramethyl-1,3,2-dioxaborolan-2-yl)benzoate (0.69 g), 1-(4-(chloromethyl)phenyl)-1H-pyrazole (0.46 g), 2 M aqueous sodium carbonate solution (2.26 mL) and DME (20 mL) was added (1,1-bis(diphenylphosphino)ferrocene)dichloropalladium(II) dichloromethane adduct (0.09 g) under an argon atmosphere and the mixture was stirred at 80° C. overnight. The reaction mixture was dried over anhydrous sodium sulfate and concentrated under reduced pressure. The residue was purified by silica gel column chromatography (ethyl acetate/hexane) to give the title compound (0.65 g).
MS: [M+H]⁺ 336.1

E) 5-(4-(1H-pyrazol-1-yl)benzyl)-2-amino-3,4-dimethylbenzoic acid

To a mixed solution of methyl 5-(4-(1H-pyrazol-1-yl)benzyl)-2-amino-3,4-dimethylbenzoate (0.65 g) and THF (5 mL)-methanol (5 mL) was added 8 M aqueous sodium hydroxide solution (2.42 mL), and the mixture was stirred at 60° C. for 5 hr. The reaction mixture was adjusted with 6 M hydrochloric acid to pH 4 under ice-cooling. The resulting precipitate was collected by filtration, washed with water and dried under reduced pressure to give the title compound (0.51 g).
MS: [M+H]⁺ 322.1

F) 5-(4-(1H-pyrazol-1-yl)benzyl)-2-amino-N-((3R,4S)-3-hydroxytetrahydro-2H-pyran-4-yl)-3,4-dimethylbenzamide To a mixture of 5-(4-(1H-pyrazol-1-yl)benzyl)-2-amino-3,4-dimethylbenzoic acid (0.50 g), (3R,4S)-4-aminotetrahydro-2H-pyran-3-ol hydrochloride (0.25 g), WSC hydrochloride (0.36 g), HOBt monohydrate (0.26 g) and DMF (3 mL) was added triethylamine (0.32 g), and the mixture was stirred at room temperature for 4 hr. To the reaction mixture was added water, and the precipitate was collected by filtration, washed with water and dried under reduced pressure to give the title compound (0.65 g).
MS: [M+H]⁺ 421.2

G) 3-((3R,4S)-3-hydroxytetrahydro-2H-pyran-4-yl)-7,8-dimethyl-6-(4-(1H-pyrazol-1-yl)benzyl)quinazolin-4(3H)-one Synonym: 1,5-anhydro-2,3-dideoxy-3-(7,8-dimethyl-4-oxo-6-(4-(1H-pyrazol-1-yl)benzyl)quinazolin-3(4H)-yl)-L-threo-pentitol A mixture of 5-(4-(1H-pyrazol-1-yl)benzyl)-2-amino-N-((3R,4S)-3-hydroxytetrahydro-2H-pyran-4-yl)-3,4-dimethylbenzamide (0.50 g) and N,N-dimethylformamide dimethyl acetal (1.6 mL) was stirred at 90° C. for 4 hr. The reaction mixture was concentrated under reduced pressure, water was added to the residue, and the mixture was stirred at room temperature for 10 min. The precipitate was collected by filtration, washed with water and dried under reduced pressure. The obtained solid was purified by silica gel column chromatography (ethyl acetate/hexane) and triturated with ethyl acetate to give the title compound (0.22 g).

$^1$H NMR (300 MHz, DMSO-$d_6$) δ1.78-1.91 (1H, m), 2.08-2.24 (1H, m), 2.29 (3H, s), 2.53 (3H, s), 3.11 (1H, t, J=10.4 Hz), 3.35-3.49 (1H, m), 3.85-4.00 (2H, m), 4.02-4.15 (1H, m), 4.19 (2H, s), 4.41-4.61 (1H, m), 5.23 (1H, d, J=5.5 Hz), 6.50-6.53 (1H, m), 7.20-7.29 (2H, m), 7.71 (1H, d, J=1.7 Hz), 7.72-7.77 (2H, m), 7.84 (1H, s), 8.39-8.48 (2H, m).

Comparative Example 2

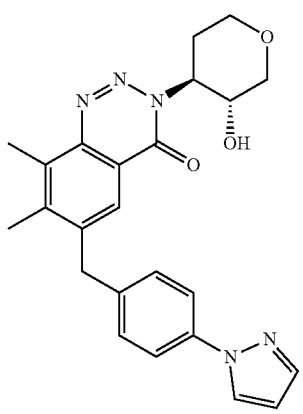 [SMILES: Cc1c(Cc2ccc(-n3cccn3)cc2)cc2c(=O)n([C@H]3CCOC[C@@H]3O)nnc2c1C]

3-((3R,4S)-3-hydroxytetrahydro-2H-pyran-4-yl)-7,8-dimethyl-6-(4-(1H-pyrazol-1-yl)benzyl)-1,2,3-benzotriazin-4(3H)-one Synonym: 1,5-anhydro-2,3-dideoxy-3-(7,8-dimethyl-4-oxo-6-(4-(1H-pyrazol-1-yl)benzyl)-1,2,3-benzotriazin-3(4H)-yl)-L-threo-pentitol To a mixture of 5-(4-(1H-pyrazol-1-yl)benzyl)-2-amino-N-((3R,4S)-3-hydroxytetrahydro-2H-pyran-4-yl)-3,4-dimethylbenzamide (0.15 g) and 2 M hydrochloric acid (1.07 mL) was added dropwise under ice-cooling a solution of sodium nitrite (0.03 g) in water (1.0 mL), and the mixture was stirred at room temperature for 3 hr. The reaction mixture was neutralized with 8 M aqueous sodium hydroxide solution under ice-cooling, and the precipitate was collected by filtration. The obtained solid was further purified by silica gel column chromatography (ethyl acetate/hexane) and triturated with ethyl acetate to give the title compound (0.15 g).

$^1$H NMR (300 MHz, DMSO-$d_6$) δ1.93 (1H, dd, J=12.8, 4.3 Hz), 2.13 (1H, qd, J=12.5, 4.6 Hz), 2.38 (3H, s), 2.76 (3H, s), 3.20 (1H, t, J=10.7 Hz), 3.44-3.56 (1H, m), 3.88-4.01 (2H, m), 4.10 (1H, ddt, J=15.1, 10.1, 5.0 Hz), 4.30 (2H, s), 4.97 (1H, ddd, J=11.9, 9.8, 4.5 Hz), 5.21 (1H, d, J=5.1 Hz), 6.52 (1H, dd, J=2.5, 1.7 Hz), 7.22-7.30 (2H, m), 7.71 (1H, d, J=1.3 Hz), 7.74-7.81 (2H, m), 7.93 (1H, s), 8.44 (1H, dd, J=2.5, 0.4 Hz).

Formulation Example 1

| | |
|---|---|
| (1) compound obtained in Example 1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is passed through a 1 mm mesh sieve and granulated by using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of sucrose, titanium dioxide, talc and gum arabic. The coated tablets are glazed with beeswax to give 1000 coated tablets.

Formulation Example 2

| | |
|---|---|
| (1) compound obtained in Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

Experimental Example 1

Measurement of M1 Receptor Positive Allosteric Modulator (M1PAM) Activity

The activity of a test compound in the presence of acetylcholine at EC20 concentration (final concentration 0.8-1.0 nM), which affords an action corresponding to about 20% of the maximum activity, was measured as PAM activity. The method is as follows. CHO-K1 cells stably expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and assay buffer A containing calcium indicator (Recording medium (DOJINDO LABORATORIES), 0.1% BSA (Wako Pure Chemical Industries, Ltd.), 2.5 μg/mL Fluo-4 AM (DOJINDO LABORATORIES), 0.08% Pluronic F127 (DOJINDO LABORATORIES), 1.25 mM probenecid (DOJINDO LABORATORIES)) was added at 30 μL/well. The cells were left standing in the incubator at 37° C., 5% $CO_2$ for 30 min, and further left standing at room temperature for 30 min. A test compound prepared by diluting with assay buffer B (HBSS (Invitrogen), 20 mM HEPES (Invitrogen), 0.1% BSA) containing 3.2-4.0 nM acetylcholine was added at 10 μL/well, and the fluorescence was measured by FDSS/pCELL (Hamamatsu Photonics K.K.) for 1 min every for 1 second. With the definition that the amount of change in the fluorescence on addition of acetylcholine (final concentration 1 μM) is 100% and that on addition of DMSO instead of a test compound is 0%, the activity (%) of the test compound was calculated, and the inflection point in the concentration-dependent curve of the test compound was calculated as IP values. The results are shown in Table 2.

TABLE 2

| Ex. No. | IP value (nM) | activity (%) at 10 μM |
|---|---|---|
| 1 | 2.1 | 101 |
| 2 | 1.5 | 104 |
| 3 | 1.0 | 103 |
| 4 | 2.0 | 101 |
| 5 | 1.5 | 97 |
| 6 | 0.96 | 99 |
| 8 | 1.4 | 97 |
| 9 | 3.3 | 109 |
| 11 | 0.91 | 100 |
| 13 | 1.0 | 101 |
| 18 | 1.0 | 106 |
| 19 | 1.6 | 103 |
| 24 | 3.7 | 108 |
| 25 | 1.9 | 109 |
| 27 | 1.4 | 110 |
| 29 | 1.6 | 112 |
| 33 | 1.8 | 111 |
| 39 | 3.3 | 112 |
| 41 | 11 | 108 |
| 49 | 1.1 | 101 |
| 50 | 0.80 | 103 |
| 54 | 0.99 | 106 |
| 56 | 2.1 | 107 |
| 58 | 1.9 | 103 |
| 59 | 2.6 | 108 |
| 61 | 2.2 | 108 |
| 62 | 2.5 | 107 |
| 65 | 3.0 | 109 |
| 66 | 1.8 | 106 |
| 68 | 1.7 | 106 |
| 71 | 2.5 | 107 |
| 73 | 1.4 | 109 |
| 75 | 3.0 | 108 |
| 76 | 1.9 | 106 |
| 77 | 2.0 | 107 |
| 79 | 1.5 | 108 |
| 80 | 1.9 | 107 |
| 81 | 3.7 | 110 |
| 83 | 1.5 | 109 |
| 84 | 1.9 | 106 |
| 85 | 2.1 | 107 |
| 86 | 3.1 | 110 |
| 87 | 2.3 | 111 |

Experimental Example 2

Mouse Defecation Experiment

Male ICR mice (6-7 weeks old) were used after an acclimation period for about 1 week. A test drug (1 mg/kg or 3 mg/kg) was suspended in 0.5% methylcellulose solution and orally administered at a volume of 10 mL/kg, and the number of feces 2 hr later was counted. Only 0.5% methylcellulose was administered to a solvent administration group.

The results are shown in Table 3. The results show mean±standard error.

TABLE 3

| Ex. No. | | solvent administration group 0 mg/kg | dose 1 mg/kg | 3 mg/kg |
|---|---|---|---|---|
| 2 | number of feces 2 hr later | 4.2 ± 1.2 | 5.0 ± 0.7 | 11.3 ± 0.6 |
| 3 | number of feces 2 hr later | 3.7 ± 1.0 | 14.0 ± 1.0 | — |
| 5 | number of feces 2 hr later | 1.8 ± 0.6 | 5.6 ± 1.0 | 8.4 ± 2.6 |
| 6 | number of feces 2 hr later | 1.8 ± 0.6 | 7.2 ± 1.8 | 8.2 ± 1.0 |
| 19 | number of feces 2 hr later | 2.6 ± 0.8 | 12.6 ± 1.2 | — |
| 66 | number of feces 2 hr later | 4.0 ± 1.0 | 9.3 ± 1.2 | — |

Experimental Example 3

Mouse PK test

As the mouse, 8-week-old male ICR mice (Japan SLC, Inc.) were used. They were fed on a solid commercially available diet (CE-2, CLEA Japan, Inc.) and allowed to freely ingest tap water as the drinking water. An intravenous administration solution for the mice was prepared by weighing a test compound, dissolving same in dimethylacetamide (DMA) (Wako Pure Chemical Industries, Ltd.), adding the same volume of 1,3-butanediol (Wako Pure Chemical Industries, Ltd.) and mixing by stirring to give a DMA:1,3-butanediol (1:1, v/v) solution. An oral administration solution was prepared by weighing a test compound, pulverizing same in an agate mortar, and gradually adding 0.5 w/v % aqueous methylcellulose solution to give a suspension. For intravenous administration, the solution was administered into femoral vein of the mice at 0.1 mg/mL/kg (salt converted to free form). For oral administration, the suspension was administered to the mice at 1 mg/5 mL/kg (salt converted to free form). The cassette dosing method was used for the both administration routes, and the test compound was administered in the following manner.

Compound of Example 2 (intravenous: 4 compounds cassette administration, oral: 4 compounds cassette administration)

Compound of Example 3 (intravenous: 10 compounds cassette administration, oral: 5 compounds cassette administration)

Compound of Example 5 (intravenous: 5 compounds cassette administration, oral: 5 compounds cassette administration)

Compound of Example 6 (intravenous: 9 compounds cassette administration, oral: 5 compounds cassette administration)

Compound of Example 19 (intravenous: 5 compounds cassette administration, oral: 5 compounds cassette administration)

Compound of Example 66 (intravenous: 10 compounds cassette administration, oral: 5 compounds cassette administration)

Compound of Example 81 (intravenous: 10 compounds cassette administration, oral: 5 compounds cassette administration)

In the case of intravenous administration, blood samples were collected from the tail vein at 5, 10, 15, 30 min, 1, 2, 4, 8 hr after administration, an anticoagulation treatment with heparin sodium (Shimizu Pharmaceutical Co., Ltd.) was performed, and plasma was collected after centrifugation and subjected to the measurement of drug concentration. In the case of oral administration, blood samples were collected from the tail vein at 15, 30 min, 1, 2, 4, 8 hr after administration, an anticoagulation treatment with heparin sodium was performed, and plasma was collected after centrifugation and subjected to the measurement of drug concentration.

All drug concentrations were measured by LC-MS/MS analysis. For a pharmacokinetics test, the plasma (5 μL) was placed in a tube, acetonitrile (115 μL) containing internal standard solution was added and they were mixed on a vortex mixer. Thereafter, the mixture was centrifuged (5000 rpm, 5 min, 4° C.). The supernatant (100 μL) after centrifugation was added to 10 mmol/L ammonium formate (100 μL) added earlier and mixed therewith. This sample was injected to LC/MS/MS. The HPLC system used was Shimadzu LC-20A (Shimadzu Corporation), the column used was Unison UK-C18 HT (3.0 μm, 2.0×20 mm, Imtakt) at 50° C., and 10 mmol/L ammonium formate, 0.2% formic acid as mobile phase A and acetonitrile, 0.2% formic acid as mobile phase B were fed each at a flow rate of 1.2 mL/min under gradient conditions of (B concentration: 0 min→0.1 min, 5%, 0.1→0.75 min, 5-99%, 0.75→1.15 min, 99%, 1.15→41.16 min, 5%, 1.16→1.5 min, 5%). MS/MS used was AB Sciex TQ5500-MPX (Applied Biosystems).

The results are shown in Table 4.
Tmax: time to reach maximum plasma concentration
MRT: mean residence time
iv: intravenous administration
CL total: total clearance

TABLE 4

| Example No. | Tmax (h) | MRT iv (h) | CL total (mL/h/kg) |
|---|---|---|---|
| 2 | 1.0 | 1.0 | 657 |
| 3 | 1.7 | 1.9 | 609 |
| 5 | 0.7 | 1.2 | 447 |
| 6 | 1.7 | 1.4 | 273 |
| 19 | 1.7 | 2.5 | 274 |
| 66 | 0.7 | 0.8 | 1598 |
| 81 | 0.5 | 0.5 | 4329 |

Experimental Example 4

MDR1 Membrane Permeability Test

When MDR1 is expressed in excess in LLC-PK1 cell, which is a polar cell, MDR1 is localized in apical membrane (A), thus promoting transcellular transport from the basement membrane side (B) toward direction A. When a ratio to the transcellular transport in the opposite direction is taken and a ratio to a control cell in which a mock vector has been introduced is further taken, an efflux ratio of MDR1 to simple diffusion (corrected efflux ratio) is calculated. Similarly, when a brain/plasma concentration ratio in Mdr1(−/−) mouse is divided by a brain/plasma concentration ratio in wild-type mouse, an efflux ratio of Mdr1 to simple diffusion in BBB (Kp, brain ratio, higher value means lower central nervous system permeability) is calculated. Adachi Y. et al. (Reference 1) has reported a positive correlation between corrected efflux ratio and Kp, brain ratio (FIG. 5(C)), and efflux ratio in MDR1 expressing cell and Kp, brain ratio (FIG. 5(B)). That is, the report shows that a higher efflux ratio of MDR1 in vitro results in lower central nervous system permeability.

To confirm the central nervous system permeability of the compounds of the present invention, a MDR1 membrane permeability test was performed by the following method.

Digoxin and lucifer yellow (LY) were purchased from Sigma-Aldrich, Diclofenac, colchicine and alprenolol were purchased from Wako Pure Chemical Industries, Ltd., and other reagents used were commercially available products of special grade.

Human MDR1-expressing LLC-PK1 cells were cultured according to the report of Takeuchi et al. (Reference 2). Human MDR1-expressing LLC-PK1 cells were cultured in 10% fetal bovine serum (Invitrogen), 500 μg/ml G418 (Invitrogen), 150 ng/ml colchicine-containing M199 medium (Invitrogen) under 5% $CO_2$ conditions at 37° C.

Transcellular transport was performed according to the report of Sugimoto et al. (Reference 3). The cells were cultured for 3 days on HTS Transwell (registered trademark) 96 well permeable support (pore size 0.4 μm, 0.143 $cm^2$ surface area, Corning Life Sciences) having polyethylene terephthalate membrane on which the cells had been seeded at $3.45 \times 10^4$ cells/well. After preincubation in M199 medium (containing 10 mmol/L HEPES, 1% BSA, pH 7.4) for 30 min, a drug solution (10 μmol/L digoxin, 200 μmol/L LY, 10 μmol/L test compound) dissolved in M199 medium was added to the apical side or basolateral side of the Transwell by 75 or 250 μL each and the cells were cultured under 5% $CO_2$ conditions at 37° C. After 1 hr, the sample was collected from the side opposite to the side where the drug solution was added, and the concentration of the test compound was measured by LC-MS/MS. As an internal standard substance, 100 ng/mL alprenolol and diclofenac were used. The analysis conditions were as follows.

LC: UFLC LC-20 (Shimadzu)
MS/MS: API4000 (AB Sciex Instruments)
LC condition: gradient method

TABLE 5

| Time (min) | Pump B (%) |
|---|---|
| 0.02 | 5 |
| 0.40 | 95 |
| 0.80 | 95 |
| 0.81 | 5 |
| 1.50 | Stop |

Column: Unison UK-C18 HT (3.0 μm, 2.0×20 mm)
Column temperature: 50° C.
Flow rate: 0.7 mL/min (for 1.5 min run), 1.0 mL/min (for 1.0 min run)
Mobile phase A: 50 mM $CH_3COONH_4$:MeCN:water=1:1:8
Mobile phase B: 50 mM $CH_3COONH_4$:MeCN=1:9
Injection volume: 1-20 μL LY was measured by a fluorescence plate reader (Fluoroskan Ascent FL).

$P_{app}$, A to B and $P_{app}$, B to A (apparent permeability) were calculated from the formula (1), and the efflux ratio (ER) was calculated from the formula (2).

$$P_{app} = \frac{Amount}{Area \times C_0 \times Time} \quad (1)$$

Amount: amount of transported digoxin/well
Area: surface area of cell monolayer (0.143 cm$^2$)
$C_0$: concentration of drug solution added
Time: incubation time $$ER = \frac{P_{app}, B \text{ to } A}{P_{app}, A \text{ to } B} \quad (2)$$

The results are shown in Table 6.

TABLE 6

| Example No. | MDR1 substrate screening 1 μM (MDRSUB1)/Ratio (NUMBER) |
|---|---|
| Comparative Example 1 | 0.83 |
| Comparative Example 2 | 1.3 |
| 1 | 4.7 |
| 2 | 18 |
| 3 | 6 |
| 4 | 5.7 |
| 5 | 15 |
| 6 | 11 |
| 7 | 3.5 |
| 8 | 4.8 |
| 9 | 2.1 |
| 10 | 15 |
| 11 | 17 |
| 12 | 17 |
| 13 | 38 |
| 14 | 22 |
| 15 | 9.7 |
| 16 | 6.8 |
| 18 | 24 |
| 19 | 4.6 |
| 20 | 2.9 |
| 21 | 20 |
| 22 | 12 |
| 23 | 19 |
| 24 | 3.4 |
| 25 | 16 |
| 26 | 24 |
| 27 | 23 |
| 28 | 11 |
| 29 | 12 |
| 30 | 24 |
| 31 | 12 |
| 32 | 26 |
| 33 | 20 |
| 34 | 20 |
| 35 | 9 |
| 36 | 11 |
| 37 | 12 |
| 38 | 15 |
| 40 | 12 |
| 41 | 13 |
| 42 | 5.9 |
| 43 | 12 |
| 44 | 22 |
| 45 | 23 |
| 46 | 18 |
| 47 | 24 |
| 48 | 24 |
| 49 | 20 |
| 50 | 13 |
| 51 | 27 |
| 52 | 18 |
| 53 | 8.3 |
| 54 | 9.5 |
| 55 | 3.2 |
| 56 | 4.9 |
| 57 | 16 |
| 58 | 19 |
| 59 | 3.7 |
| 61 | 32 |
| 62 | 9.4 |
| 63 | 35 |
| 64 | 36 |
| 65 | 15 |
| 66 | 7 |
| 67 | 5.3 |
| 68 | 19 |
| 70 | 13 |
| 71 | 8 |
| 72 | 2.9 |
| 73 | 18 |
| 74 | 7.1 |
| 75 | 13 |
| 76 | 15 |
| 77 | 32 |
| 78 | 56 |
| 79 | 26 |
| 80 | 9.5 |
| 81 | 8.6 |
| 82 | >18 |
| 83 | 19 |
| 84 | 11 |
| 85 | 10 |
| 86 | 7.8 |
| 87 | 8.7 |
| 88 | 16 |
| 89 | 16 |
| 91 | 5.9 |

Experimental Example 5

Rat Defecation Experiment

Male SD rats (5-6 weeks old) were used after an acclimation period for about 1 week. A test drug (1 mg/kg, 3 mg/kg, or 10 mg/kg) was suspended in 0.5% methylcellulose solution and orally administered at a volume of 5 mL/kg, and the number of feces 2 hr later was counted. Only 0.5% methylcellulose was administered to a solvent administration group.

The results are shown in Table 7. The results show mean±standard error.

TABLE 7

| Ex. No. | | dose | | | |
|---|---|---|---|---|---|
| | | solvent administration group 0 mg/kg | 1 mg/kg | 3 mg/kg | 10 mg/kg |
| 3 | number of feces 2 hr later | 3.4 ± 1.0 | 7.4 ± 0.7 | 7.8 ± 1.4 | — |
| 66 | number of feces 2 hr later | 3.6 ± 0.4 | 9.9 ± 1.0 | — | — |
| 81 | number of feces 2 hr later | 5.1 ± 0.7 | 6.9 ± 1.1 | 7.0 ± 0.8 | 11.5 ± 1.1 |

REFERENCES

1. Adachi Y. et al., Comparative studies on in vitro methods for evaluating in vivo function of MDR1 P-glycoprotein, Pharm. Res. 18:1660-1668, 2001
2. Takeuchi T., Yoshitomi S., Higuchi T., Ikemoto K., Niwa S., Ebihara T., Katoh M., Yokoi T. and Asahi S., Establishment and characterization of the transformants stably-expressing MDR1 derived from various animal species in LLC-PK1, Pharm. Res., 23(7):1460-1472, 2006

3. Sugimoto H., Hirabayashi H., Kimura Y., Furuta A., Amano N. and Moriwaki T., Quantitative investigation of the impact of P-glycoprotein inhibition on drug transport across blood-brain barrier in rats, Drug Metab. Dispos., 39(1):8-14, 2011

INDUSTRIAL APPLICABILITY

The compound of the present invention may have a cholinergic muscarinic M1 receptor positive allosteric modulator activity and may be useful as a medicament such as an agent for the prophylaxis or treatment of constipation and the like.

This application is based on patent application No. 2017-81919 filed in Japan, the entire contents of which are incorporated by reference herein.

The invention claimed is:

1. 2-Fluoro-4-((3-((3R,4S)-3-hydroxytetrahydro-2H-pyran-4-yl)-7,8-dimethyl-4-oxo-3,4-dihydroquinazolin-6-yl)methyl)-N—(((R)-tetrahydrofuran-2-yl)methyl)benzamide, or a salt thereof.

2. A pharmaceutical composition comprising the compound according to claim 1 or a salt thereof, and a pharmacologically acceptable carrier.

3. A method of cholinergic muscarinic M1 receptor positive allosteric modulation in a mammal, comprising administering an effective amount of the compound according to claim 1 or a salt thereof to said mammal.

4. A method for treatment of constipation in a mammal, comprising administering an effective amount of the compound according to claim 1 or a salt thereof to the mammal.

* * * * *